(12) United States Patent
Yeleswaram et al.

(10) Patent No.: US 12,226,418 B2
(45) Date of Patent: Feb. 18, 2025

(54) DOSING REGIMEN FOR THE TREATMENT OF PI3K RELATED DISORDERS

(71) Applicant: Incyte Corporation, Wilmington, DE (US)

(72) Inventors: Krishnaswamy Yeleswaram, Landenberg, PA (US); Albert Assad, Jersey City, NJ (US); Xuejun Chen, Glen Mills, PA (US)

(73) Assignee: Incyte Corporation, Wilmington, DE (US)

( * ) Notice: Subject to any disclaimer, the term of this patent is extended or adjusted under 35 U.S.C. 154(b) by 146 days.

(21) Appl. No.: 16/428,056

(22) Filed: May 31, 2019

(65) Prior Publication Data

US 2019/0365764 A1 Dec. 5, 2019

Related U.S. Application Data

(60) Provisional application No. 62/773,612, filed on Nov. 30, 2018, provisional application No. 62/714,448, filed on Aug. 3, 2018, provisional application No. 62/679,556, filed on Jun. 1, 2018.

(51) Int. Cl.
*A61K 31/519* (2006.01)
*A61P 35/00* (2006.01)

(52) U.S. Cl.
CPC ............ *A61K 31/519* (2013.01); *A61P 35/00* (2018.01)

(58) Field of Classification Search
CPC .................................................. A61K 31/519
See application file for complete search history.

(56) References Cited

U.S. PATENT DOCUMENTS

| | | |
|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender |
| 3,936,454 A | 2/1976 | Schwender |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmerman |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopt et al. |
| 7,528,143 B2 | 5/2009 | Noronha et al. |
| 7,598,257 B2 | 10/2009 | Rodgers et al. |
| 7,612,114 B2 | 11/2009 | Hamaoka et al. |
| 7,745,437 B2 | 6/2010 | Ren et al. |
| 7,834,022 B2 | 11/2010 | Rodgers et al. |
| 8,410,265 B2 | 4/2013 | Zhou et al. |
| 8,530,485 B2 | 9/2013 | Rodgers et al. |
| 8,541,425 B2 | 9/2013 | Rodgers et al. |
| 8,604,043 B2 | 12/2013 | Li et al. |
| 8,680,108 B2 | 3/2014 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,759,359 B2 | 6/2014 | Combs et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,889,697 B2 | 11/2014 | Arvanitis et al. |
| 8,933,085 B2 | 1/2015 | Rodgers et al. |
| 8,933,086 B2 | 1/2015 | Rodgers et al. |
| 8,940,752 B2 | 1/2015 | Li et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

No Author, "A Phase 1, Open-label, Dose Escalation, Safety and Tolerability Study of INCB040093 in Subjects with Previously Treated B-Cell Malignancies," start date Jun. 2013, retrieved on May 24, 2017, https://clinicaltrials.gov/archive/NCT01905813/2013_12_13, 1 page.

Aka et al., "Elevated serum levels of interleukin-6 in endemic Burkitt lymphoma in Ghana," Hematol Oncol, Dec. 2014, 32(4):218-20.

Akinleye et al., "Phosphatidylinositol 3-kinase (PI3K) inhibitors as cancer therapeutics," Journal of Hematology & Oncology, 2013, 6:88.

Ali et al., "Essential role for the p110δ phosphoinositide 3-kinase in the allergic response," Nature. 2004, 431(7011):1007-1011.

Allen et al., "Synthesis of C-6 substituted pyrazolo[1,5-a]pyridines with potent activity against herpesviruses," Bioorganic & Medicinal Chemistry 2006, 14(4):944-954.

Apsel et al., "Targeted polypharmacology: discovery of dual inhibitors of tyrosine and phosphoinositide kinases," Nat. Chem. Biol., 2008, 4(11):691-699.

(Continued)

*Primary Examiner* — Yong S. Chong
(74) *Attorney, Agent, or Firm* — Fish & Richardson P.C.

(57) ABSTRACT

The present application provides methods of treating PI3Kδ related disorders using pyrazolopyrimidine derivatives.

45 Claims, 8 Drawing Sheets

(56) References Cited

U.S. PATENT DOCUMENTS

| | | |
|---|---|---|
| 8,946,245 B2 | 2/2015 | Rodgers et al. |
| 8,987,443 B2 | 3/2015 | Liu et al. |
| 9,023,840 B2 | 5/2015 | Yao et al. |
| 9,034,884 B2 | 5/2015 | Rodgers et al. |
| 9,062,055 B2 | 6/2015 | Li et al. |
| 9,079,912 B2 | 7/2015 | Rodgers et al. |
| 9,096,600 B2 | 8/2015 | Li et al. |
| 9,108,984 B2 | 8/2015 | Combs et al. |
| 9,126,948 B2 | 9/2015 | Combs et al. |
| 9,181,271 B2 | 11/2015 | Li et al. |
| 9,193,721 B2 | 11/2015 | Combs et al. |
| 9,199,982 B2 | 12/2015 | Li et al. |
| 9,206,187 B2 | 12/2015 | Rodgers et al. |
| 9,216,984 B2 | 12/2015 | Li et al. |
| 9,221,845 B2 | 12/2015 | Liu et al. |
| 9,249,087 B2 | 2/2016 | Kozikowski et al. |
| 9,249,145 B2 | 2/2016 | Rodgers et al. |
| 9,309,251 B2 | 4/2016 | Combs et al. |
| 9,334,274 B2 | 5/2016 | Rodgers et al. |
| 9,359,358 B2 | 6/2016 | Rodgers et al. |
| 9,376,439 B2 | 6/2016 | Rodgers et al. |
| 9,382,231 B2 | 7/2016 | Li et al. |
| 9,403,847 B2 | 8/2016 | Combs et al. |
| 9,434,746 B2 | 9/2016 | Li et al. |
| 9,464,088 B2 | 10/2016 | Huang et al. |
| 9,487,521 B2 | 11/2016 | Zhou et al. |
| 9,498,467 B2 | 11/2016 | Leopold et al. |
| 9,527,848 B2 | 12/2016 | Li et al. |
| 9,707,233 B2 | 7/2017 | Li et al. |
| 9,730,939 B2 | 8/2017 | Li et al. |
| 9,815,839 B2 | 11/2017 | Li et al. |
| 9,932,341 B2 | 4/2018 | Li et al. |
| 9,944,646 B2 | 4/2018 | Combs et al. |
| 9,975,907 B2 | 5/2018 | Li et al. |
| 9,988,401 B2 | 6/2018 | Li et al. |
| 10,064,866 B2 | 9/2018 | Scherle et al. |
| 10,077,277 B2 | 9/2018 | Li et al. |
| 10,092,570 B2 | 10/2018 | Li et al. |
| 10,125,150 B2 | 11/2018 | Li et al. |
| 10,259,818 B2 | 4/2019 | Combs et al. |
| 10,336,759 B2 | 7/2019 | Qiao et al. |
| 10,376,513 B2 | 8/2019 | Sparks et al. |
| 10,428,087 B2 | 10/2019 | Li et al. |
| 10,479,803 B2 | 11/2019 | Li et al. |
| 10,675,284 B2 | 6/2020 | Scherle et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player et al. |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2008/0312259 A1 | 12/2008 | Rodgers et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto et al. |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0113416 A1 | 5/2010 | Friedman et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0166164 A1 | 7/2011 | Brewster |
| 2011/0183985 A1 | 7/2011 | Li et al. |
| 2011/0190319 A1 | 8/2011 | Combs et al. |
| 2011/0207754 A1 | 8/2011 | Li et al. |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0288107 A1 | 11/2011 | Parikh et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2012/0301464 A1 | 11/2012 | Friedman et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0094477 A1 | 4/2014 | Rodgers et al. |
| 2014/0121198 A1 | 5/2014 | Li et al. |
| 2014/0121222 A1 | 5/2014 | Li et al. |
| 2014/0124222 A1 | 5/2014 | Li |
| 2014/0135350 A1 | 5/2014 | Ni et al. |
| 2014/0249132 A1* | 9/2014 | Li .................. A61P 35/00 514/210.18 |
| 2014/0275031 A1 | 9/2014 | Huang |
| 2014/0275127 A1 | 9/2014 | Combs et al. |
| 2014/0343030 A1 | 11/2014 | Li et al. |
| 2015/0065447 A1 | 3/2015 | Sandor et al. |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0164900 A1 | 6/2015 | Rodgers et al. |
| 2015/0225411 A1 | 8/2015 | Yao et al. |
| 2015/0238492 A1 | 8/2015 | Rodgers et al. |
| 2015/0246046 A1 | 9/2015 | Vaddi et al. |
| 2015/0250790 A1 | 9/2015 | Parikh et al. |
| 2015/0284390 A1 | 10/2015 | Li et al. |
| 2015/0344497 A1 | 12/2015 | Zhou et al. |
| 2015/0361094 A1 | 12/2015 | Li et al. |
| 2016/0000079 A1 | 1/2016 | Linington et al. |
| 2016/0000795 A1 | 1/2016 | Scherle et al. |

(56) References Cited

U.S. PATENT DOCUMENTS

| | | |
|---|---|---|
| 2016/0015695 A1 | 1/2016 | Li et al. |
| 2016/0022685 A1 | 1/2016 | Li et al. |
| 2016/0024109 A1 | 1/2016 | Li et al. |
| 2016/0024117 A1 | 1/2016 | Li et al. |
| 2016/0067253 A1 | 3/2016 | Li et al. |
| 2016/0257689 A1 | 9/2016 | Qiao et al. |
| 2016/0264580 A1 | 9/2016 | Combs et al. |
| 2016/0272648 A1 | 9/2016 | Rodgers et al. |
| 2016/0289215 A1 | 10/2016 | Li et al. |
| 2016/0346286 A1 | 12/2016 | Rodgers et al. |
| 2016/0347734 A1 | 12/2016 | Liu et al. |
| 2016/0362424 A1 | 12/2016 | Li et al. |
| 2016/0362425 A1 | 12/2016 | Li et al. |
| 2016/0362426 A1 | 12/2016 | Zhou et al. |
| 2017/0050987 A1 | 2/2017 | Li et al. |
| 2017/0158696 A1 | 6/2017 | Li et al. |
| 2018/0258105 A1 | 9/2018 | Li et al. |
| 2018/0344740 A1 | 12/2018 | Scherle et al. |
| 2018/0362546 A1 | 12/2018 | Li et al. |
| 2019/0002470 A1 | 1/2019 | Combs et al. |
| 2019/0040067 A1 | 2/2019 | Li et al. |
| 2019/0084997 A1 | 3/2019 | Li et al. |
| 2019/0134040 A1 | 5/2019 | Li et al. |
| 2019/0202840 A1 | 7/2019 | Li et al. |
| 2019/0298724 A1 | 10/2019 | Sparks et al. |
| 2019/0308979 A1 | 10/2019 | Qiao et al. |
| 2019/0365764 A1 | 12/2019 | Yeleswaram et al. |

FOREIGN PATENT DOCUMENTS

| | | | | |
|---|---|---|---|---|
| CL | 201602566 | 2/2017 | | |
| CN | 102458581 | 5/2012 | | |
| CN | 102482278 | 5/2012 | | |
| CN | 102985417 | 3/2013 | | |
| CN | 103415515 | 11/2013 | | |
| CN | 105120871 | 12/2015 | | |
| CN | 107580597 | 1/2018 | | |
| DE | 1770420 | 11/1971 | | |
| DE | 2139107 | 2/1973 | | |
| EP | 255085 | 2/1988 | | |
| EP | 464612 | 1/1992 | | |
| EP | 481614 | 4/1992 | | |
| EP | 1138328 | 11/2001 | | |
| EP | 1109805 | 12/2003 | | |
| EP | 1783114 | 5/2007 | | |
| EP | 1972631 | 9/2008 | | |
| EP | 2031037 | 3/2009 | | |
| EP | 2050749 | 4/2009 | | |
| EP | 934307 | 4/2011 | | |
| GB | 1440478 | 6/1976 | | |
| GB | 1472342 | 5/1977 | | |
| JP | 50111080 | 9/1975 | | |
| JP | 53059663 | 5/1978 | | |
| JP | 53092767 | 8/1978 | | |
| JP | 56025234 | 6/1981 | | |
| JP | 56123981 | 9/1981 | | |
| JP | 58083698 | 5/1983 | | |
| JP | 62103640 | 5/1987 | | |
| JP | 62245252 | 10/1987 | | |
| JP | 1250316 | 10/1989 | | |
| JP | 4190232 | 7/1992 | | |
| JP | 9087282 | 3/1997 | | |
| JP | 9176116 | 7/1997 | | |
| JP | 10025294 | 1/1998 | | |
| JP | 10231297 | 9/1998 | | |
| JP | 2000080295 | 3/2000 | | |
| JP | 2000281654 | 10/2000 | | |
| JP | 2001151771 | 6/2001 | | |
| JP | 2005035924 | 2/2005 | | |
| JP | 2009080233 | 4/2009 | | |
| JP | 2009120686 | 6/2009 | | |
| JP | 2011511761 | 4/2011 | | |
| JP | 2011136925 | 7/2011 | | |
| JP | 6067709 | 1/2017 | | |
| JP | 6263591 | 1/2018 | | |
| JP | 6266743 | 1/2018 | | |
| JP | 6427257 | 11/2018 | | |
| RU | 2233842 | 8/2004 | | |
| SU | 1712359 | 2/1992 | | |
| WO | WO 1993/16076 | 8/1993 | | |
| WO | WO 1993/22291 | 11/1993 | | |
| WO | WO 1993/25524 | 12/1993 | | |
| WO | WO 1999/43651 | 9/1999 | | |
| WO | WO 1999/43672 | 9/1999 | | |
| WO | WO 2000/009495 | 2/2000 | | |
| WO | WO-0013712 A2 * | 3/2000 | ............ | A61K 31/28 |
| WO | WO 2000/044750 | 8/2000 | | |
| WO | WO 2000/053595 | 9/2000 | | |
| WO | WO 2001/014402 | 3/2001 | | |
| WO | WO 2001/064639 | 9/2001 | | |
| WO | WO 2001/064655 | 9/2001 | | |
| WO | WO 2001/072709 | 10/2001 | | |
| WO | WO 2002/000196 | 1/2002 | | |
| WO | WO 2002/006477 | 1/2002 | | |
| WO | WO 2002/024685 | 3/2002 | | |
| WO | WO 2002/064599 | 8/2002 | | |
| WO | WO 2002/066478 | 8/2002 | | |
| WO | WO 2002/078701 | 10/2002 | | |
| WO | WO 2003/020721 | 3/2003 | | |
| WO | WO 2003/024967 | 3/2003 | | |
| WO | WO 2003/029209 | 4/2003 | | |
| WO | WO 2003/037347 | 5/2003 | | |
| WO | WO 2003/044014 | 5/2003 | | |
| WO | WO 2003/049678 | 6/2003 | | |
| WO | WO 2003/050064 | 6/2003 | | |
| WO | WO 2003/068750 | 8/2003 | | |
| WO | WO 2003/074497 | 9/2003 | | |
| WO | WO 2003/099771 | 12/2003 | | |
| WO | WO 2004/005281 | 1/2004 | | |
| WO | WO 2004/024693 | 3/2004 | | |
| WO | WO 2004/046120 | 6/2004 | | |
| WO | WO 2004/048365 | 6/2004 | | |
| WO | WO 2004/056786 | 7/2004 | | |
| WO | WO 2004/069256 | 8/2004 | | |
| WO | WO 2004/076455 | 9/2004 | | |
| WO | WO 2004/080980 | 9/2004 | | |
| WO | WO 2004/087704 | 10/2004 | | |
| WO | WO 2004/107863 | 12/2004 | | |
| WO | WO 2004/113335 | 12/2004 | | |
| WO | WO 2005/000309 | 1/2005 | | |
| WO | WO 2005/016528 | 2/2005 | | |
| WO | WO 2005/028444 | 3/2005 | | |
| WO | WO 2005/046578 | 5/2005 | | |
| WO | WO 2005/091857 | 10/2005 | | |
| WO | WO 2005/113556 | 12/2005 | | |
| WO | WO 2006/008523 | 1/2006 | | |
| WO | WO 2006/030031 | 3/2006 | | |
| WO | WO 2006/056399 | 6/2006 | | |
| WO | WO 2006/068760 | 6/2006 | | |
| WO | WO 2006/089106 | 8/2006 | | |
| WO | WO 2007/002701 | 1/2007 | | |
| WO | WO 2007/012724 | 2/2007 | | |
| WO | WO 2007/042806 | 4/2007 | | |
| WO | WO 2007/076092 | 7/2007 | | |
| WO | WO 2007/087548 | 8/2007 | | |
| WO | WO 2007/095588 | 8/2007 | | |
| WO | WO 2007/102392 | 9/2007 | | |
| WO | WO 2007/114926 | 10/2007 | | |
| WO | WO 2007/126841 | 11/2007 | | |
| WO | WO 2008/002490 | 1/2008 | | |
| WO | WO 2008/005303 | 1/2008 | | |
| WO | WO 2008/025821 | 3/2008 | | |
| WO | WO 2008/032033 | 3/2008 | | |
| WO | WO 2008/064018 | 5/2008 | | |
| WO | WO 2008/064157 | 5/2008 | | |
| WO | WO 2008/082490 | 7/2008 | | |
| WO | WO 2008/097991 | 8/2008 | | |
| WO | WO 2008/100867 | 8/2008 | | |
| WO | WO 2008/116129 | 9/2008 | | |
| WO | WO 2008/118454 | 10/2008 | | |
| WO | WO 2008/118468 | 10/2008 | | |
| WO | WO 2009/026701 | 3/2009 | | |
| WO | WO 2009/034386 | 3/2009 | | |
| WO | WO 2009/062118 | 5/2009 | | |

(56) References Cited

FOREIGN PATENT DOCUMENTS

| | | |
|---|---|---|
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/068450 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2012/177606 | 12/2012 |
| WO | WO 2013/023119 | 2/2013 |
| WO | WO 2013/033569 | 3/2013 |
| WO | WO 2013/052699 | 4/2013 |
| WO | WO 2013/072392 | 5/2013 |
| WO | WO 2013/151930 | 10/2013 |
| WO | WO 2015/191677 | 12/2015 |
| WO | WO 2016/183063 | 6/2016 |
| WO | WO 2016/138363 | 9/2016 |
| WO | WO 2016/183060 | 11/2016 |
| WO | WO 2016/183062 | 11/2016 |
| WO | WO-2016209961 A1 * | 12/2016 ............ A61K 31/52 |

OTHER PUBLICATIONS

Argentina Office Action in Argentina Application No. P120103232, dated Aug. 20, 2019, 3 pages.
Atzrodt et al., "The Renaissance of H/D Exchange," Angew Chem Int Ed., 2007, 46:7744-7765.
Australian Office Action in Australian Application No. 2015244044, dated Jun. 21, 2019, 4 pages.
Australian Office Action in Australian Application No. 2016222556, dated Aug. 28, 2019, 5 pages.
Australian Office Action in Australian Application No. 2017206260, dated Mar. 20, 2018, 4 pages.
Australian Office Action in Australian Application No. 2019201423, Oct. 28, 2019, 4 pages.
Avivi et al., "Matched unrelated donor stem cell transplant in 131 patients with follicular lymphoma: an analysis from the Lymphoma Working Party of the European Group for Blood and Marrow Transplantation," British Journal of Haematology, 2009, 147(5):719-728.
Bader et al., "Cancer-specific mutations in PIK3CA are oncogenic in vivo," Proc Natl Acad Sci U S A. 2006, 103(5):1475-1479.
Baek et al., "Complete remission induced by rituximab in refractory, seronegative, muscle-specific, kinase-positive myasthenia gravis," J Neurol Neurosurg Psychiatry, 2007, 78(7):771.
Ball, "PI3K inhibitors as potential therapeutics for autoimmune disease," Drug Discovery Today, 2014, pp. 1195-119.
Baran-Marszak et al., "Constitutive and B-cell receptor-induced activation of STAT3 are important signaling pathways targeted by bortezomib in leukemic mantle cell lymphoma," Haematologica, Nov. 2010, 95(11):1865-72.
Barber et al., "PI3Kγ inhibition blocks glomerulonephritis and extends lifespan in a mouse model of systemic lupus," Nat Med. 2005, 11(9):933-935.
Barragan et al., "Protein Kinases in the Regulation of Apoptosis in B-cell Chronic Lymphocytic Leukemia," Leukemia and Lymphoma, 2003, 44(11):1865-1870.
Bartalucci et al., "Co-targeting the PI3k/mTOR and JAK2 signalling pathways produced synergistic activity against myeloproliferative neoplasms," Journal of Cellular and Molecular Medicine, Nov. 2013, 17(11): 1385-1396.
Bartalucci et al., "Rationale for Tarketing the PI3K/Akt/mTOR Pathway in Myeloproliferative Neoplasms," Clinical Lymphoma, Myeloma & Leukemia, Sep. 2013, 13(S2):S307-S309.
Belema et al., "Synthesis and structure-activity relationship of imidazo(1,2-a)thieno(3,2-e)pyrazines as IKK-β inhibitors," Bioorganic & Medicinal Chemistry Letters, 2007, 17(15):4284-4289.
Bendell et al., "Phase I, dose-escalation study of BKM120, an oral pan-Class I PI3K inhibitor, in patients with advanced solid tumors," Journal of Clincial Oncology, 2012, 30(3):282-290.
Benistant et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-5090.
Bennasar et al., "Generation and Intermolecular Reactions of 2-Indolylacyl Radicals," Organic Letters, 2001, 3(11):1697-1700.
Benschop et al., "B cell development: signal transduction by antigen receptors and their surrogates," Current Opinion in Immunology, 1999, 11(2):143-151.
Berge et al., "Pharmaceutical Salts," J Pharma Sci, 1977, 66(1):1-19.
Bergman et al., "Synthesis of indolocarbazole quinones; potent aryl hydrocarbon receptor ligands," Tetrahedron (2002), 58(7):1443-1452.
Bhatia and Rose, "Autoimmunity and autoimmune disease," Principles of Med Biol., 1996, 6:239-263, 244.
Bhovi et al., "1,3-dipolar cycloaddition reaction: Synthesis and antimicrobial activity of some new3-ethoxycarbonyl-5-methoxy-6-bromo-2-triazolylmethylindoles," Indian Journal of Heterocyclic Chemistry, 2004, 14(1):15-18.
Billottet et al., "A selective inhibitor of the p110δ isoform of PI 3-kinase inhibits AML cell proliferation and survival and increases the cytotoic effects of VP16," Oncogene. 2006, 25(50):6648-6659.
Biswas et al., "Synthesis of a trifluoromethylindolocarbazole, novel cyclic 27- and 36-membered N-benzyltri- and -tetraindoles, and an

(56) References Cited

OTHER PUBLICATIONS

N-benzyltetraindolyltrimethane," Monatshefte fuer Chemie, 1999, 130(10):1227-1239.

Blom et al., "Optimizing Preparative LC-MS Configurations and Methods for Parallel Synthesis Purification," J Comb Chem., 2003, 5:670-683.

Blom et al., "Preparative LC-MS Purification: Improved Compound Specific Method Optimization," J Combi Chem., 2004, 6(6):874-883.

Blom et al., "Two-Pump at Column Dilution Configuration for Preparative LC-MS," J Comb Chem., 2002, 4:295-301.

Bogani et al., "mTOR inhibitors alone and in combination with JAK2 inhibitors effectively inhibit cells of myeloproliferative neoplasms," PLOS One, Jan. 2013, 8(1): e54826.

Boger, et al., "First and Second Generation Total Synthesis of the Teicoplanin Aglycon," JACS, 2001, 123(9):1862-1871.

Brachmann et al., "PI3K and mTOR inhibitors—a new generation of targeted anticancer agents," Current Opinion Cell Biol., 2009, 21:194-198.

Brazilian Office Action in Brazilian Application No. BR112014004971-8, dated Aug. 22, 2019, 5 pages.

Bringmann, et al., "Novel concepts in directed biaryl synthesis. Part 65. Synthesis and structure of a novel twofold lactone-bridged ternaphthyl," Tetrahedron Letters, 1998, 39(12):1545-1548.

Brock et al., "Roles of Gβγ in membrane recruitment and activation of p110γ/p101 phosphoinositide 3-kinaseγ," J Cell Biol., 2003, 160(1):89-99.

Brown, et al., "Small molecule inhibitors of IgE synthesis," Bioorganic & Medicinal Chemistry Letters, 2006, 16(17):4697-4699.

Burris et al., "Activity of TGR-1202, a novel once-daily PI3Kδ inhibitor, in patients with relapsed or refractory hematologic malignancies," Journal of Clinical Oncology, 2014, 32(15_suppl):2513-2513.

Cacoub et al., "Anti-CD20 monoclonal antibody (rituximab) treatment for cryoglobulinemic vasculitis: where do we stand?," Ann Rheum Dis, Mar. 2008, 67:283-287.

Caimi et al., "An Ongoing Phase 1/2 Study of INCB050465 for Relapsed/Refractory B-Cell Malignancies (CITADEL-101)," 14th International Conference on Malignant Lymphoma, Lugano, Switzerland, Jun. 14-17, 2017, Abstract 279, 1 page.

Caira, "Crystalline Polymorphism of Organic Compounds," Topic in Current Chemistry, 1998, 198:164-166, 177-180.

Camps, et al., "Blockade of PI3Kγ suppresses joint inflammation and damage in mouse models of rheumatoid arthritis," Nat Med., 2005, 11(9):936-43.

Canadian Examination Report in Canadian Application No. 2,766,100, dated Jan. 31, 2017, 3 pages.

Cancer.gov, "A to Z List of Cancers," National Cancer Institute, [retrieved on May 29, 2014], retrieved from URL<http://www.cancer.gov/cancertopics/types/alphalist.com>, 22 pages.

Cancer.gov, "Adult Acute Myeloid Leukemia Treatment (PDQ®)—Patient Version, Last Modified Jul. 30, 2012," last updated Jul. 30, 2012, [retrieved on Nov. 26, 2012] retrieved from URL <http://www.cancer.gov/cancertopics/pdq/treatment/adultAML/Patient/page1>, 5 pages.

Cannon, "Analog Design," Burger's Medicinal Chemistry and Drug Discovery, Fifth Edition, vol. 1:Principles and Practice, John Wiley and Sons, 1995, Chapter 19, pp. 783-802 (Abstract Only).

Cantley, "The Phosphoinositide 3-Kinase Pathway," Science, 2002, 296(5573):1655-1657.

Castillo-Trivino et al., "Rituximab in relapsing and progressive forms of multiple sclerosis: a systematic review," The PLOS One, Jul. 2013, 8(7):e66308.

Casulo et al., "Early Relapse of Follicular Lymphoma After Rituximab Plus Cyclophosphamide, Doxorubicin, Vincristine, and Prednisone Defines Patients at High Risk for Death: An Analysis From the National LymphoCare Study," Journal of Clinical Oncology, 2015, 33(23):2516-2522.

Chai, et al., "Synthesis and in vitro anti-hepatitis B virus activities of some ethyl 6-bromo-5-hydroxy-1H-indole-3-carboxylates," Bioorganic & Medicinal Chemistry, 2006, 14(4):911-917.

Chalhoub et al., "PTEN and the PI3-Kinase Pathway in Cancer," Annual review of pathology, 2009, 4:127-150.

Chang, "Novel phosphoinositide 3-kinase/mTOR dual inhibitor, NVP-BGT226, displays potent growth-inhibitory activity against human head and neck cancer cells in vitro and in vivo," Clinical Cancer Research, 2011, 17(22):7116-7126.

Chao, "Treatment challenges in the management of relapsed or refractory non-Hodgkin's lymphoma—novel and emerging therapies," Cancer Management and Research. 2013, 5:251-269.

Chen, "Targeting oxidative stress in embryonal rhabdomyosarcoma," Cancer cell, 2013, 24.6:710-724.

Cheson et al., "Recommendations for Initial Evaluation, Staging, and Response Assessment of Hodgkin and Non-Hodgkin Lymphoma: The Lugano Classification," Journal of Clinical Oncology, 2014, 32(27):3059-3067.

Cheson, "Novel Targeted Agents and the Need to Refine Clinical End Points in Chronic Lymphocytic Leukemia," J Clin Oncol., 2012, 30(23):2820-2822.

Chilean Office Action in Chilean Application No. 201702179, dated Jul. 17, 2019, 15 pages.

Chilean Office Action in Chilean Application No. 2179-2017, dated Nov. 11, 2019, 13 pages.

Chilean Opposition in Chilean Application No. 2179-2017, dated Oct. 2, 2018, 10 pages.

Chinese Office Action in Chinese Application No. 20150018986.8, dated Jul. 30, 2018, 14 pages.

Chinese Office Action in Chinese Application No. 201580018986.8, dated Jun. 18, 2019, 6 pages.

Chinese Office Action in Chinese Application No. 201680011760.X, dated Jul. 2, 2019, 16 pages.

Choi et al., "Inhibitors of B-cell Receptor Signaling for patients with B-cell malignancies," Cancer J., Sep. 2012, 18(5): 404-410.

Clayton, et al., "A Crucial Role for the p110δ Subunit of Phosphatidylinositol 3-Kinase in B Cell Development and Activation," J Exp Med. 2002, 196(6):753-763.

Collins et al., "Rituximab treatment of fibrillary glomerulonephritis," Am J Kidney Dis., 2008, 52(6):1158-1162.

Colombian Office Action in Colombian Application No. NC2017/0008924, dated Nov. 21, 2018, 10 pages.

Conconi et al., "Clinical activity of rituximab in extranodal marginal zone B-cell lymphoma of MALT type," Blood, 2003, 102(8):2741-2745.

Conroy, "Non-hodgkin lymphoma and circulating markers of inflammation and adiposity in a nested case-control study: the multiethnic cohort," Cancer Epidemiol Biomarkers Prev, Mar. 2013, 22:337-347.

Costa Rican Office Action in Costa Rican Application No. 2014-111, dated Nov. 8, 2018, 11 pages.

Coughlin et al., Approaches and limitations of phosphatidylinositol-3-kinase pathway activation status as a predictive biomarker in the clinical development of targeted theraphy, Breast Cancer Res Treatment, 2010, 124:1-11.

Courtney et al., "The PI3K Pathway as Drug Target in Human Cancer," J Clinc Oncol., 2010, 29:1075-1083.

Coutré et al., "Management of adverse events associated with idelalisib treatment: expert panel opinion," Leukemia & Lymphoma, 2015, 56(10):2779-2786.

Crabbe, "The PI3K inhibitor arsenal: choose your weapon!" Trends Biochem Sci., 2007, 32(10):450-456.

Cushing et al., "PI3Kδ and PI3Kγ as Targets for Autoimmune and Inflammatory Diseases," J Med Chem., Oct. 2012, 55(20):8559-8581.

Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941.

De Rooij et al., "Ibrutinib and idelalisib synergistically target BCR-controlled adhesion in MCL and CLL: a rationale for combination therapy," Blood, 2015, 125(14):2306-2309.

(56) References Cited

OTHER PUBLICATIONS

Deberardinis et al., "The Biology of Cancer: Metabolic Reprogramming Fuels Cell Growth and Proliferation," Cell Metabolism, Jan. 2008, 7:11-20.
Delmas and Meunier, "The Management of Paget's Disease of Bone," N Engl J Med., 1997, 336:558-566.
Devauchelle-Pensec, "Treatment of Primary Sjogren Syndrome with Rituximab," Annal Internal Med., 2014, 160:233-242.
Dilillo et al., "Chronic lymphocytic leukemia and regulatory B cells share IL-10 competence and immunosuppressive function.," Leukemia, Jan. 2013,27(1):170-82.
Dolezal et al., "Preparation and biological activity of 6-benzylaminopurine derivatives in plants and human cancer cells," Bioorganic & Medicinal Chemistry (2006), 14(3):875-884.
Dolezal et al., "Preparation, biological activity and endogenous occurrence of N6-benzyladenosines," Bioorganic & Medicinal Chemistry (2007), 15(11):3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya, 1993, (11):1932-1937.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 2009, 328(3):758-765.
Dreyling et al., "Newly diagnosed and relapsed follicular lymphoma: ESMO Clinical Practice Guidelines for diagnosis, treatment and follow-up," Annals of Oncology, 2016, 27(suppl_5):v83-v90.
Dreyling et al., "Newly diagnosed and relapsed mantle cell lymphoma: ESMO Clinical Practice Guidelines for diagnosis, treatment and follow-up," Annals of Oncology, 2017;28(suppl_4):iv62-iv71.
Dreyling et al., "Phosphatidylinositol 3-Kinase Inhibition by Copanlisib in Relapsed or Refractory Indolent Lymphoma," Journal of Clinical Oncology, 2017, 35(35):3898-3905.
Dushianthan et al., "Acute respiratory distress syndrome and acute lung injury," Post Graduate Med J., 2011, 87:612-622.
Ecuador office action in Ecuador application No. SP-12-11628, dated Jul. 17, 2019, 12 pages.
Engelman, "Targeting PI3K signalling in cancer: opportunities, challenges and limitations," Nature Rev: Cancer, 2009, 9:550-562.
European Extended Search Report in European Application No. 18215449.2, dated Apr. 26, 2019, 6 pages (Only cite if not allowed or final oa).
European Office Action in European Application No. 15717381.6, dated Jun. 14, 2019, 4 pages.
European Office Action in European Application No. 15717381.6, dated Oct. 10, 2019, 5 pages.
European Search Report in European Application No. 16199883.6, dated Jun. 4, 2017, 7 pages.
Fabbro et al., "Targeting Cancer with Small-Molecular-Weight Kinase Inhibitors," Kuster (ed), Kinase Inhibitors: Methods and Protocols Methods in Molecular Biology, 2012, 795:1-44.
Fadeyeva et al., "Inhibitors of early virus-cell interaction stages among 3-ethoxycarbonyl-5-hydroxy-bromoindole derivatives," Khimiko-Farmatsevticheskii Zhurnal, 1992, 26(9-10), 17-20 (with English abstract).
Fine et al., "Neoplasms of the Central Nervous System," Cancer Principles Practice Oncol., 2005, 2:1834-1887.
Fiskus et al., "Dual PI3K/AKT/mTOR Inhibitor BEZ235 Synergistically Enhances the Activity of JAK2 Inhibitor against Cultured and Primary Human Myeloproliferative Neoplasm Cells," Molecular Cancer Therapeutics, Feb. 2013, 12(5): 577-588.
Flinn et al., "Duvelisib, a novel oral dual inhibitor of PI3K-δ,ε, is clinically active in advanced hematologic malignancies," Blood, 2018, 131(8):877-887.
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, 2009, 27(15S):3543.
Floberg et al., "Extractive alkylation of 6-mercaptopurine and determination in plasma by gas chromatography-mass spectrometry," Journal of Chromatography, Biomedical Applications, 1981, 225(1):73-81.
Forcello et al., "Idelalisib: The First-in-Class Phosphatidylinositol 3-Kinase Inhibitor for Relapsed CLL, SLL, and Indolent NHL," J. Adv. Pract. Oncol. 2014, 5(6):455-459.
Forero-Torres et al., "An Ongoing Phase 1/2 Study of INCB050465 for Relapsed/Refractory B-Cell Malignancies (CITADEL-101)," Presented at the Congress of European Hematology Association, Madrid, Spain, Jun. 22-25, 2017, Abstract P633, 1 page.
Forero-Torres et al., "Parsaclisib, a potent and highly selective PI3K Delta inhibitor, in patients with relapsed or refractory B-cell Malignancies," Blood, Apr. 18, 2019, 133(16):1742-1752.
Forero-Torres et al., "Preliminary Safety, efficacy, and pharmacodynamics of a highly selective P130 Inhibitor, INCB050465, in patients with previously treated B-cell Malignancies," Cancer Research, 107th Annual Meeting of the American-Association-of-Cancer-Research (AACR), Apr. 16-20, 2016, New Orleans, LA, Jun. 30, 2016, 76(14):CT056.
Forero-Torres et al., "Presentation: Results From a Phase 1/2 Study of INCB050465, a Potent and Highly Selective PI3Kδ Inhibitor, in Patients With Relapsed or Refractory B-Cell Malignancies (CITADEL-101)," American Society of Hematology, 2017, 19 pages.
Forero-Torres et al., "Results from a Phase 1/2 Study of INCB050465, a Highly Selective and Highly Potent PI3K delta Inhibitor, in Patients with Relapsed or Refractory B-Cell Malignancies(CITADEL-101)," Blood, 59th Annual Meeting of the American-Society-of-Hematology (Ash), Dec. 9-12, 2017, Atlanta GA., Dec. 7, 2017, retrieved from URL <http://www.bloodjournal.org/content/130/Suppl_1/410>, 130(1):410.
Foukas et al., "Critical role for the p110α phosphoinositide-3-OH kinase in growth and metabolic regulation," Nature, 2006, 441:366-370.
Fruman and Bismuth, "Fine Tuning the Immune Response with P13K," Immunological Revs., 2006, 228:253-272.
Fruman, "PI3K signalling in B- and T-lymphocytes: new developments and therapeutic advances," The Biochemical Journal, 2012, 442(3):465-481.
Garvey, "Rituximab in the treatment of autoimmune haematolgoical disorders," British Journal of Haematology, 2008, 141:149-169.
Gati et al., "(125I)Iodohydroxynitrobenzylthioinosine: a new high-affinity nucleoside transporter probe," Biochemistry and Cell Biology (1987), 65(5):467-473.
Geng et al., "Exploring 9-benzyl purines as inhibitors of glutamate racemase (MurI) in Gram-positive bacteria", Bioorganic & Medicinal Chemistry Letters, 2008, 18(15):4368-4372.
Ghigo et al., "PI3K inhibition in inflammation: Toward tailored therapies for specific diseases," BioEssays, 2010, 32:185-196.
Ghoreschi et al., "Selectivity and therapeutic inhibition of kinases: to be or not to be?" Nature Immunology, Apr. 2009, 10(4):356-360.
Gilani et al., "Overview of the Mutational Landscape in Primary Myelofibrosis and Advances in Novel Therapeutics," Asian Pac J Cancer Prev., Jun. 1, 2019, 20(6):1691-1699.
Godeau et al., "Rituximab efficacy and safety in adult splenectomy candidates with chronic immune thrombocytopenia purpura: results of a prospective multicenter phase 2 study," Blood, 2008, 112(4):999-1004.
Golantsov et al., "Chirally N-substituted indole-2-carbaldehydes. Preparation and use in asymmetric synthesis," Chemistry of Heterocyclic Compounds, 2005, 41(10):1290-1299.
Gopal et al., "PI3Kδ Inhibition by Idelalisib in Patients with Relapsed Indolent Lymphoma," N. Engl. J. Med. 2014, 370(11):1008-1018.
Gopal et al., "Idelalisib for the treatment of non-Hodgkin lymphoma," Expert opinion on pharmacotherapy, 2016, 17(2):265-274.
Granik, "Acetals of lactams and amides of acids. 40. Synthesis and hydrolytic splitting of mono- and bicyclic derivatives of 4-pyrimidinone", Khimiya Geterotsiklicheskikh Soedinenii, 1984, (4):532-537 (with English abstract).

(56) References Cited

OTHER PUBLICATIONS

Graupera et al., "Angiogenesis selectively requires the p110α isoform of PI3K to control endothelial cell migration," Nature, 2008, 453:662.
Greene and Wuts, "Protective Groups in Organic Synthesis," 3rd Ed., Wiley & Sons, Inc., New York, 1999, 799 pages.
Gururajan et al., "Cutting Edge: Constitutive B Cell Receptor Signaling Is Critical for Basal Growth of B Lymphoma," The Journal of Immunology, 2006, 176(10):5715-5719.
Hallek et al., "Guidelines for the diagnosis and treatment of chronic lymphocytic leukemia: a report from the International Workshop on Chronic Lymphocytic Leukemia updating the National Cancer Institute-Working Group 1996 guidelines," Blood, 2008, 111(12):5446-5456.
Hamadani et al., "Allogeneic Stem Cell Transplantation for Patients with Relapsed Chemorefractory Aggressive Non-Hodgkin Lymphomas," Biology of Blood and Marrow Transplantation, 2009, 15(5):547-553.
Harley, "Medical Management of Acute Renal Failure," Renal Failure Replacement Therapies, 2008, pp. 26-32.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 2011, 76:358-372.
Hauser et al., "B-Cell Depletion with Rituximab in Relapsing-Remitting Multiple Sclerosis," The New England Journal of Medicine, 2008, 358(7):676-688.
Hayter and Cook, "Updated assessment of the prevalence, spectrum and case definition of autoimmune disease," Autoimmunity Reviews, 2012, 11:754-765.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-2450.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin, 1982, 30(7):2399-2409.
Hirota, "Efficient synthesis of 2,9-disubstituted 8-hydroxyadenine derivatives", Organic & Biomolecular Chemistry, 2003, 1(8):1354-1365.
Hirsch et al., "Signaling through PI3Kγ: a common platform for leukocyte, platelet and cardiovascular stress sensing," Thrombosis and Haemostasis, 2006, 95(1):29-35.
Hirsch et al., "Taming the PI3K team to hold inflammation and cancer at bay," Pharmacology & Therapeutics, 2008, 118:192-205.
Hosalkar et al., "Skeletal Trauma and Common Orthopedic Problems," Chpt 10, Khurana (ed.) Bone Pathology, 2009, 93 pages.
Huang et al., "Design and synthesis of a pyrido[2,3-d]pyrimidin-5-one class of anti-inflammatory FMS inhibitors,", Bioorganic & Medicinal Chemistry Letters, 2008, 18(7):2355-2361.
Huang et al., "Synthesis and bioassay of a fluorine-containing cytokinin, N6-pentafluoro-benzyladenosine," Youji Huaxue, 1988, 8(2):147-148 (with English abstract).
Ihle et al., "Inhibitors of phosphatidylinositol-3-kinase in cancer therapy", Molecular Aspects of Medicine, 2010, 31(2):135-144.
Indian Office Action in Indian Application No. 2123/DELNP/2014, dated Mar. 8, 2019, 6 pages.
Indonesian Office Action in Indonesian Application No. P00201401236, dated Jan. 15, 2019, 3 pages.
Indonesian Office Action in Indonesian Application No. PID201706041, dated Nov. 14, 2019, 6 pages.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/028915 dated Sep. 17, 2013 (6pgs.).
International Preliminary Report on Patentability for PCT/US2012/030310 dated Oct. 1, 2013 (7pgs.).
International Preliminary Report on Patentability for PCT/US2012/053398, dated Mar. 4, 2014 (6 pgs.).
International Preliminary Report on Patentability in International Application No. PCT/US2014/019372, dated Sep. 1, 2015, 7 pages.
International Preliminary Report on Patentability in International Application No. PCT/US2015/024676, dated Oct. 12, 2016, 11 pages.
International Preliminary Report on Patentability in International Application No. PCT/US2015/035046, dated Dec. 22, 2016, 7 pages.
International Preliminary Report on Patentability in International Application No. PCT/US2016/019741, dated Aug. 29, 2017, 10 pages.
International Preliminary Report on Patentability in International Application No. PCT/US2016/031603, dated Nov. 23, 2017, 7 pages.
International Preliminary Report on Patentability in International Application No. PCT/US2016/031606, dated Nov. 23, 2017, 7 pages.
International Preliminary Report on Patentability in International Application No. PCT/US2016/031611, dated Nov. 23, 2017, 7 pages.
International Search Report and Written Opinion in International Application No. PCT/US2014/019372, dated Apr. 29, 2014, 11 pages.
International Search Report and Written Opinion in International Application No. PCT/US2015/024676, dated Jun. 15, 2015, 18 pages.
International Search Report and Written Opinion in International Application No. PCT/US2015/035046, dated Aug. 27, 2015, 9 pages.
International Search Report and Written Opinion in International Application No. PCT/US2016/019741, dated Aug. 2, 2016, 16 pages.
International Search Report and Written Opinion in International Application No. PCT/US2016/031603, dated Jun. 22, 2016, 11 pages.
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2019/034613, dated Sep. 4, 2019, 19 pages.
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated Jul. 11, 2013 for International Appln. No. PCT/US2013/034803 (15 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).

(56) References Cited

OTHER PUBLICATIONS

International Search Report for PCT/US2011/032213 dated Jun. 14, 2011 (11 pgs.).
Irie, et al., "Discovery of selective and nonpeptidic cathepsin Sinhibitors," Bioorganic & Medicinal Chemistry Letters, 2008, 18(14):3959-3962.
Isobe et al., "Synthesis and Biological Evaluation of Novel 9-Substituted-8-Hydroxyadenine Derivatives as Potent Interferon Inducers", Journal of Medicinal Chemistry, 2006, 49(6):2088-2095.
Israeli Office Action in Israeli Application No. 248,198, dated Jan. 31, 2019, 14 pages.
Israeli Office Action in Israeli Application No. 254,093, dated Jul. 8, 2019, 11 pages.
Israeli Office Action in Israeli Application No. 257,576, dated May 26, 2019, 7 pages.
Israeli Office Action in Israeli Application No. 257,576, Nov. 12, 2019, 8 pages.
Itaya et al., "Syntheses of the marine ascidian purine aplidiamine and its 9-β-D-ribofuranoside," Tetrahedron Letters, 1998, 39(26):4695-4696.
Itaya, et al., "Synthesis and structure of the marine ascidian 8-oxoadenine aplidiamine," Chemical & Pharmaceutical Bulletin, 1999, 47(9):1297-1300.
Iyengar et al., "P110α-mediated constitutive PI3K signaling limits the efficacy of p110δ-selective inhibition in mantle cell lymphoma, particulary with multiple relapse," Blood, 2013, 121(12):2274-2284.
Jackson et al., "PI 3-kinase p110β: a new target for antithrombotic therapy," Nature Medicine, 2005, 11:507-514.
Jager et al., "Molecular recognition analyzed by EPR, ENDOR, and NMR spectroscopy," Angewandte Chemie, International Edition in English, 1996, 35(16):1815-1818.
Jager et al., "Molecular recognition. II Discrimination of specific and non-specific intermolecular interactions by means of magnetic resonance spectroscopy," Magnetic Resonance in Chemistry, 1998, 36(3):205-210.
Japanese Office Action in Japanese Application No. 2014-528654, dated Mar. 29, 2016, 5 pages (English Translation).
Japanese Office Action in Japanese Application No. 2016-561810, dated Dec. 18, 2018, 6 pages.
Japanese Office Action in Japanese Application No. 2017-544953, dated Jan. 7, 2020, 8 pages.
Jimenez et al., "The p85 Regulatory Subunit Controls Sequential Activation of Phosphoinositide 3-Kinase by Tyr Kinases and Ras," J Biol Chem., Nov. 2002, 277(44):41556-41562.
Jordan, "Tamoxifen: a most unlikely pioneering medicine," Nature Reviews: Drug Discovery, 2003, 2:205-213.
Jou et al., "Essential, Nonredundant Role for the Phosphoinositide 3-Kinase p110δ in Signaling by the B-Cell Receptor Complex," Mol Cell Biol. 2002, 22(24):8580-8591.
Kahl et al., "A phase 1 study of the PI3Kδ inhibitor idelalisib in patients with relapsed/refractory mantle cell lymphoma (MCL)," Blood, 2014, 123(22):3398-405.
Kang et al., "Human exposure to bisphenol A," Toxicology, 2006, 226(2-3):79-89.
Kang et al., "Phosphtidylinositol 3-kinase mutations identified in human cancer are oncogenic," Proc Natl Acad Sci U S A., 2005, 102(3):802-807.
Kang et al., "Aplidiamine, a unique zwitterionic benzyl hydroxyadenine from the Western Australian marine ascidian *Aplidiopsis* sp.," Tetrahedron Letters, 1997, 38(6):941-944.
Karpouzas et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009, Philadelphia, PA, pp. S100-S101.
Kasibhatla, "Rationally Designed High-Affinity 2-Amino-6-halopurine Heat Shock Protein 90 Inhibitors That Exhibit Potent Antitumor Activity," Journal of Medicinal Chemistry, 2007, 50(12):2767-2778.

Katritzky et al., "Facile Synthesis of 2-Substituted Indoles and Indolo[3,2-b]carbazoles from 2-(Benzotriazol-1-ylmethyl)indole," Journal of Organic Chemistry, 1995, 60(11):3401-3404.
Kerekes et al., "Aurora Kinase Inhibitors Based on the Imidazo[1,2-a]pyrazine Core: Fluorine and Deuterium Incorporation Improve Oral Absorption and Exposure," J Med Chem., 2011, 54(1):201-210.
Kim et al., "A signaling network in Phenylephrine-Induced Benign Prostatic Hyperplasia," Endocrinology, 2009, 150:3576-3583.
Kim, et al., "A new structural class of S-adenosylhomocysteine hydrolase inhibitors", Bioorganic & Medicinal Chemistry, 2009, 17(18):6707-6714.
Kim, et al., "Synthesis and evaluation of antitumor activity of novel 1,4-naphthoquinone derivatives," Archives of Pharmacal Research, 2006, 29(2):123-130.
Kirkwood et al., "Effect of JAK/STAT or PI3Kδ Plus PD-1 Inhibition on the Tumor Microenvironment: Biomarker Results From a Phase 1b Study in Patients With Advanced Solid Tumors," Presented at the AACR Annual Meetting 2018, Chicago IL, Apr. 14-18, 2018, 2018, Abstract # CT176, 21 pages.
Kitabayashi et al., "The role of interleukin-10 (IL-10) in chronic B-lymphocytic leukemia: IL-10 prevents leukemic cells from apoptotic cell death," Int J Hematol, Aug. 1995, 62(2):99-106.
Klyuchnikov et al., "Allogeneic hematopoietic cell transplantation for diffuse large B cell lymphoma: who, when and how?," Bone Marrow Transplant, 2014, 49(1):1-7.
Knight et al., "A Pharmacological Map of the PI3-K Family Defines a Role for p110α in Insulin Signaling," Cell, 2006, 125(4):733-747.
Knobbe, et al., "Genetic alteration and expression of the phosphoinositol-3-kinase/Akt pathway genes PIK3CA and PIKE in human glioblastomas," Neuropathol Appl Neurobiol., 2005, 31(5):486-90.
Kolasa, et al., "Synthesis of indolylalkoxyiminoalkylcarboxylates as leukotriene biosynthesis inhibitors," Bioorganic & Medicinal Chemistry, 1997, 5(3):507-514.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 9:1734-1740.
Kong and Yamori, "Advances in Development of Phosphatidylinositol 3-Kinase Inhibitors," Current Medicinal Chemistry, 2009, 16:2839-2854.
Korean Office Action in Korean Application No. 10-2019-7028988, dated Dec. 2, 2019, 13 pages.
Kuduk et al., "Heterocyclic fused pyridone carboxylic acid M1 positive allosteric modulators," Bioorganic & Medicinal Chemistry Letters, 2010, 20(8):2533-2537.
Kung et al., "Characterization of a Murine Model of Allergic Pulmonary Inflammation," Int. Arch. Allergy Immunol., 1994, 105(1):83-90.
Kurimoto, et al., "Synthesis and Biological Evaluation of 8-Oxoadenine Derivatives as Toll-like Receptor 7 Agonists Introducing the Antedrug Concept," Journal of Medicinal Chemistry, 2010, 53(7):2964-2972.
Kutney, et al., "Dihydropyridines in synthesis and biosynthesis. IV. Dehydrosecodine, in vitro precursor of indole alkaloids," Canadian Journal of Chemistry, 1982, 60(11):1269-1278.
Lam et al., "Cooperative signaling through the signal transducer and activator of transcription 3 and nuclear factor-κB pathways in subtypes of diffuse large B-cell lymphoma," Blood, 2008, 111(7):3701-3713.
Lampson et al., "Idelalisib given front-line for treatment of chronic lymphocytic leukemia causes frequent immune-mediated hepatotoxicity," Blood, 2016, 128(2):195-203.
Lannutti et al. "CAL-101, a p110δ selective phosphatidylinositol-3-kinsae inhibitor for the treatment of B-cell malignancies, inhibits PI3K signaling and cellular viability," Blood, 2011, 117(2):591-594.
Lech-Maranda E, et. al., "Serum tumor necrosis factor-α and interleukin-10 levels as markers to predict outcome of patients with chronic lymphocytic leukemia in different risk groups defined by the IGHV mutation status," Arch Immunol Ther Exp (Warsz), Dec. 2012, 60(6):477-86.

(56) References Cited

OTHER PUBLICATIONS

Lee, et al., "Inhibition of phosphoinositide 3-kinase δ attenuates allergic airway inflammation and hyperresponsiveness in murine asthma model," FASEB J., 2006, 20(3):455-465.

Li et al., "Design, synthesis and antitumor activities of novel 4-anilino-5H-pyridazino[4,5-b]indoles," Zhongnan Yaoxue, 2008, 6(2):144-148 (English Abstract).

Li et al., "Optimization of the heterocyclic core of the quinazolinone-derived CXCR3 antagonists," Bioorganic & Medicinal Chemistry Letters, 2008, 18(2):688-693.

Li et al., "Synthesis and anti-tumor activities of a novel series of tricyclic 1-anilino-5H-pyridazino[4,5-b]indoles," Archiv der Pharmazie, 2007, 340(8):424-428.

Li et al., "Synthesis and antitumor activities of novel 1-anilino 5H-pyridazino[4,5-b]indoles," Zhongguo Yaowu Huaxue Zazhi, 2007, 17(6):339-343.

Lindsay et al., "SmI2-Promoted Radical Addition Reactions with N-(2-Indolylacyl)oxazolidinones: Synthesis of Bisindole Compounds," Journal of Organic Chemistry, 2007, 72(11):4181-4188.

Link, "The intramolecular Heck reaction," Organic Reactions, John Wiley and Sons Inc., Hoboken, NJ, United States, 2002, 60:157-535.

Lipsky, "Systemic lupus erythematosus: an autoimmune disease of B cell hyperactivity," Nat Immunol., 2001, 2(9):764-766.

Liu et al., "Abstract 4207: JAK inhibition reverses IL10-mediated resistance to B cell receptor (BCR) pathway inhibition in DLBCL," Molecular and Cellular Biology, Oct. 2014, 4 pages.

Liu et al., "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Strategies, 2009, 6:47-55.

Lovric et al., "Rituximab as Rescue Therapy in Anti-Neutrophil Cytoplasmic Antibody-Associated Vasculitis: A Single-Centre Experience With 15 Patients," Nephrol Dial Transplant, 2009, 24(1):179-185.

Lucas, et al., "Rauwolfia alkaloids. XXXI. The synthesis and activity of some reserpine analogs," Journal of the American Chemical Society, 1959, 81:1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga Rhodomela confervoides", Journal of Natural Products, 2007, 70(3):337-341.

Ma, et al., "Two new constituents from Artemisia capillaris Thunb", Molecules, 2008, 13(2):267-271.

Mahboobi, et al., "Bis(1H-2-indolyl)methanones as a Novel Class of Inhibitors of the Platelet-Derived Growth Factor Receptor Kinase," Journal of Medicinal Chemistry, 2002, 45(5):1002-1018.

Malaysian Office Action in Malaysian Application No. PI 2011006255, dated Mar. 15, 2017, 2 pages.

Martelli et al., "Targeting the PI3K/AKT/mTOR signaling network in acute myelogenous leukemia," Expert Opin Investig Drugs. Sep. 2009;18(9):1333-1349.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", J Medicinal Chem., 1975, 18(1):74-9.

Maude et al., "Targeting JAK1/2 and mTOR in murine xenograft models of Ph-like acute lymphoblastic leukemia," Blood, Oct. 2012, 120(17): 3510-3518.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening ," Bioorganic & Medicinal Chemistry Letters (2009), 19(23):6717-6720.

McMahon, G., "VEGF Receptor Signaling in Tumor Angiogenesis," The Oncologist, 2000, 5(1):3-10.

Meade, et al., "Anxiolytic activity of analogs of 4-benzylamino-2-methyl-7H-pyrrolo[2,3-d]pyrimidines," European Journal of Medicinal Chemistry (1998), 33(5):363-374.

Medeot et al., "Rituximab therapy in adult patients with relapsed or refractory immune thrombocytopenia purpura: long-term follow-up results," European Journal of Haematology, 2008, 81:165-169.

Medicinenet.com, "Definition of Cancer," Sep. 18, 2004 [retrieved on Sep. 16, 2005], retrieved from the URL <http://www.medterms.com>, 1 page.

medpagetoday.com, "Current Role of Rituximab in Systematic Lupus," Jan. 2015, [retrieved Apr. 23, 2015], retrieved from the URL <http://www.medpagetoday.com/Rheumatology/Lupus/49398#./49398?&_suid=14297429843880910545130428968​4>, 10 pages.

Meijer et al., "Treatment of primary Sjögren syndrome with rituximab: extended follow-up, safety and efficacy of retreatment," Ann. Rheum. Dis., 2009, 68(2):284-285.

Merriam-Webster.com, "Angiogenesis" Jun. 16, 2014 [retrieved on Sep. 3, 2015], retrieved from URL <www.merriam-webster.com/dictionary/angiogenesis>, 3 pages.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Mexican Office Action in Mexican Application No. MX/a/2016/013182, dated Jul. 30, 2019, 10 pages.

Mexican Office Action in Mexican Application No. MX/a/2017/010918, dated Aug. 19, 2019, 6 pages.

Mexican Office Action in Mexican Application No. MX/a/2017/010918, dated Dec. 17, 2019, 6 pages.

Meyer et al., "Molecular Pathways: Molecular Basis for Sensitivity and Resistance to JAK Kinase Inhibitors," Clin Cancer Res., 2014, 20(8):2051-2059.

Miki, et al., "Reaction of 1-benzylindole-2,3-dicarboxylic anhydride with 3-bromo-4-lithiopyridine: formal synthesis of ellipticine," Heterocycles (1998), 48(8):1593-1597.

Miki, et al., "Reaction of indole-2,3-dicarboxylic anhydride with (3-bromo-4-pyridyl)triisopropoxytitanium: synthesis of ellipticine," Tetrahedron Letters, 1996, 37(43):7753-7754.

Miki, et al., "Synthesis of caulersin and its isomers by reaction of indole-2,3-dicarboxylic anhydrides with methyl indoleacetates," Tetrahedron Letters, 2006, 47(29):5215-5218.

Miki, et al., "Synthesis of ellipticine by reaction of 1-(4-methoxybenzyl)indole-2,3-dicarboxylic anhydride with (3-bromo-4-pyridyl)triisopropoxytitanium," Journal of the Chemical Society, 2001, 18:2213-2216.

Miller et al., "FDA Approval: Idelalisib Monotherapy for the Treatment of Patients with Follicular Lymphoma and Small Lymphocytic Lymphoma," Clin. Cancer Res., 2015, 21(7):1525-1529 (Abstract Only).

Mishra et al., "Decanuclear Copper Framework Supported by a Tripodal Adenine Ligand," Inorganic Chemistry, 2010, 49(8):3691-3693.

Mizoguchi, et al., "Genetic Alterations of Phosphoinositide 3-kinase Subunit Genes in Human Glioblastomas," Brain Pathol. 2004, 14(4):372-377.

Moffett, "Antiulcer agents. p-Aminobenzamido aromatic compounds", Journal of Medicinal Chemistry, 1971, 14(10):963-968.

Mohammadizadeh, et al., "A novel and expedient synthesis of 7-pyrimidinylpyrimido[4,5-d]pyrimidinones," Helvetica Chimica Acta, 2010, 93(1):153-157.

Morales et al., "Epstein-Barr virus infection induces an increase of T regulatory type 1 cells in Hodgkin lymphoma patient," Br J Haematol, Sep. 2014, 166(6):875-90.

Morrison et al., "Pyrimido[4,5-c]pyridazines. 1. Cyclizations with α-keto esters", Journal of Organic Chemistry, 1978, 43(25):4844-4849.

Mukhopadhyay et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," Arkivoc, 2010, 10: 291-304.

(56) References Cited

OTHER PUBLICATIONS

Musmuca et al., "Small-Molecule Interferon Inducers. Toward the Comprehension of the Molecular Determinants through Ligand-Based Approaches", Journal of Chemical Information and Modeling, 2009, 49(7):1777-1786.
Najiwara et al., "Behavior of naphthoyloxyl and methoxynaphthoyloxyl radicals generated from the photocleavage of dinaphthoyl peroxides and 1-(naphthoyloxy)-2-pyridones," Bulletin of the Chemical Society of Japan, 2003, 76(3):575-585.
Najiwara et al., Generation and behavior of naphthoyloxyl radicals in photocleavage of 1-(naphthoyloxy)-2-pyridones, Chemistry Letters, 2001, (10):1064-1065.
Nandagopal & Mehta., "Treatment approaches of hard-to-treat non-Hodgkin lymphomas," Expert Review of Hematology, 2017, 10(3):259-273.
Nettekoven, "A combinatorial approach towards 2-acyl-3-aminoindole derivatives," Tetrahedron Letters, 2000, 41(43):8251-8254.
nlm.nih.gov, "Arthritis: MedlinePlus Medical Encyclopedia," last updated Jan. 22, 2014, [retreived on Oct. 5, 2014], retrieved from URL <http://www.nlm.nih.gove/medlineplus/ency/article/001243.htm>, 5 pages.
nlm.nih.gov, "Autoimmune disorders: MedlinePlus Medical Encyclopedia," last updated Jul. 16, 2013, [retrieved on Oct. 7, 2014] retrieved from URL <http://www.nlm.nih.gov/medlineplus/ency/article/000816.htm>, 4 pages.
Norman, "Selective PI3Kδ inhibitors , a review of the patent literature", Expert Opinion on Therapeutic Patents, Informa Healthcare, 2011, 21(11):1773-1790.
Office Action in CO Application No. 11-179.464, 17 pages.
Office Action in JP Application No. 2014-223540, dated Jul. 21, 2015, 5 pages (with English Translation).
Office Action in JP Application No. 2012-518563, dated Jul. 8, 2014, 6 pages (with English translation).
Office Action in JP Application No. 2013-546274, dated Sep. 15, 2015, 7 pages (with English Translation).
Ogden et al., "Enhanced apoptotic cell clearance capacity and B cell survival factor production by IL-10-activated macrophages: implications for Burkitt's lymphoma," J Immunol, Mar. 1, 2005, 174(5):3015-23.
Oki et al., "Reactivities of Stable Rotamers. XLII. Generation and Fates of Rotameric [1-(9-Fluorenyl)-2-naphthyl]methyl Radicals," Bulletin of the Chemical Society of Japan, 1999, 72(10):2327-2336.
Okkenhaug et al., "Impaired B and T Cell Antigen Receptor Signaling in p110δ PI 3-Kinase Mutant Mice," Science, 2002, 297(5583):1031-1034.
Owen et al., "Response assessment in Waldenstrom macroglobulinaemia: update from the VIth International Workshop," Br J Haematol, 2013, 160(2):171-176.
Park et al., "Homogeneous Proximity Tyrosine Kinase Assays: Scintillation Proximity Assay Versus Homogeneous Time-Resolved Flourescence," Analytical Biochemistry, 1999, 269:94-104.
Park et al., "Phosphoinositide 3-kinase δ inhibitor as a novel therapeutic agent in asthma," Respirology, 2008, 13:764-771.
Patnaik et al., "First-in-human phase I study of copanlisib (BAY 80-6946), an intravenous pan-class I phosphatidylinositol 3-kinase inhibitor, in patients with advanced solid tumors and non-Hodgkin's lymphomas," Annals of Oncology, 2016, 27(10):1928-1940.
Peru Office Action in Peru Application No. 287.14, dated Dec. 14, 2017, 16 pages (English Translation).
Philippine Office Action in Philippine Application No. 1/2017/501766, dated Jul. 29, 2019, 4 pages.
Philippine Office Action in Philippine No. 1/2017/501538, dated Nov. 5, 2019, 4 pages.
Philippine Office Action in Philippine No. 1/2017/501766, dated Jun. 17, 2020, 3 pages.
Phillips et al., "An Ongoing Open-Label Phase 1/2 Study of INCB050465, a Selective PI3K delta Inhibitor, in Patients with Previously Treated B-Cell Malignancies," Blood, 58th Annual Meeting and Exposition of the American-Society-of-Hematology (ASH), Dec. 3-6, 2016, San Diego CA, Dec. 2, 2016, retrieved from URL <http://www.bloodjournal.org/content/128/22/4195>, 128(22):4195.
Phillips et al., "The reaction of anils with 8-quinolinol," Journal of Organic Chemistry, 1954, 19:907-909.
Pinedo and Slamon, "Translational Research: The Role of VEGF in Tumor Angiogenesis," The Oncologist, 2000, 5(1):1-2.
Platts, et al., "A concise synthesis of HIV integrase inhibitors bearing the dipyridone acid motif," Tetrahedron Letters, 2011, 52(4):512-514.
Portnaya, et al., "Azomethine dyes. IV. Indoaniline dyes derived from heterocyclic N-substituted 1-hydroxy-2-naphthamides," Ts. Vses. Nauchn.-Issled. Kinofotoinst. 1960, 40:106-18 (with English abstract).
Prezent et al., STN Abstract, Accession No. 2004:358794, "Boron chelates as intermediates in the synthesis of new functionalized pyridines and pyrimidines from α,α-dioxoketene aminals," Boron Chemistry at the Beginning of the 21st Century, [Proceedings of the International Conference on the Chemistry of Boron], 11th, Moscow, Russian Federation, Jul. 28-Aug. 1, 2002 (2003), Meeting Date 2002, 91-93, (Editor)Bubnov, Nesmeyanov Institute of Organoelement Compounds, Russian Academy of Sciences: Moscow, Russia , 1 page.
Puri and Gold, "Selective inhibitors of phosphoinositide 3-kinase delta: modulators of B-cell function with potential for treating autoimmune inflammatory diseases and B-cell malignancies," Frontiers in Immunology, 2012, 3(256):1-16.
Raedler et al. "Zydelig (Idelalisib): First-in-Class PI3 Kinase Inhibitor Approved for the Treatment of 3 Hematologic Malignancies," Am Health Drug Benefits, 2015, 8(Spec Feature):157-62.
Ramchandren et al., "An Ongoing Phase 1/2 Study 7530 of INCB050465 for Relapsed/Refractory B-Cell Malignancies (CITADEL-101)," Annual Meeting of the American Society of Clinical Oncology, Chicago, IL, dated Jun. 2-6, 2017, Abstract 7530, 1 page.
Ramos-Casals et al., "Rituximab in systemic lupus erythematosus; A systematic review of off-label use in 188 cases," Lupus, 2009, 18:767-776.
Randis, et al., "Role of PI3Kδ and PI3Kδ in inflammatory arthritis and tissue localization of neutrophils," Eur. J. Immunol., 2008, 38(5):1215-1224.
Reich et al., "Preparation of a,b-unsaturated carbonyl compounds and nitriles by selenoxide elimination, " Organic Reactions, vol. 44, John Wiley and Sons, Inc., 1993, 44:1-296.
Remington's Pharmaceutical Sciences, 17th ed., Mack Publishing Company, Easton, Pa., 1985, p. 1418.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan et al., "Identification and biochemical characterization of small-molecule inhibitors of Clostridium botulinum neurotoxin serotype A," Antimicrobial Agents and Chemotherapy, 2009, 53(8):3478-3486.
Sacco et al., "Role of dual PI3/Akt and mTOR inhibition in Waldenstrom's Macroglobulinemia," Oncotarget, 2010, 1(7):578-582.
Sahoo et al., "Antispasmodic compounds. IV," Journal of the Indian Chemical Society, 1959, 36:421-424.
Sako, "Product class 19: pyridopyrimidines," Science of Synthesis, 2004, 16:1155-1267.
Samuels and Ericson, "Oncogenic PI3K and its role in cancer," Curr Opin Oncol., 2006, 18(1):77-82.
Samuels et al., "High Frequency of Mutations of the PIK3CA Gene in Human Cancers," Science, 2004, 304(5670):554.
Sasaki et al., "Function of PI3Kγ in Thymocyte Development, T Cell Activation, and Neutrophil Migration," Science, 2000, 287(5455):1040-1046.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6):445-462.
Schafer and Kolkhof, "Failure is an option: learning from unsuccessful proof-of-concept trials," Drug Discovery Today, Nov. 2008, 13(21/22):913-916.

(56) References Cited

OTHER PUBLICATIONS

Schell et al., "Versatile Solid-Phase Synthesis of Trisubstituted 1H-Pyrido[2,3-d]pyrimidin-4-ones and Related Heterocycles," Journal of Combinatorial Chemistry, 2005, 7(1):96-98.
Segarra et al., "Successful treatment of membranous glomerulonephritis with rituximab in calcineurin inhibitor-dependent patients," Clin J Am Soc Nephrol., 2009, 4(6):1083-1088.
Selig et al., "The application of Stille cross-coupling reactions with multiple nitrogen containing heterocycles," Tetrahedron, Sep. 2011, 67(47):9204-9213.
Sen et al., "Reaction of aldehydes and amines with 8-hydroxyquinaldine and 8-quinolinol. II," Journal of the Indian Chemical Society, 1960, 37:640-642.
Shi et al., "Synthesis and preliminary cytotoxic evaluation of substituted indoles as potential anticancer agents," Chinese Chemical Letters, 2007, 18(8):899-901.
Shreenivas et al., "Emerging Drugs for the Treatment of Myelofibrosis," E Opin on Emerg Drugs., 2018, 23(1):37-49.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 2011, 18:2686-2714.
Singh et al., "Application of Nazarov cyclization to access [6-5-6] and [6-5-5]tricyclic core embedded new heterocycles: an easy entry to structures related to Taiwaniaquinoids," Organic & Biomolecular Chemistry, 2009, 7(9):1858-1867.
Sivina et al., "The bruton tyrosine kinase inhibitor ibrutinib (PCI-32765) blocks hairy cell leukaemia survival, proliferation and B cell receptor signaling: a new therapeutic approach, " Br. J. Haematol., 2014, 166(2):177-188.
Smith et al., "Abstract 434: Upregulated JAK/STAT signaling represents a major mode of resistance to HDAC inhibition in lymphoma and provides a rationale for novel combination therapy," Blood, 2010, 116(21):434.
Sochacki et al., "Therapeutic approaches in myelofibrosis and myelodysplastic/myeloproliferative overlap syndromes," Onco Targets Ther., Apr. 2016, 15(9):2273-2286.
Steliou et al., "Does diatomic sulfur(S2) react as a free species?", Journal of the American Chemical Society, 1992, 114(4):1456-1462.
Sthoeger et al., "Mechanism of autoimmune hemolytic anemia in chronic lymphocytic leukemia," Am J Hematol., Aug. 1993, 43(4):259-264.
STN Search Report, conducted Apr. 2, 2010, 141 pages.
STN Search Report, conducted Apr. 24, 2009, 43 pages.
STN Search Report, conducted Apr. 5, 2010, 513 pages.
STN Search Report, conducted Aug. 29, 2011, 181 pages.
STN Search Report, conducted Aug. 30, 2011, 61 pages.
STN Search Report, conducted Dec. 1, 2010, 132 pages.
STN Search Report, conducted Dec. 16, 2009, 72 pages.
STN Search Report, conducted Dec. 7, 2010, 213 pages.
STN Search Report, conducted May 27, 2009, 2 pages.
STN Search Report, conducted May 28, 2009, 81 pages.
STN Search Report, conducted prior to Jun. 21, 2011, 224 pages.
Stüve et al., "Long-term B-Lymphocyte Depletion With Rituximab in Patients With Relapsing-Remitting Multiple Sclerosis," Arch. Neurol., 2009, 66(2):259-261.
Sujobert et al., "Essential role for the p110δ isoform in phosphoinositide 3-kinase activation and cell proliferation in acute myeloid leukemia," Blood, 2005, 106(3):1063-1066.
Szuecova et al., "Synthesis, characterization and biological activity of ring-substituted 6-benzylamino-9-tetrahydropyran-2-yl and 9-tetrahydrofuran-2-ylpurine derivatives," Bioorganic & Medicinal Chemistry, 2009, 17(5):1938-1947.
Taiwan Notice of Allowance in Taiwan Application No. 107136772, dated Aug. 6, 2019, 5 pages.
Taiwan Office Action in Taiwan Application No. 105111882, dated Mar. 8, 2017, 6 pages (English Translation).
Taiwan Office Action in Taiwan Application No. 108132191, dated Jun. 9, 2020, 7 pages.
Terrier et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009, Philadelphia, PA, p. S100.
Thailand Office Action in Thailand Application No. 1701004896, dated Dec. 11, 2019, 5 pages.
Thomas et al., "Rituximab in relapsed or refractory hairy cell leukemia," Blood, 2003, 102(12):3906-3911.
Thomas et al., "Airway inflammation: chemokine-induced neutrophilia and the class I phosphoinositide 3-kinases," Eur J Immunol. 2005, 35(4):1283-1291.
Tilly et al., "Diffuse large B-cell lymphoma (DLBCL): ESMO Clinical Practice Guidelines for diagnosis, treatment and follow-up," Annals of Oncology, 2015, 26(suppl_5):v116-v125.
Travnickek et al., "2-Chloro-6-[(4-hydroxy-3,5-dimethoxybenzyl)amino]-9-isopropylpurine," Acta Crystallographica, Section E: Structure Reports Online, 2007, E63(2):o728-730.
Uddin et al., "Role of phosphatidylinositol 3'-kinase/AKT pathway in diffuse large B-cell lymphomas survival," Blood, 2006, 108:4178-4186.
Ukraine Office Action in Ukraine Application No. a201709412, dated Oct. 28, 2019, 7 pages.
Umar, "Future directions in cancer prevention," Nature Reviews Cancer, 2012, 12:835-848.
Van Den Neste et al., "Outcome of patients with relapsed diffuse large B-cell lymphoma who fail second-line salvage regimens in the International Coral study," Bone Marrow Transplant, 2016, 51(1):51-57.
Vanhaesebroeck et al., "Signalling by PI3K isoforms: insights from gene-targeted mice," Trends Biochem Sci., 2005, 30(4):194-204.
Vasil'ev et al., "Chelate synthesis of 1-alkyl-5-(trifluoromethyl)-1,6-naphthyridin-4(1H)-ones", Izvestiya Akademii Nauk, Seriya Khimicheskaya, 1994, (8):1510-1511 (with English abstract).
Venet et al., "Lymphocytes in the Development of Lung Inflammation: A role of Regulatory CD4+ T Cells in Indirect Pulmonary Lung Injury," J Immunol., 2009, 183:6472-3480.
Vietnamese Office Action in Vietnamese Application No. 2012-00241, dated May 9, 2017, 3 pages (English Translation).
Vietnamese Office Action in Vietnamese Application No. 2017-03601, dated Nov. 27, 2017, 2 pages (English Translation).
Wallin, "GDC-0980 is a novel class I PI3K/mTOR kinase inhibitor with robust activity in cancer models driven by the PI3K pathway," Molecular cancer therapeutics, 2011, 10.12:2426-2436.
Walsh and Jayne, "Rituximab in the treatment of anti-neutrophil cytoplasm antibody associated vasculitis and systemic lupus erythematosis: past, present and future," Kidney International, 2007, 72:676-682.
Wang et al., "Anticancer drugs of phosphatidylinositol 3 kinase inhibitors," World Notes on Antibiotics, Dec. 2008, 29(5):206-212.
WebMD.com, "Arthritis Health Center: What is Inflammation?" Jul. 6, 2012 [retrieved on Jun. 16, 2014], retrieved from URL <www.webmd.com/arthritis/about-inflammation?page=2>, 4 pages.
Webmd.com, "Bladder Cancer-Prevention," Apr. 30, 2013 [retrieved on Jun. 16, 2014], retrieved from URL <www.webmd.com/cancer/bladder-cancer/bladder-cancer-prevention>, 1 page.
WebMD.com, "Lung Disease Overview," May 23, 2014 [retrieved on Jun. 16, 2014], retrieved from URL <www.webmd.com/lung/lung-diseases-overview>, 3 pages.
Webmd.com, "Osteoarthritis-prevention," Apr. 9, 2013 [retrieved on Jun. 16, 2014], retrieved from URL <www.webmd.com/osteoarthritis/tc/osteoarthritis-prevention>, 2 pages.
WebMD.com, "Psoriasis-prevention," Jan. 9, 2012 [retrieved on Jun. 16, 2014], retrieved from URL <www.webmd.com/skin-problems-and-treatments/psoriasis/psoriasis-prevention>, 1 page.
WebMD.com, Lung Disease & Respiratory Health Center: ARDS, May 21, 2014 [retrieved on ], retrieved from URL <www.webmd.com/lung/ards-acute-respiratory-distress-syndrome?page=2>, 4 pages.
Wiestner et al., "BCR pathway inhibition as therapy for chronic lymphocytic leukemia and lymphoplasmactyic lymphoma," Hematology Am. Soc. Hematol. Educ. Program, 2014, (1):125-34.

(56) References Cited

OTHER PUBLICATIONS

Winkler et al., "TGFB and IL10 have an impact on risk group and prognosis in childhood ALL," Pediatr Blood Cancer, Jan. 2015, 62(1):72-9.
Wudhikarn et al., "Relapse of Lymphoma After Allogeneic Hematopoietic Cell Transplantation: Management Strategies and Outcome," Biology of Blood and Marrow Transplantation, 2011, 17(10):1497-1504.
Wuts and Greene, "Protection for the Amino Group," Protective Groups in Organic Synthesis, 4th ed., John Wiley & Sons: New Jersey, 2007, pp. 696-887.
Xiu et al., "IL-10 induces the development of immunosuppressive CD14(+)HLA-DR(low/−) monocytes in B-cell non-Hodgkin lymphoma," Blood Cancer J., Jul. 31, 2015, 5:e328.
Xu et al., "Activation of the PI3K/AKT/mTOR pathway in diffuse large B cell lymphoma: clinical significance and inhibitory effect of rituximab," Ann Hematol., 2013, 92:1351-1358.
Xu et al., "Design, Synthesis and Biological Evaluation of Deuterated Nintedanib for Improving Pharmacokinetic Properties," J. Label Compd. Radiopharm., 2015, 58(7):308-312.
Yaguchi et al., "Antitumor Activity of ZSTK474, a new Phosphatidinylinositol 3-Kinase Inhibitor," J Natl. Cancer Inst., 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii), 2003, 39(11):1649-1651.
Yahyazadeh et al., "Synthesis of 9-benzyl-6-aminopurines from 5-amino-1-benzyl-4-cyanoimidazoles", Bulletin of the Korean Chemical Society, 2003, 24(12):1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yang et al., "Idelalisib: First-in-Class PI3K Delta Inhibitor for the Treatment of Chronic Lymphocytic Leukemia, Small Lymphocytic Leukemia, and Follicular Lymphoma," Clin Cancer Res., 2015, 21(7):1537-1542 (Abstract Only).
Yanni et al., "Synthesis and biological activity of some 7-substituted aminomethyl-8-hydroxyquinoline-5-sulfonic acids," Indian Journal of Chemistry, Section B: Organic Chemistry Including Medicinal Chemistry, 1982, 21B(7):705-706.
Yanni., "Synthesis of some new 5-iodo-7-substituted-aminomethyl-8-hydroxyquinoline," Revue Roumaine de Chimie, 1994, 39(7):833-836.
Yoo et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," Archives of Pharmacal Research, 2008, 31(2):142-147.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida et al., "MexAB-OprM specific efflux pump inhibitors in Pseudomonas aeruginosa. Part 5: Carbon-substituted analogues at the C-2 position," Bioorganic & Medicinal Chemistry, 2006, 14(6):1993-2004.
Yuan, "PI3K pathway alterations in cancer: variations on a theme," Oncogene, 2008, 27.41:5497-551.
Zak et al. "Discovery and optimization of C-2 methyl imidazopyrrolopyridines as potent and orally bioavailable JAK1 inhibitors with selectivity over JAK," J Med Chem., Jul. 12, 2012, 55(13):6176-6193.
Zhang et al., "Advances in preclinical small molecules for the treatment of NSCLC", Expert Opinion on Therapeutic Patents, 2009, 19(6):731-751.
Zhao and Vogt, "Class I PI3K in oncogenic cellular transformation," Oncogene, 2008, 27:5486-5496.
Zhao et al., "Synthesis and in vitro anti-hepatitis B virus activities of some ethyl 5-hydroxy-1H-indole-3-carboxylates," Bioorganic & Medicinal Chemistry, 2006, 14(8):2552-2558.
International Preliminary Report on Patentability in International Application No. PCT/US2019/034613, dated Dec. 1, 2020, 11 pages.
Rui et al., "Epigenetic gene regulation by Janus kinase 1 in diffuse large B-cell lymphom," PNAS., Nov. 15, 2016, 113(46):E7260-E7267.
Chilean Office Action in Chilean Appln. No. 202003118, dated Nov. 21, 2022, 35 pages (with Machine Translation).
Chinese Office Action in Chinese Appln. No. 201980048918.4, dated Mar. 15, 2023, 17 pages (with English Translation).
Colombian Office Action in Colombian Appln. No. NC2020/0014683, dated Mar. 27, 2023, 6 pages (with English Translation).
Eurasian Notice of Allowance in Eurasian Appln. No. 202092611, dated Apr. 11, 2023, 5 pages (with Machine Translation).
Eurasian Office Action in Eurasian Appln. No. 202390813, dated Apr. 14, 2023, 4 pages (with English Translation).
European Office Action in European U.S. Appl. No. 19/733,240, dated Apr. 24, 2023, 5 pages.
Greenwell et al., "PI3K Inhibitors: Understanding Toxicity Mechanisms and Management," Oncology, 2017, 31(11):821-828.
Israeli Office Action in Israeli Appln. No. 278889, dated Jun. 8, 2023, 4 pages.
Japanese Office Action in Japanese Appln. No. 2020-566893, dated May 30, 2023, 6 pages (with English Translation).
Lampson et al., "PI3Kd-selective and PI3Ka/d-combinatorial inhibitors in clinical development for B-cell non-Hodgkin lymphoma," Expert Opinion on Investigational Drugs, 2017, 26(11):1267-1279.
Malaysian Office Action in Malaysian Appln. No. PI 2020006224, dated Jul. 21, 2023, 4 pages.
Mexican Office Action in Mexican Appln. No. MX/a/2020/012826 dated Sep. 6, 2023, 9 pages (with English Translation).
Ramachandren et al., "Ongoing phase 1/2 study of INCB050465 for relapsed/refractory (R/R) B-cell malignancies (CITADEL-101)," Journal of Clinical Oncology, 2017, 35(15):7530 (Abstract Only).
Thai Office Action in Thai Appln. No. 2001006823, dated Mar. 27, 2023, 10 pages (with English Translation).
Ukrainian Office Action in Ukrainian Appln. No. a202007595, dated Apr. 28, 2023, 11 pages (with English Translation).
Ukrainian Office Action in Ukrainian Appln. No. a202007595, dated Aug. 23, 2023, 9 pages (with English Translation).
Chilean Office Action in Chilean Application No. 202003118, Nov. 10, 2023, 32 pages (with Machine Translation).
Chinese Office Action in Chinese Application No. 201980048918.4, dated Dec. 21, 2023, 21 pages (with English Translation).
Eurasian Office Action in Eurasian Application No. 202390813, dated Nov. 22, 2023, 8 pages (with Machine Translation).
Australian Office Action in Australian Application No. 2019277560, dated Apr. 17, 2024, 4 pages.
Eurasian Office Action in Eurasian Application No. 202390813, dated Jul. 1, 2024, 2 pages (with Machine Translation).
Israeli Office Action in Israeli Application No. 278889, dated Jun. 18, 2024, 3 pages.
Mexican Office Action in Mexican Application No. MX/a/2020/012826, dated Feb. 22, 2024, 8 pages (with English Translation).
Peruvian Office Action in Peruvian Application No. 1922-2020, dated May 31, 2024, 8 pages (with English Translation).
Taiwanese Office Action in Taiwanese Application No. 108118995, dated Dec. 13, 2023, 8 pages (with English Translation).

* cited by examiner

DOSING REGIMEN FOR THE TREATMENT OF PI3K RELATED DISORDERS

TECHNICAL FIELD

The present application provides methods of treating PI3Kδ related disorders using pyrazolopyrimidine derivatives.

BACKGROUND

Constitutive signaling through the B-cell receptor (BCR) plays a critical role in the pathogenesis of human B-cell malignancies (Gururajan M. et al, *The Journal of Immunology*, 2006; 176(10):5715-5719) and leads to downstream activation of class I phosphatidylinositol 3-kinases (PI3Ks) (Benschop Cambier J. C., *Current Opinion in Immunology*, 1999; 11(2):143-151; So L., Fruman D. A. *The Biochemical Journal*, 2012; 442(3):465-481). Class I PI3Ks are heterodimeric lipid kinases composed of a regulatory (p85 or p101) and a catalytic (p110) subunit (Chalhoub N. et al, *Annual review of pathology*, 2009; 4:127-150). Each of the 4 tissue-specific p110 subunit isoforms (Class IA: α, β, and δ; Class IB: γ) confers unique physiologic functions on the corresponding PI3K isoforms, including insulin signaling and angiogenesis (PI3Kα) (Foukas L. C. et al, *Nature*, 2006; 441:366; Knight Z. A. et al, *Cell*, 2006; 125(4):733-747; and Graupera M. et al, *Nature*, 2008; 453:662), platelet function and thrombosis (PI3Kβ) (Jackson S. P. et al, *Nature Medicine*, 2005; 11:507), and white blood cell function and inflammation (PI3Kγ) (Hirsch E. et al, *Thrombosis and Haemostasis*, 2006; 95(1):29-35). The PI3Kδ isoform functions as a critical node in signaling networks that regulate B-cell growth and survival, and its aberrant activation is a key event in malignant transformation of B-cells (Kang S. et al, *Proceedings of the National Academy of Sciences of the United States of America*, 2005; 102(3):802-807; Puri K. D., Gold M. R., *Frontiers in Immunology*, 2012; 3:256). Substantial interconnectivity exists between BCR and PI3Kδ-mediated signaling networks and other networks important for regulating B-cell survival and proliferation, including the Janus kinase-signal transducer and activator of transcription (JAK/STAT) pathway (Lam L. T., et al, *Blood*, 2008; 111 (7):3701-3713; Rui L. et al, *Proceedings of the National Academy of Sciences*, 2016; 113 (46): E7260-E7267), suggesting potential additive or synergistic therapeutic effects in B-cell malignancies.

Prognosis for patients with relapsed or refractory B-cell non-Hodgkin lymphoma (NHL) is generally poor. For example, the 5-year overall survival (OS) rate for patients with relapsed follicular lymphoma (FL), the most common indolent NHL subtype, is only 50% (Casulo C. et al, *Journal of Clinical Oncology*, 2015; 33(23):2516-2522). Prognosis is worse for patients with relapsed aggressive NHL subtypes, with a median survival of 3.6 and 4.4 months among patients with relapsed diffuse large B-cell lymphoma (DLBCL) who had failed first-line and second-line salvage regimens, respectively (Van Den Neste E. et al, *Bone Marrow Transplant*, 2016; 51(1):51-57). Current guidelines for the treatment for relapsed B-cell NHL differ according to subtype and include chemo- or radio-immunotherapy, targeted therapies with small-molecule kinase inhibitors, or immunomodulatory therapies (NCCN Clinical Practice Guidelines in Oncology (NCCN Guidelines®). B-cell Lymphomas. Version 7.2017; 2017; Tilly H. et al, *Annals of Oncology*, 2015; 26 (suppl_5): v116-v125; Dreyling M. et al, *Annals of Oncology*, 2016; 27 (suppl_5): v83-v90; Dreyling M. et al, *Annals of Oncology*, 2017; 28 (suppl_4): iv62-iv71). In addition to systemic therapy, autologous or allogeneic stem cell transplant (SCT) is often used to treat patients with relapsed B-cell NHL and allogeneic SCT is considered the only curative option for these patients (Wudhikarn K. et al *Biology of Blood and Marrow Transplantation*, 2011; 17(10):1497-1504; Avivi I., et al, *British Journal of Haematology*, 2009; 147(5):719-728; Klyuchnikov E., et al, *Bone Marrow Transplant*, 2014; 49(1):1-7; Hamadani M. et al, *Biology of blood and marrow transplantation: journal of the American Society for Blood and Marrow Transplantation*. 2009; 15(5):547-553).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455): 1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-1pr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011): 1007-11; Lee, et al., FASEB J. 2006, 20(3):455-65) and to have attenuated disease in a model of RA (Randis, et al., Eur. J. Immunol., 2008, 38(5):1215-24).

B cell proliferation has shown to play a major role in the development of inflammatory autoimmune diseases (Puri, Frontiers in Immunology (2012), 3(256), 1-16; Walsh, Kidney International (2007) 72, 676-682). For example, B cells support T-cell autoreactivity, an important component of inflammatory autoimmune diseases. Once activated and matured, B cells can traffic to sites of inflammation and recruit inflammatory cells or differentiate to plasmablasts. Thus, activity of B-cells can be affected by targeting B-cell stimulatory cytokines, B-cell surface receptors, or via B-cell depletion. Rituximab—an IgG1 κ mouse/human chimeric monoclonal antibody directed against the B-cell surface receptor CD20—has been shown to deplete CD20+ B cells. Use of rituximab has been shown to have efficacy in treating idiopathic thrombocytopenic purpura, autoimmune hemolytic anemia, or vasculitis. For example, treatment with rituximab resulted in remission of the disease in patients suffering from anti-neutrophil cytoplasm antibody associated (ANCA) systemic vasculitis (AASV) with demonstrated peripheral B-cell depletion (Walsh, 2007; Lovric, Nephrol Dial Transplant (2009) 24: 179-185). Similarly, a complete response was reported in one-third to two-thirds of patients having mixed cryoglobulinemia vasculitis after treatment with rituximab, including patients who presented with a severe form of vasculitis that was resistant or intolerant to other treatments (Cacoub, Ann Rheum Dis 2008; 67:283-287). Similarly, rituximab has been shown to have efficacy in treating patients with idiopathic thrombocytopenic purpura (or immune thrombocytopenic purpura) (Garvey, British Journal of Haematology, (2008) 141, 149-169; Godeau, Blood (2008), 112(4), 999-1004; Medeo, European Journal of Haematology, (2008) 81, 165-169) and autoimmune hemolytic anemia (Garvey, British Journal of Haematology, (2008) 141, 149-169).

PI3Kδ signaling has been tied to B cell survival, migration, and activation (Puri, *Frontiers in Immunology*, 2012, 3(256), 1-16, at pages 1-5; and Clayton, *J Exp Med*, 2002, 196(6):753-63). For example, PI3Kδ is required for antigen-dependent B-cell activation driven by B cell receptor. By blocking B-cell adhesion, survival, activation, and proliferation, PI3Kδ inhibition can impair the ability of B cells to activate T cells, preventing their activation and reducing secreation of autoantibodies and pro-inflammatory cytokines. Hence, by their ability to inhibit B cell activation, PI3Kδ inhibitors would be expected to treat B cell mediated diseases that were treatable by similar methods such as B cell depletion by rituximab. Indeed, PI3Kδ inhibitors have been shown to be useful mouse models of various autoimmune diseases that are also treatable by rituximab such as arthritis (Puri (2012)). Further, innate-like B cells, which are linked to autoimmunity are sensitive to PI3Kδ activity, as MZ and B-1 cells are nearly absent in mice lacking the p110δ gene (Puri (2012). PI3Kδ inhibitors can reduce trafficking of and activation of MZ and B-1 cells, which are implicated in autoimmune diseases.

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3):802-7; Bader, et al., Proc Natl Acad Sci USA. 2006, 103(5):1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3):1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol Appl Neurobiol. 2005, 31(5):486-90). Further, these isoforms have all been shown to be oncogenic in cell culture (Kang, et al., 2006).

The introduction of rituximab improved treatment outcomes for patients with B-cell NHL (Chao M. P., *Cancer Management and Research*. 2013; 5:251-269; Nandagopal L., Mehta A., *Expert Review of Hematology*, 2017; 10(3): 259-273). For patients who experience rituximab resistance and/or relapsed or refractory disease, the PI3K inhibitor class has shown promise, but clinical use has been limited by toxicities. For example, the first-in-class PI3Kδ-selective inhibitor, idelalisib, has been associated with considerable toxicity, including hepatotoxicity (Coutré S. E., et al, *Leukemia & Lymphoma*, 2015; 56(10):2779-2786; Gopal A., Graf S., *Expert opinion on pharmacotherapy*, 2016; 17(2): 265-274), as well as increased risk of opportunistic infection (Lampson B. L. et al, *Blood*, 2016; 128(2):195-203), and requires frequent monitoring. Likewise, treatments targeting other PI3K isoforms have corresponding risks (e.g., hyperglycemia and hypertension) (Burris H. A., et al, *Journal of Clinical Oncology*, 2014; 32 (15_suppl): 2513-2513; ALIQOPA™. (copanlisib) for injection, for intravenous use. U.S. Whippany, NJ: Bayer HealthCare Pharmaceuticals Inc.; 2017; Patnaik A. et al, *Annals of Oncology*, 2016; 27(10): 1928-1940; Dreyling M. et al, *Journal of Clinical Oncology*, 2017; 35(35):3898-3905). Therefore, an unmet need remains for effective therapies with improved safety profiles in this difficult-to-treat patient population.

SUMMARY OF THE INVENTION

The present application provides, inter alia, a method of treating a disease in a patient, wherein said disease is associated with abnormal expression or activity of PI3Kδ kinase, the method comprising:
  i) administering to the patient an inhibitor of PI3Kδ in a first dosage that is about 3 mg/day to about 50 mg/day for a first period of time which is about 2 weeks to about 12 weeks; and
  ii) administering to the patient a second dosage of the inhibitor of PI3Kδ which is less than the first dosage administered at the end of the first time period and which is:
    (a) about 2.5 mg/day or less; or
    (b) about 50 mg/week or less;
and wherein the second dosage is administered for a second period of time which occurs after the first period of time.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A: PK of Compound 1C dosing. FIG. 1B: Dose-response relationship of Compound 1C AUC. AUC, area under the curve; $AUC_{0-T}$, area under the plasma concentration-time curve; $IC_{50}$, half maximal inhibitory concentration; $IC_{90}$, 90% maximal inhibitory concentration; PK, pharmacokinetics; QD, once daily.

DETAILED DESCRIPTION

Figure 1A:
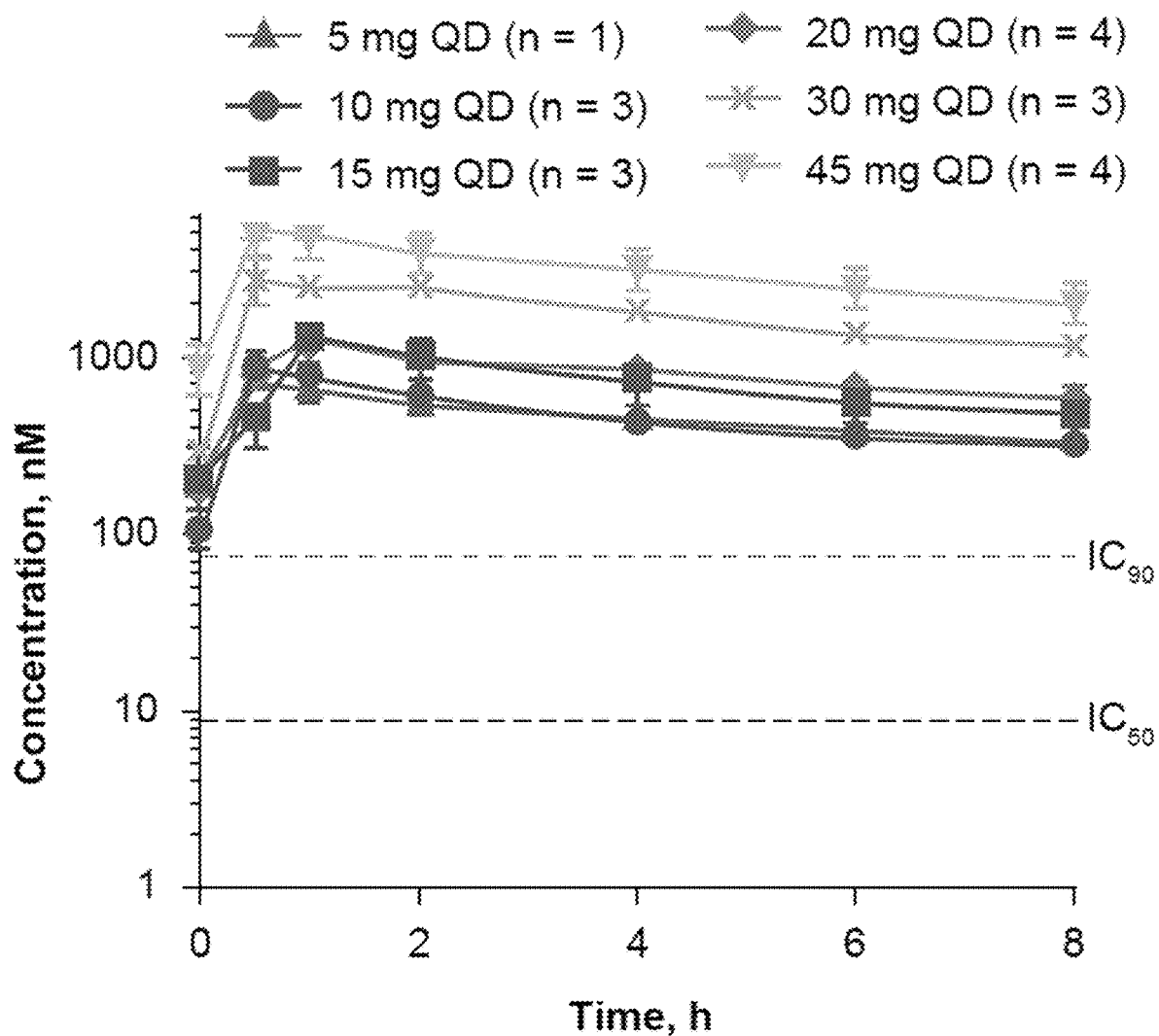
FIGS. 1A-1B show PK of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt (i.e., Compound 1C) at steady state.

The present application provides methods of treating a disease in a patient, wherein said disease is associated with abnormal expression or activity of PI3Kδ kinase, the method comprising:
i) administering to the patient an inhibitor of PI3Kδ in a first dosage that is about 3 mg/day to about 50 mg/day for a first period of time which is about 2 weeks to about 12 weeks; and
ii) administering to the patient a second dosage of the inhibitor of PI3Kδ which is less than the first dosage administered at the end of the first time period and which is:
(a) about 2.5 mg/day or less; or
(b) about 50 mg/week or less;
and wherein the second dosage is administered for a second period of time which occurs after the first period of time.

The present application further provides methods of treating a disease in a patient, wherein said disease is associated with abnormal expression or activity of PI3Kδ kinase, the method comprising:
i) administering to the patient an inhibitor of PI3Kδ in a first dosage that is about 3 mg/day to about 50 mg/day for a first period of time which is about 2 weeks to about 12 weeks; and
ii) administering to the patient a second dosage of the inhibitor of PI3Kδ which is less than the first dosage administered at the end of the first time period and which is about 7.5 mg/day or less; and wherein the second dosage is administered for a second period of time which occurs after the first period of time.

As used herein, the term "first period of time" refer to a period of time of administration of the first dosage of the inhibitor of PI3Kδ to the patient.

In some embodiments, the first period of time begins at the time of initial administration of the first dosage of the inhibitor of PI3Kδ to the patient.

As used herein, the term "second period of time" refer to a period of time of administration of the second dosage of the inhibitor of PI3Kδ to the patient.

In some embodiments, the second period of time begins at the time of initial administration of the second dosage of the inhibitor of PI3Kδ to the patient.

In some embodiments, the time of initial administration of the second dosage of the inhibitor of PI3Kδ to the patient (i.e., the start of the second period of time) is within 2 weeks of the end of the first period of time, for example, within 1 week, within 6 days, within 5 days, within 4 days, within 3 days, within 2 days, or within 1 days of the end of the first period of time.

In some embodiments, the second period of time is continued for any amount of time, for example, until the treatment is terminated.

In some embodiments, each of the first dosages is administered as a single, once daily dosage.

In some embodiments, each of the first dosages is administered as a single, once daily oral dosage.

In some embodiments, the first dosage is about 5 mg/day to about 50 mg/day, for example, about 5 mg/day to about 40 mg/day, about 5 mg/day to about 30 mg/day, about 5 mg/day to about 20 mg/day, about 5 mg/day to about 10 mg/day, about 10 mg/day to about 40 mg/day, about 10 mg/day to about 30 mg/day, about 10 mg/day to about 20 mg/day, about 20 mg/day to about 40 mg/day, about 20 mg/day to about 30 mg/day, or about 20 mg/day to about 40 mg/day.

In some embodiments, the first dosage is about 50 mg/day, about 45 mg/day, about 40 mg/day, about 30 mg/day, about 20 mg/day, about 15 mg/day, about 10 mg/day, or about 5 mg/day.

In some embodiments, the first dosage is about 18 mg/day to about 22 mg/day.

In some embodiments, the first dosage is about 18 mg/day to about 22 mg/day and is administered as a single, once daily (i.e., QD) dosage.

In some embodiments, the first dosage is about 18 mg/day to about 22 mg/day and is administered as a single, once daily (i.e., QD) oral dosage.

In some embodiments, the first dosage is about 20 mg/day.

In some embodiments, the first dosage is about 20 mg/day and is administered as a single, once daily (i.e., QD) dosage.

In some embodiments, the first dosage is about 20 mg/day and is administered as a single, once daily (i.e., QD) oral dosage.

In some embodiments, the first dosage is about 10 mg/day.

In some embodiments, the first dosage is about 10 mg/day and is administered as a single, once daily (i.e., QD) dosage.

In some embodiments, the first dosage is about 10 mg/day and is administered as a single, once daily (i.e., QD) oral dosage.

In some embodiments, the first period of time is about 3 weeks to about 11 weeks, for example, about 8 weeks to about 12 weeks, about 4 weeks to about 10 weeks, about 5 weeks to about 9 weeks, or about 8 weeks to about 9 weeks.

In some embodiments, the first period of time is about 2 weeks, about 3 weeks, about 4 weeks, about 5 weeks, about 6 weeks, about 7 weeks, about 8 weeks, about 9 weeks, about 10 weeks, about 11 weeks, or about 12 weeks.

In some embodiments, the first period of time is about 8 weeks to about 9 weeks.

In some embodiments, the first period of time is about 8 weeks.

In some embodiments, the first period of time is about 9 weeks.

In some embodiments, the first dosage is reduced during the first period of time.

In some embodiments, the first dosage is reduced from the about 3 mg/day to about 50 mg/day to about 3 mg/day to about 30 mg/day, about 3 mg/day to about 20 mg/day, about 3 mg/day to about 15 mg/day, about 3 mg/day to about 10 mg/day, about 3 mg/day to about 7 mg/day, or about 3 mg/day to about 5 mg/day.

In some embodiments, the first dosage is reduced from the about 3 mg/day to about 50 mg/day to about 3 mg/day to about 7 mg/day during the first period of time.

In some embodiments, the first dosage is reduced from about 50 mg/day to about 30 mg/day, about 20 mg/day, about 15 mg/day, about 10 mg/day, about 5 mg/day, about 2 mg/day, or about 1 mg/day, during the first period of time.

In some embodiments, the first dosage is reduced from about 20 mg/day to about 15 mg/day, about 10 mg/day, about 5 mg/day, about 2 mg/day, or about 1 mg/day, during the first period of time.

In some embodiments, each of the second dosages is administered as a single, once daily (QD) dosage or as a single, once weekly (QW) dosage.

In some embodiments, each of the second dosages is administered as a single, once daily (QD) dosage.

In some embodiments, each of the second dosages is administered as a single, once weekly (QW) dosage.

In some embodiments, each of the second dosages is administered as a single, once daily (QD) oral dosage or as a single, once weekly (QW) oral dosage.

In some embodiments, each of the second dosages is administered as a single, once daily (QD) oral dosage.

In some embodiments, each of the second dosages is administered as a single, once weekly (QW) oral dosage.

In some embodiments, the second dosage is about 5.0 mg/day or less, for example, about 5.0 mg/day, about 4.0 mg/day, about 3.0 mg/day, about 2.5 mg/day, about 2.0 mg/day, about 1.75 mg/day about 1.5 mg/day, about 1.25 mg/day, or about 1.0 mg/day.

In some embodiments, the second dosage is about 2.5 mg/day to about 7.5 mg/day.

In some embodiments, the second dosage is about 3.0 mg/day to about 7.0 mg/day.

In some embodiments, the second dosage is about 4.0 mg/day to about 6.0 mg/day.

In some embodiments, the second dosage is about 5.0 mg/day.

In some embodiments, the second dosage is about 4.0 mg/day to about 6.0 mg/day and is administered as a single, once daily (QD) dosage.

In some embodiments, the second dosage is about 5.0 mg/day and is administered as a single, once daily (QD) dosage.

In some embodiments, the second dosage is about 4.0 mg/day to about 6.0 mg/day and is administered as a single, once daily (QD) oral dosage.

In some embodiments, the second dosage is about 5.0 mg/day and is administered as a single, once daily (QD) oral dosage.

In some embodiments, the second dosage is reduced from about 5.0 mg/day or less during the second period of time.

In some embodiments, the second dosage is reduced from about 5.0 mg/day or less to about 2.5 mg/day or less, 2.0 mg/day or less, about 1.75 mg/day, or less about 1.5 mg/day or less, about 1.25 mg/day or less, or about 1.0 mg/day or less during the second period of time.

In some embodiments, the second dosage is reduced from about 5.0 mg/day to about 2.5 mg/day, 2.0 mg/day, about 1.75 mg/day, about 1.5 mg/day, about 1.25 mg/day, or about 1.0 mg/day during the second period of time In some embodiments, the second dosage is reduced from the about 5.0 mg/day to about 0.75 mg/day to about 1.25 mg/day during the second period of time.

In some embodiments, the second dosage is reduced from about 5.0 mg/day to about 1.25 mg/day during the second period of time.

In some embodiments, the second dosage is reduced from about 5.0 mg/day to about 2.0 mg/day, about 1.5 mg/day, about 1.25 mg/day, or about 1.0 mg/day.

In some embodiments, the second dosage is reduced from about 5.0 mg/day to about 1.0 mg/day. In some embodiments, the second dosage is about 2.5 mg/day or less, for example, about 2.5 mg/day, about 2.0 mg/day, about 1.75 mg/day about 1.5 mg/day, about 1.25 mg/day, or about 1.0 mg/day.

In some embodiments, the second dosage is about 1.0 mg/day to about 2.5 mg/day, for example, about 1.0 mg/day to about 2.0 mg/day, about 1.0 mg/day to about 1.5 mg/day, or about 1.0 mg/day to about 1.25 mg/day.

In some embodiments, the second dosage is about 2 mg/day to about 2.5 mg/day.

In some embodiments, the second dosage is about 2.5 mg/day.

In some embodiments, the second dosage is about 2 mg/day to about 2.5 mg/day and is administered as a single, once daily (QD) dosage.

In some embodiments, the second dosage is about 2.5 mg/day and is administered as a single, once daily (QD) dosage.

In some embodiments, the second dosage is about 2 mg/day to about 2.5 mg/day and is administered as a single, once daily (QD) oral dosage.

In some embodiments, the second dosage is about 2.5 mg/day and is administered as a single, once daily (QD) oral dosage.

In some embodiments, the second dosage is reduced from about 2.5 mg/day or less during the second period of time.

In some embodiments, the second dosage is reduced from about 2.5 mg/day or less to about 2.0 mg/day or less, about 1.75 mg/day or less, about 1.5 mg/day or less, about 1.25 mg/day or less, or about 1.0 mg/day or less during the second period of time.

In some embodiments, the second dosage is reduced from about 2.5 mg/day to about 2.0 mg/day, about 1.75 mg/day, about 1.5 mg/day, about 1.25 mg/day, or about 1.0 mg/day during the second period of time.

In some embodiments, the second dosage is reduced from about 2.5 mg/day to about 1.25 mg/day during the second period of time.

In some embodiments, the second dosage is reduced from about 2.5 mg/day to about 2.0 mg/day, about 1.5 mg/day, about 1.25 mg/day, or about 1.0 mg/day.

In some embodiments, the second dosage is reduced from about 2.5 mg/day to about 1.0 mg/day.

In some embodiments, the reduced dosage of the second dosage is administered as a single, once daily (QD) dosage.

In some embodiments, the reduced dosage of the second dosage is administered as a single, once daily (QD) oral dosage.

In some embodiments, the second dosage is about 50 mg/week or less, for example, about 40 mg/week or less, about 30 mg/week or less, about 20 mg/week or less, about 10 mg/week or less, about 5 mg/week or less, about 2 mg/week or less, or about 1 mg/week or less.

In some embodiments, the second dosage is about 5 mg/week to about 50 mg/week, for example, about 5 mg/week to about 40 mg/week, about 5 mg/week to about 30 mg/week, about 5 mg/week to about 20 mg/week, about 5 mg/week to about 10 mg/week, about 10 mg/week to about 40 mg/week, about 10 mg/week to about 30 mg/week, about 10 mg/week to about 20 mg/week, about 20 mg/week to about 40 mg/week, about 20 mg/week to about 30 mg/week, or about 30 mg/week to about 40 mg/week.

In some embodiments, the second dosage is about 18 mg/week to about 20 mg/week.

In some embodiments, the second dosage is about 20 mg/week.

In some embodiments, the second dosage is about 18 mg/week to about 20 mg/week and is administered as a single, once weekly (QW) dosage.

In some embodiments, the second dosage is about 20 mg/week and is administered as a single, once weekly (QW) dosage.

In some embodiments, the second dosage is reduced from about 50 mg/week or less during the second period of time.

In some embodiments, the second dosage is reduced from about 50 mg/week or less to about 40 mg/week or less, about 30 mg/week or less, about 20 mg/week or less, about 10 mg/week or less, about 5 mg/week or less, about 2 mg/week or less, or about 1 mg/week or less during the second period of time.

In some embodiments, the second dosage is reduced from about 5 mg/week to about 50 mg/week, to about 5 mg/week to about 40 mg/week, about 5 mg/week to about 30 mg/week, about 5 mg/week to about 20 mg/week, about 5 mg/week to about 10 mg/week, about 10 mg/week to about 40 mg/week, about 10 mg/week to about 30 mg/week, about 10 mg/week to about 20 mg/week, about 20 mg/week to about 40 mg/week, about 20 mg/week to about 30 mg/week, or about 30 mg/week to about 40 mg/week during the second period of time.

In some embodiments, the second dosage is reduced from about 50 mg/week, to about 40 mg/week, about 30 mg/week, about 20 mg/week, about 10 mg/week, or about 5 mg/week during the second period of time.

In some embodiments, the second dosage is reduced from about 20 mg/week to about 10 mg/week during the second period of time.

In some embodiments, the second dosage is reduced from about 20 mg/week to about 10 mg/week during the second period of time.

In some embodiments, the second dosage is reduced from about 10 mg/week to about 5 mg/week during the second period of time.

In some embodiments, the reduced dosage of the second dosage is administered as a single, once weekly (QW) dosage.

In some embodiments, the patient has been identified as exhibiting one or more symptoms associated with one or more treatment-emergent adverse events (TEAEs). As used herein, the severity of TEAEs described herein were assessed using Common Terminology Criteria for Adverse Events version 4.03, the disclosure of which is incorporated herein by reference in its entirety.

In some embodiments, the patient has been identified as exhibiting the one or more symptoms associated with one or more treatment-emergent adverse events (TEAEs) during the first period of time.

In some embodiments, the first dosage is reduced from about 3 mg/day to about 50 mg/day to about 3 mg/day to about 30 mg/day, about 3 mg/day to about 20 mg/day, about 3 mg/day to about 15 mg/day, about 3 mg/day to about 10 mg/day, about 3 mg/day to about 7 mg/day, or about 3 mg/day to about 5 mg/day when the patient has been identified as exhibiting the one or more symptoms associated with one or more treatment-emergent adverse events (TEAEs).

In some embodiments, the first dosage is reduced from about 50 mg/day to about 30 mg/day, about 20 mg/day, about 15 mg/day, about 10 mg/day, about 5 mg/day, about 2 mg/day, or about 1 mg/day, during the first period of time when the patient has been identified as exhibiting the one or more symptoms associated with one or more treatment-emergent adverse events (TEAEs).

In some embodiments, the first dosage is reduced from about 20 mg/day to about 15 mg/day, about 10 mg/day, about 5 mg/day, about 2 mg/day, or about 1 mg/day, during the first period of time when the patient has been identified as exhibiting the one or more symptoms associated with one or more treatment-emergent adverse events (TEAEs).

In some embodiments, the first dosage is reduced from about 20 mg/day to about 10 mg/day when the patient has been identified as exhibiting the one or more symptoms associated with one or more treatment-emergent adverse events (TEAEs).

In some embodiments, the first dosage is reduced from about 20 mg/day to about 5 mg/day when the patient has been identified as exhibiting the one or more symptoms associated with one or more treatment-emergent adverse events (TEAEs).

In some embodiments, the first dosage is reduced from about 10 mg/day to about 5 mg/day when the patient has been identified as exhibiting the one or more symptoms associated with one or more treatment-emergent adverse events (TEAEs).

In some embodiments, the methods provided herein further comprise stopping administration of the first dosage when the patient has been identified as exhibiting the one or more symptoms associated with one or more treatment-emergent adverse events (TEAEs).

In some embodiments, the patient has been identified as exhibiting the one or more symptoms associated with one or more treatment-emergent adverse events (TEAEs) during the second period of time.

In some embodiments, the second dosage is reduced from about 3 mg/day to about 50 mg/day to about 3 mg/day to about 30 mg/day, about 3 mg/day to about 20 mg/day, about 3 mg/day to about 15 mg/day, about 3 mg/day to about 10 mg/day, about 3 mg/day to about 7 mg/day, or about 3 mg/day to about 5 mg/day during the second period of time when the patient has been identified as exhibiting the one or more symptoms associated with one or more treatment-emergent adverse events (TEAEs).

In some embodiments, the second dosage is reduced from about 50 mg/week, to about 40 mg/week, about 30 mg/week, about 20 mg/week, about 10 mg/week, about 5 mg/week, about 2 mg/week or about 1 mg/week during the second period of time when the patient has been identified as exhibiting the one or more symptoms associated with one or more treatment-emergent adverse events (TEAEs).

In some embodiments, the second dosage is reduced from about 50 mg/week or less to about 40 mg/week or less, about 30 mg/week or less, about 20 mg/week or less, about 10 mg/week or less, about 5 mg/week or less, about 2 mg/week or less, or about 1 mg/week or less during the second period of time during the second period of time when the patient has been identified as exhibiting the one or more symptoms associated with one or more treatment-emergent adverse events (TEAEs).

In some embodiments, the second dosage is reduced from about 20 mg/week to about 10 mg/week or less during the second period of time during the second period of time when the patient has been identified as exhibiting the one or more symptoms associated with one or more treatment-emergent adverse events (TEAEs).

In some embodiments, the second dosage is reduced from about 20 mg/week to about 5 mg/week or less during the second period of time during the second period of time when the patient has been identified as exhibiting the one or more symptoms associated with one or more treatment-emergent adverse events (TEAEs).

In some embodiments, the second dosage is reduced from about 10 mg/week to about 5 mg/week or less during the second period of time during the second period of time when the patient has been identified as exhibiting the one or more symptoms associated with one or more treatment-emergent adverse events (TEAEs).

In some embodiments, the one or more treatment-emergent adverse events comprise one or more of diarrhea/colitis, nausea, fatigue, rash, neutropenia, pyrexia, hypotension, sepsis, respiratory failure, pneumonitis, pneumonia, hypertension, hyperglycemia, abdominal pain, bronchitis, dehydration, thrombocytopenia, cough, vomiting, decreased appetite, increased lacrimation, oral herpes, tachycardia, spinal cord compression, intractable pain, elevated alkaline phosphatase, elevated transaminase, hyperlipidemia, hypercalcemia, dizziness, alopecia, constipation, fluid overload, headache, hypokalemia, night sweats, encephalopathy, atrial flutter, atrial fibrillation, and dyspnea.

In some embodiments, the symptoms associated with the one or more treatment-emergent adverse events are symptoms associated with one or more of diarrhea/colitis, nausea, fatigue, rash, neutropenia, pyrexia, hypotension, sepsis, respiratory failure, pneumonitis, pneumonia, hypertension, hyperglycemia, abdominal pain, bronchitis, dehydration, thrombocytopenia, cough, vomiting, decreased appetite, increased lacrimation, oral herpes, tachycardia, spinal cord compression, intractable pain, elevated alkaline phosphatase, elevated transaminase, hyperlipidemia, hypercalcemia, dizziness, alopecia, constipation, fluid overload, headache, hypokalemia, night sweats, encephalopathy, atrial flutter, atrial fibrillation, and dyspnea.

In some embodiments, the one or more treatment-emergent adverse events comprise one or more of diarrhea/colitis, nausea, fatigue, rash, cough, vomiting, dizziness, pyrexia, hypokalemia, abdominal pain, constipation, decreased appetite, night sweats, pruritus, back pain, chills, leukopenia, neutropenia, lymphopenia, thrombocytopenia, and anemia.

In some embodiments, the one or more treatment-emergent adverse events comprise one or more of diarrhea/colitis and rash.

In some embodiments, the diarrhea/colitis comprises one or more of diarrhea, colitis, enterocolitis, gastrointestinal inflammation, colitis microscopic, and cytomegalovirus colitis.

In some embodiments, the rash comprises one or more of dermatitis exfoliative, rash, rash erythematous, rash macular, rash maculopapular, rash pruritic, exfoliative rash, rash generalized, rash popular, and rash pustular.

In some embodiments, the neutropenia comprises febrile neutropenia.

In some embodiments, the elevated transaminase comprises elevated alanine transaminase (ALT), aspartate transaminase (AST), or a combination thereof.

As used herein, the term "contacting" refers to the bringing together of indicated moieties in an in vitro system or an in vivo system. For example, "contacting" a PI3K with a PI3Kδ inhibitor compound described herein includes the administration of a compound described herein to an individual or patient, such as a human, having a PI3K, as well as, for example, introducing a compound described herein into a sample containing a cellular or purified preparation containing the PI3K.

In some embodiments, the inhibitor of PI3Kδ is a compound of US Patent Publ. No. US 2011/0015212, filed Jun. 28, 2010, US Patent Publ. No. 2013/0059835, filed Aug. 31, 2013, US Patent Publ. No. 2011/0183985, filed Dec. 17, 2010, US Patent Publ. No. 2012/0157430, filed Dec. 19, 2011, US Patent Publ. No. 2014/0249132, filed Feb. 28, 2014, or US Patent Publ. No. 2016/0257689, filed Feb. 26, 2016, each of which is incorporated herein by reference in its entirety.

In some embodiments, the inhibitor of PI3Kδ is prepared by the methods in US Patent Publ. No. US 2011/0015212, filed Jun. 28, 2010, US Patent Publ. No. 2013/0059835, filed Aug. 31, 2013, US Patent Publ. No. 2011/0183985, filed Dec. 17, 2010, or US Patent Publ. No. 2012/0157430, filed Dec. 19, 2011, US Patent Publ. No. 2014/0249132, filed Feb. 28, 2014, or US Patent Publ. No. 2016/0257689, filed Feb. 26, 2016, each of which is incorporated herein by reference in its entirety.

In some embodiments, the inhibitor of PI3Kδ is selected from:
4-{3-[1-(4-amino-3-methyl-1H-pyrazolo[3,4-d]pyrimidin-1-yl)ethyl]-5-chloro-2-ethoxy-6-fluorophenyl}pyrrolidin-2-one; and
5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one;
or a pharmaceutically acceptable salt thereof.

In some embodiments, the inhibitor of PI3Kδ is 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one, or a pharmaceutically acceptable salt thereof.

In some embodiments, the inhibitor of PI3Kδ is selected from:
(S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one; and
(R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;

or a pharmaceutically acceptable salt thereof.

In some embodiments, the inhibitor of PI3Kδ is a pharmaceutically acceptable salt of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one.

In some embodiments, the inhibitor of PI3Kδ is selected from a pharmaceutically acceptable salt of:
(S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one; and
(R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one.

In some embodiments, the inhibitor of PI3Kδ is a pharmaceutically acceptable salt of (R)-4-(3-45)-1-(4-amino-3-methyl-1H-pyrazolo[3,4-d]pyrimidin-1-yl)ethyl)-5-chloro-2-ethoxy-6-fluorophenyl)pyrrolidin-2-one.

In some embodiments, the inhibitor of PI3Kδ is (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt. In some embodiments, the salt is a 1:1 stoichiometric ratio of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one to hydrochloric acid.

In some embodiments, the salt is crystalline (see e.g., US Patent Publ. No. 2016/0257689, filed Feb. 26, 2016 for methods and processes for preparing (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt. US Patent Publ. No. 2016/0257689 is incorporated herein by reference, in its entirety).

In some embodiments, the hydrochloric acid salt of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one has: at least one, two, three, four or five XRPD peaks, in terms of 2-theta, selected from about 11.3°, about 16.4°, about 21.0°, about 23.0°, about 28.1°, about 31.2°, and about 32.8°; at least two XRPD peaks, in terms of 2-theta, selected from about 11.3°, about 16.4°, about 21.0°, about 23.0°, about 28.1°, about 31.2°, and about 32.8°; at least three XRPD peaks, in terms of 2-theta, selected from about 11.3°, about 16.4°, about 21.0°, about 23.0°, about 28.1°, about 31.2°, and about 32.8°. In some embodiments, the hydrochloric acid salt of the compound of Formula I has at least four XRPD peaks, in terms of 2-theta, selected from about 11.3°, about 16.4°, about 21.0°, about 23.0°, about 28.1°, about 31.2°, and about 32.8°. In some embodiments, the hydrochloric acid salt of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one has all of the listed XRPD peaks, in terms of 2-theta, at about 11.3°, about 16.4°, about 21.0°, about 23.0°, about 28.1°, about 31.2°, and about 32.8°. In some embodiments, the hydrochloric acid salt of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one has a DSC thermogram having an endothermic peak at about 207° C.

In some embodiments, the salts and compounds described herein are substantially isolated. By "substantially isolated" is meant that the salt or compound is at least partially or substantially separated from the environment in which it was formed or detected. Partial separation can include, for example, a composition enriched in the salts described herein. Substantial separation can include compositions containing at least about 50%, at least about 60%, at least about 70%, at least about 80%, at least about 90%, at least about 95%, at least about 97%, or at least about 99% by weight of the salts described herein, or salt thereof. Methods for isolating compounds and their salts are routine in the art.

In some embodiments, the inhibitor of PI3Kδ is 5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one, or a pharmaceutically acceptable salt thereof.

In some embodiments, the inhibitor of PI3Kδ is selected from:
(R)-5-{3-[(R)-1-(4-amino-3-methyl-1H-pyrazolo[3,4-d]pyrimidin-1-yl)ethyl]-5-chloro-2-ethoxy-6-fluorophenyl}-1,3-oxazolidin-2-one;
(R)-5-{3-[(S)-1-(4-amino-3-methyl-1H-pyrazolo[3,4-d]pyrimidin-1-yl)ethyl]-5-chloro-2-ethoxy-6-fluorophenyl}-1,3-oxazolidin-2-one;
(S)-5-{3-[(S)-1-(4-amino-3-methyl-1H-pyrazolo[3,4-d]pyrimidin-1-yl)ethyl]-5-chloro-2-ethoxy-6-fluorophenyl}-1,3-oxazolidin-2-one; and
(S)-5-{3-[(R)-1-(4-amino-3-methyl-1H-pyrazolo[3,4-d]pyrimidin-1-yl)ethyl]-5-chloro-2-ethoxy-6-fluorophenyl}-1,3-oxazolidin-2-one;
or a pharmaceutically acceptable salt thereof.

Compounds described herein, including salts thereof, can be prepared using known organic synthesis techniques and can be synthesized according to any of numerous possible synthetic routes. In some embodiments, the compounds can be prepared as described in U.S. Pat. Nos. 9,199,982 and 9,932,341, each of which is incorporated herein by reference in its entirety.

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^{1}$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative*

*LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

The compounds described herein can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds described herein can be used in methods of modulating a PI3K by contacting the PI3K with any one or more of the compounds or compositions described herein. In some embodiments, compounds of the present invention can act as inhibitors of one or more PI3Ks. In further embodiments, the compounds described herein can be used to modulate activity of a PI3K in an individual in need of modulation of the receptor by administering a modulating amount of a compound described herein, or a pharmaceutically acceptable salt thereof. In some embodiments, modulating is inhibiting. Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

The inhibitors of PI3Kδ described herein can be selective. By "selective" is meant that the compound binds to or inhibits a kinase with greater affinity or potency, respectively, compared to at least one other kinase. In some embodiments, the compounds described herein are selective inhibitors of PI3Kδ over PI3Kγ, PI3Kα and/or PI3Kβ. In some embodiments, the compounds described herein are selective inhibitors of PI3Kδ (e.g., over PI3Kα, PI3Kβ and PI3Kγ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds described herein can be determined by cellular assays associated with particular PI3K kinase activity.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments of the present methods, more than one compound described herein is used to inhibit the activity of one kinase (e.g., PI3Kγ or PI3Kδ).

In some embodiments of the present methods, more than one compound described herein is used to inhibit more than one kinase, such as at least two kinases (e.g., PI3Kγ and PI3Kδ).

In some embodiments of the present methods, one or more of the compounds is used in combination with another kinase inhibitor to inhibit the activity of one kinase (e.g., PI3Kγ or PI3Kδ).

In some embodiments of the present methods, one or more of the compounds is used in combination with another kinase inhibitor to inhibit the activities of more than one kinase (e.g., PI3Kγ or PI3Kδ), such as at least two kinases.

Another aspect of the present invention pertains to methods of treating a kinase (such as PI3Kδ)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma. In some embodiments, the B cell lymphoma is diffuse large B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

Further examples of PI3K-associated diseases include autoimmune hemolytic anemia, polycythemia vera, and pemphigus.

In some embodiments, the disease is non-Hodgkin lymphoma (NHL). In some embodiments, the non-Hodgkin lymphoma (NHL) is relapsed or refractory NHL or recurrent follicular NHL.

In some embodiments, the disease is an aggressive lymphoma (e.g., germinal center B cell-like (GCB) or activated B cell-like (ABC)).

In some embodiments, the disease is selected from diffuse large B-cell lymphoma, chronic lymphocytic leukemia (CLL), Non-Hodgkin lymphoma, hairy cell leukemia, Mantle cell lymphoma, small lymphocytic lymphoma, follicular lymphoma, lymphoplasmacytic lymphoma, extranodal marginal zone lymphoma, Hodgkin's lymphoma, Burkitt lymphoma, Waldenstrom's macroglobulinemia, prolymphocytic leukemia, acute lymphoblastic leukemia, myelofibrosis, mucosa-associated lymphatic tissue (MALT) lymphoma, mediastinal (thymic) large B-cell lymphoma, lymphomatoid granulomatosis, splenic marginal zone lymphoma, primary effusion lymphoma, intravascular large B-cell lymphoma, plasma cell leukemia, extramedullary plasmacytoma, smouldering myeloma (aka asymptomatic myeloma), monoclonal gammopathy of undetermined significance (MGUS), activated B-cell like (ABC) diffuse large B cell lymphoma (ABC-DLBCL), and germinal center B cell (GCB) diffuse large B cell lymphoma (GCB-DLBCL).

In some embodiments, the disease is myelofibrosis. In some embodiments, the myelofibrosis is selected from post-essential thrombocythemia myelofibrosis (PET-MF), primary myelofibrosis (PMF), and post-polycythemia vera myelofibrosis (PPV-MF). In some embodiments, the myelofibrosis is post-essential thrombocythemia myelofibrosis (PET-MF). In some embodiments, the myelofibrosis is primary myelofibrosis (PMF). In some embodiments, the myelofibrosis is post-polycythemia vera myelofibrosis (PPV-MF).

In some embodiments, the disease is acute myeloid leukemia. In some embodiments, the disease is Burkitt lymphoma. In some embodiments, the disease is activated B-cell like (ABC) diffuse large B cell lymphoma (ABC-DLBCL) or germinal center B cell (GCB) diffuse large B cell lymphoma (GCB-DLBCL).

In some embodiments, the disease is selected from chronic lymphocytic leukemia (CLL), diffuse large B-cell lymphoma (DLBCL) follicular lymphoma (FL) Hodgkin lymphoma (HL), mantle cell lymphoma (MCL), marginal zone lymphoma (MZL), and Waldenström macroglobulinemia (WM).

In some embodiments, the marginal zone lymphoma (MZL) is selected from extranodal MZL, nodal MZL, splenic MZL, and unknown MZL subtype.

In some embodiments, the Hodgkin lymphoma (HL) is selected from classic Hodgkin lymphoma (HL) and nodular lymphocytic-predominant HL.

In some embodiments, the diffuse large B-cell lymphoma is selected from activated B-cell like (ABC) diffuse large B cell lymphoma (ABC-DLBCL) and germinal center B cell (GCB) diffuse large B cell lymphoma (GCB-DLBCL).

In some embodiments, the disease is selected from autoimmune hemolytic anemia, polycythemia vera, and pemphigus.

In some embodiments, the present application further provides a method of treating a disease in a patient, wherein said disease selected from chronic lymphocytic leukemia (CLL), diffuse large B-cell lymphoma (DLBCL) follicular lymphoma (FL) Hodgkin lymphoma (HL), mantle cell lymphoma (MCL), marginal zone lymphoma (MZL), and Waldenström macroglobulinemia (WM), the method comprising:
   i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day to about 50 mg/day for a first period of time which is about 8 weeks to about 9 weeks; and
   ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 2.5 mg/day or less for a second period of time which occurs after the first period of time.

In some embodiments, the present application further provides a method of treating a disease in a patient, wherein said disease selected from chronic lymphocytic leukemia (CLL), diffuse large B-cell lymphoma (DLBCL) follicular lymphoma (FL) Hodgkin lymphoma (HL), mantle cell lymphoma (MCL), marginal zone lymphoma (MZL), and Waldenström macroglobulinemia (WM), the method comprising:
   i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day to about 50 mg/day for a first period of time which is about 8 weeks to about 9 weeks; and
   ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 20 mg/week to about 50 mg/week for a second period of time which occurs after the first period of time.

In some embodiments, the present application further provides a method of treating a disease in a patient, wherein said disease selected from chronic lymphocytic leukemia (CLL), diffuse large B-cell lymphoma (DLBCL) follicular lymphoma (FL) Hodgkin lymphoma (HL), mantle cell lymphoma (MCL), marginal zone lymphoma (MZL), and Waldenström macroglobulinemia (WM), the method comprising:
   i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day for a first period of time which is about 8 weeks; and
   ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 2.5 mg/day for a second period of time which occurs after the first period of time.

In some embodiments, the present application further provides a method of treating a disease in a patient, wherein said disease selected from chronic lymphocytic leukemia (CLL), diffuse large B-cell lymphoma (DLBCL) follicular lymphoma (FL) Hodgkin lymphoma (HL), mantle cell lymphoma (MCL), marginal zone lymphoma (MZL), and Waldenström macroglobulinemia (WM), the method comprising:
   i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day for a first period of time which is about 8 weeks; and
   ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 20 mg/week for a second period of time which occurs after the first period of time.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease. In some embodiments, the term "treating" or "treatment" refers to inhibiting or ameliorating the disease.

As used herein, "QD" is taken to mean a dosage administered to the subject once-daily. "QW" is taken to mean a dosage administered to the subject once-weekly. "Q2W" is taken to mean a dosage administered to the subject once, every other week. "Q3W" is taken to mean a dosage administered to the subject once, every three weeks. "Q4W" is taken to mean a dosage administered to the subject once, every four weeks.

As used herein, "about" when referring to a measurable value such as an amount, a dosage, a temporal duration, and the like, is meant to encompass variations of ±10%. In certain embodiments, "about" can include variations of ±5%, ±1%, or ±0.1% from the specified value and any variations there between, as such variations are appropriate to perform the disclosed methods.

Combination Therapies

I. Immune-Checkpoint Therapies

In some embodiments, the inhibitors of PI3K provided herein can be used in combination with one or more immune checkpoint inhibitors for the treatment of cancer as described herein. In one embodiment, the combination with one or more immune checkpoint inhibitors as described herein can be used for the treatment of a B-cell malignancy described here. Compounds of the present disclosure can be used in combination with one or more immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3Kδ, PI3Kγ, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the PI3K inhibitors provided herein can be used in combination with one or more agonists of immune checkpoint molecules, e.g., OX40, CD27, OX40, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies.

In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer. Examples of diseases and indications treatable with combination therapies include those as described herein.

One or more additional pharmaceutical or therapeutic agents such as, for example, chemotherapeutics, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF and FAK kinase inhibitors. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present disclosure and are presented as a non-limiting list: a cytostatic agent, taxotere, taxol, camptostar, epothilones, 5-fluorouracil, SCH 66336, R115777, L778,123, BMS 214662, IRESSA™ (gefitinib), TARCEVA™ (erlotinib), antibodies to EGFR, GLEEVEC™ (imatinib mesylate), intron, ara-C, adriamycin, cytoxan, chlormethine, triethylenemelamine, triethylenethiophosphoramine, busulfan, 6-mercaptopurine, 6-thioguanine, fludarabine phosphate, ELOXATIN™ (oxaliplatin), vindesine, mithramycin, deoxycoformycin, L-asparaginase, 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, medroxyprogesteroneacetate, leuprolide, flutamide, goserelin, hydroxyurea, amsacrine, navelbene, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), aphidicolon, rituxan, Sml1, triapine, didox, trimidox, amidox, 3-AP, and MDL-101, 731.

The compounds of the present disclosure can further be used in combination with other methods of treating cancers, for example by chemotherapy, irradiation therapy, tumortargeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example Bcr-Abl inhibitors include the compounds, and pharmaceutically acceptable salts.

Example suitable Flt-3 inhibitors include compounds, and their pharmaceutically acceptable salts.

Example suitable RAF inhibitors include compounds, and their pharmaceutically acceptable salts.

Example suitable FAK inhibitors include compounds, and their pharmaceutically acceptable salts.

In some embodiments, the compounds of the disclosure can be used in combination with one or more other kinase inhibitors including imatinib, particularly for treating patients resistant to imatinib or other kinase inhibitors.

The compounds can be used in combination with tumor vaccines and CAR (Chimeric antigen receptor) T cell treatment as a booster for T cell activation. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds can be combined with dendritic cells immunization to activate potent anti-tumor responses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

In some embodiments, the additional therapeutic agent is selected from a JAK inhibitor (e.g., a selective JAK1 inhibitor), a pan-PIM-selective kinase inhibitor, an inhibitor of epigenetic regulator, and an immunotherapeutic agent.

In some embodiments, the inhibitor of epigenetic regulator is selected from a bromo- and extra-terminal domain inhibitor, and a lysine-specific histone demethylase 1A inhibitor.

In some embodiments, the additional therapeutic agent is an immunotherapeutic agent.

In some embodiments, the immunotherapeutic agent is R-ICE.

In some embodiments, the additional therapeutic agent is a JAK inhibitor.

In some embodiments, the JAK inhibitor is selective for JAK1 and JAK2 over JAK3 and TYK2. In some embodiments, the JAK inhibitor is selective for JAK1 over JAK2, JAK3, and TYK2. For example, the JAK inhibitor may preferentially inhibit JAK1 over one or more of JAK2, JAK3, and TYK2. In some embodiments, the JAK inhibitor inhibits JAK1 preferentially over JAK2 (e.g., have a JAK1/JAK2 $IC_{50}$ ratio >1). In some embodiments, the JAK inhibitor is 10-fold more selective for JAK1 over JAK2. In some embodiments, the JAK inhibitor is about 3-fold, about 5-fold, about 10-fold, about 15-fold, or about 20-fold more selective for JAK1 over JAK2 as calculated by measuring $IC_{50}$ at 1 mM ATP (see e.g., U.S. patent application Ser. No. 14/680,659, filed Apr. 7, 2015, the disclosure of which is incorporated by reference herein in its entirety).

In some embodiments, the additional therapeutic agent is a JAK1/JAK2 inhibitor. In some embodiments, the additional therapeutic agent is ruxolitinib (e.g., ruxolitinib phosphate).

In some embodiments, the additional therapeutic agent is a JAK inhibitor selected from the group provided in the following table. The compounds in provided in the table are selective JAK1 inhibitors (selective over JAK2, JAK3, and TYK2). The $IC_{50}$s obtained by the method of Assay A described in U.S. patent application Ser. No. 14/680,659 at 1 mM ATP are shown in Table A.

TABLE A

| # | Prep. | Name | Structure | JAK1 $IC_{50}$ (nM) | JAK2/JAK1 |
|---|---|---|---|---|---|
| 1 | US 2016/000079 Example 1 | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 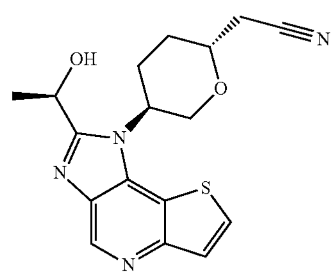 [SMILES: C[C@@H](O)c1nc2cnc3ccsc3c2n1[C@H]1CC[C@H](CC#N)OC1] | ++ | >10 |
| 2 | US 2016/000079 Example 2 | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 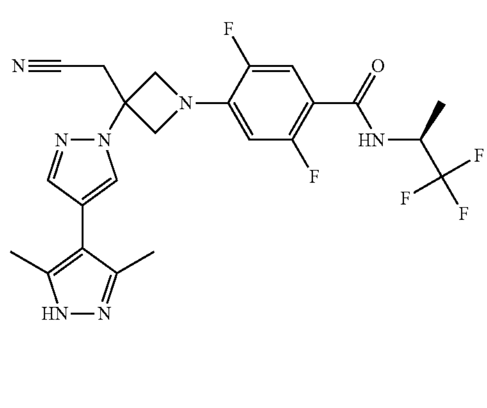 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |

TABLE A-continued

| # | Prep. | Name | Structure | JAK1 IC$_{50}$ (nM) | JAK2/JAK1 |
|---|---|---|---|---|---|
| 3 | US 2010/0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 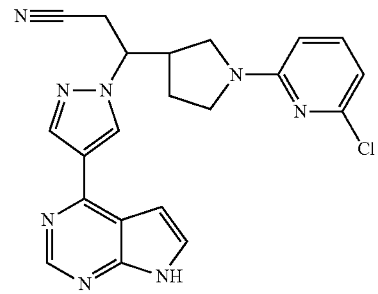 [SMILES: N#CCC(C1CCN(c2cccc(Cl)n2)C1)n1cc(-c2ncnc3[nH]ccc23)cn1] | + | >10 |
| 4 | US 2010/0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 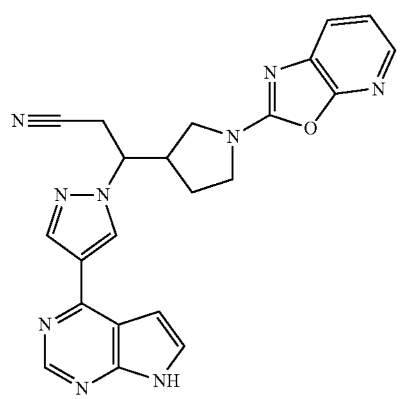 [SMILES: N#CCC(C1CCN(c2nc3cccnc3o2)C1)n1cc(-c2ncnc3[nH]ccc23)cn1] | + | >10 |
| 5 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 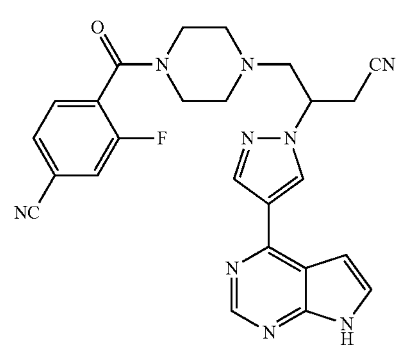 [SMILES: N#CCC(CN1CCN(C(=O)c2ccc(C#N)cc2F)CC1)n1cc(-c2ncnc3[nH]ccc23)cn1] | + | >10 |

TABLE A-continued

| # | Prep. | Name | Structure | JAK1 IC$_{50}$ (nM) | JAK2/JAK1 |
|---|---|---|---|---|---|
| 6 | US 2011/0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 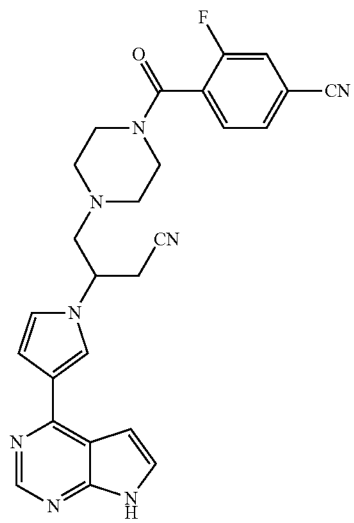 [SMILES: N#CCC(CN1CCN(C(=O)c2ccc(C#N)cc2F)CC1)n1ccc(-c2ncnc3[nH]ccc23)c1] | + | >10 |
| 7 | US 2011/0224190 (Example 1) | {1-{1-[3-Fluoro-2-(trifluoromethyl)iso-nicotinoyl]piperidin-4-yl}-3-[4-(7H-pyrrolo[2,3-d]pyrimidin-4-yl)-1H-pyrazol-1-yl]azetidin-3-yl}acetonitrile | 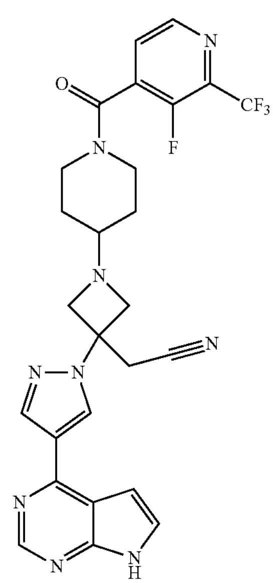 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE A-continued

| # | Prep. | Name | Structure | JAK1 IC$_{50}$ (nM) | JAK2/JAK1 |
|---|---|---|---|---|---|
| 8 | US 2011/0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 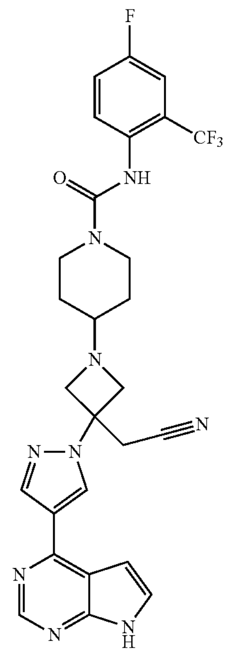 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 9 | US 2011/0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 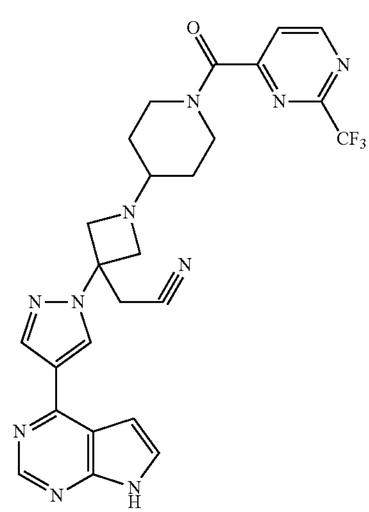 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE A-continued

| # | Prep. | Name | Structure | JAK1 IC$_{50}$ (nM) | JAK2/JAK1 |
|---|---|---|---|---|---|
| 10 | US 2012/0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 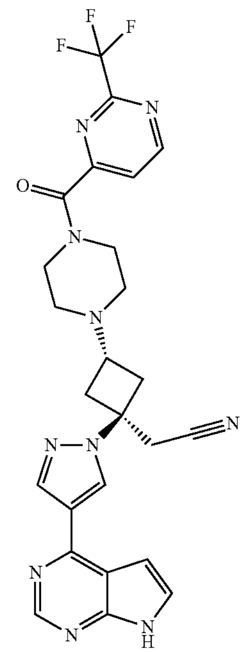 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 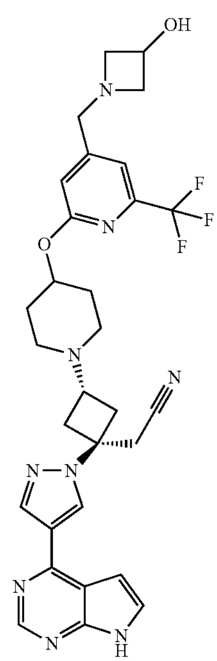 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 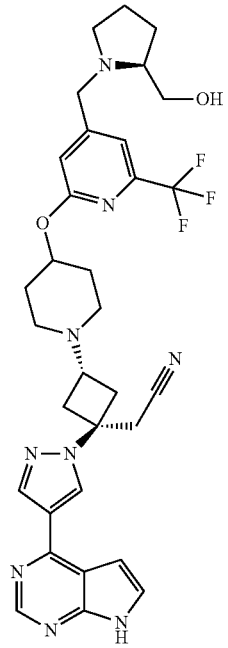 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 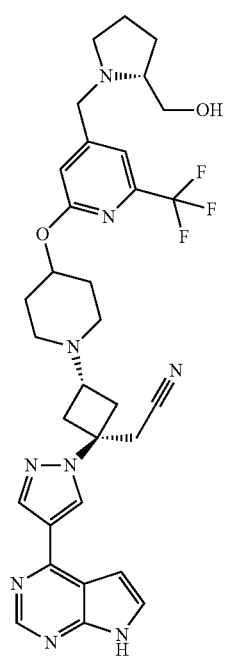 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE A-continued

| # | Prep. | Name | Structure | JAK1 IC$_{50}$ (nM) | JAK2/ JAK1 |
|---|---|---|---|---|---|
| 14 | US 2012/ 0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 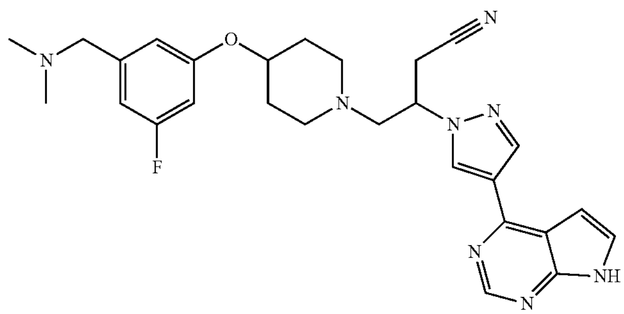 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/ 0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 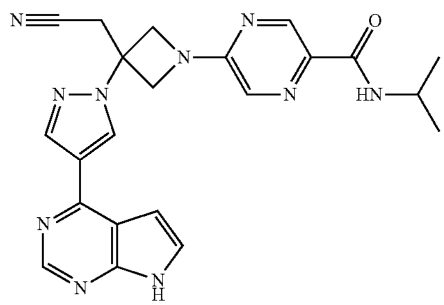 [SMILES: CC(C)NC(=O)c1cnc(N2CC(CC#N)(n3cc(-c4ncnc5[nH]ccc45)cn3)C2)cn1] | + | >10 |
| 16 | US 2013/ 0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 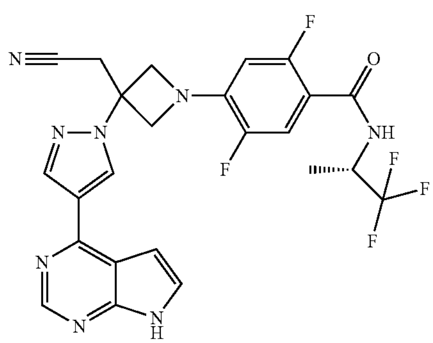 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/ 0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 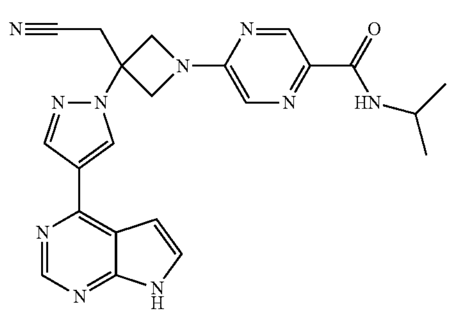 [SMILES: CC(C)NC(=O)c1cnc(N2CC(CC#N)(n3cc(-c4ncnc5[nH]ccc45)cn3)C2)cn1] | + | >10 |

TABLE A-continued

| # | Prep. | Name | Structure | JAK1 IC$_{50}$ (nM) | JAK2/JAK1 |
|---|---|---|---|---|---|
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 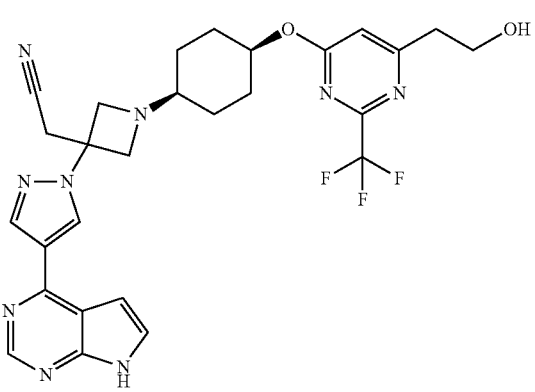 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 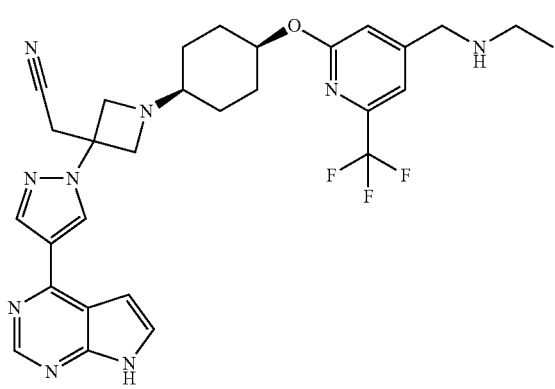 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 (Example 69) | {1-(cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 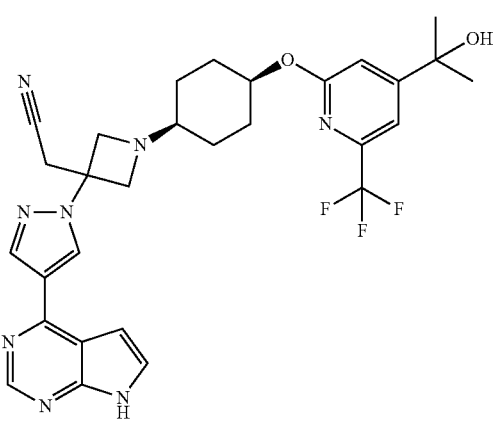 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE A-continued

| # | Prep. | Name | Structure | JAK1 IC$_{50}$ (nM) | JAK2/JAK1 |
|---|---|---|---|---|---|
| 21 | US 2013/004593 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 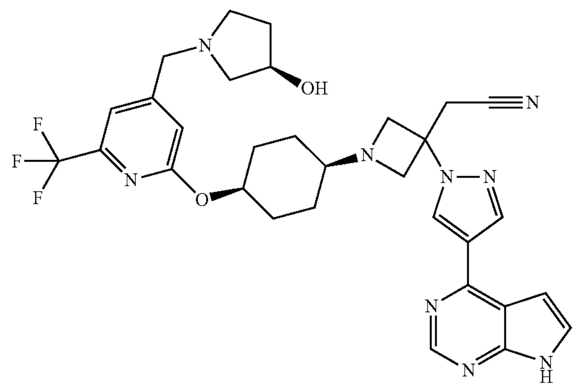 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 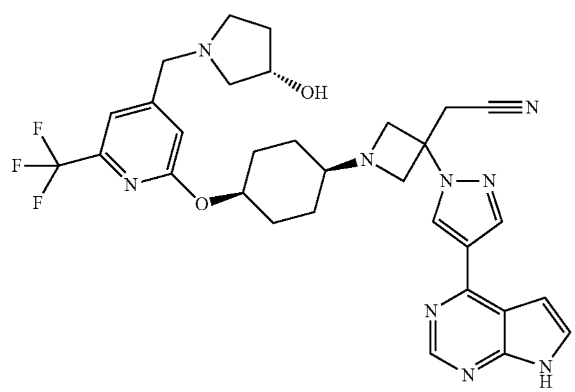 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 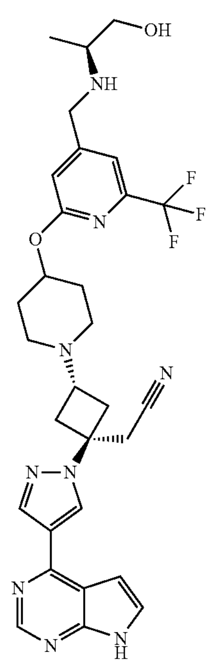 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Prep. | Name | Structure | JAK1 IC$_{50}$ (nM) | JAK2/JAK1 |
|---|---|---|---|---|---|
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 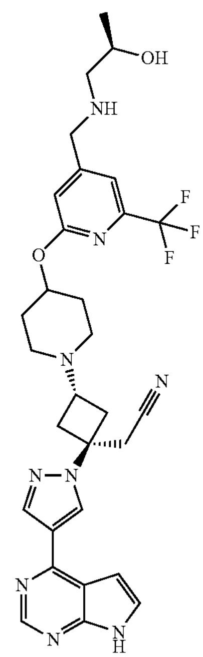 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 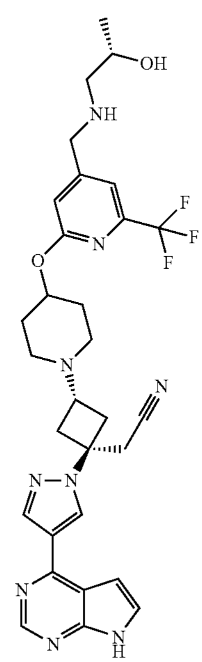 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 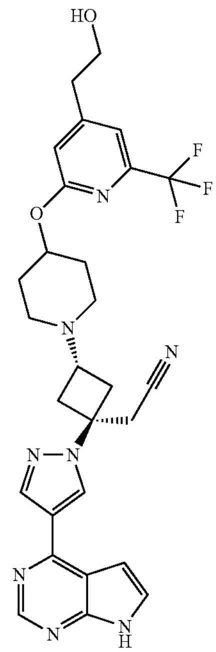 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see U.S. patent application Ser. No.: 14/680,659, Example A for assay conditions)
++ means ≤100 nM (see U.S. patent application Ser. No.: 14/680,659, Example A for assay conditions)
+++ means ≤300 nM (see U.S. patent application Ser. No.: 14/680,659, Example A for assay conditions)
$^a$Data for enantiomer 1
$^b$Data for enantiomer 2

In some embodiments, the JAK inhibitor is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile (i.e., itacitinib), or a pharmaceutically acceptable salt thereof.

In some embodiments, the JAK inhibitor is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the JAK inhibitor is 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide, or a pharmaceutically acceptable salt thereof.

In some embodiments, the JAK inhibitor is selected from (R)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (R)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (R)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (R)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, or (R)-4-(4-{3-[dimethylamino)methyl]-5-fluorophenoxy}piperidin-1-yl)-3-[4-(7H-pyrrolo[2,3-d]pyrimidin-4-yl)-1H-pyrazol-1-yl]butanenitrile, (S)-3-[1-(6-chloropyridin-2-yl)pyrrolidin-3-yl]-3-[4-(7H-pyrrolo[2,3-d]pyrimidin-4-yl)-1H-pyrazol-1-yl]propanenitrile, (S)-3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile, (S)-4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile, (S)-4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile, (S)-4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile; and pharmaceutically acceptable salts of any of the aforementioned.

In some embodiments, the compounds of Table A are prepared by the synthetic procedures described in US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK inhibitor is selected from the compounds of US Patent Publ. No. 2010/0298334, filed May 21, 2010, US Patent Publ. No. 2011/0059951, filed Aug. 31, 2010, US Patent Publ. No. 2011/0224190, filed Mar. 9, 2011, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the inhibitor of PI3Kδ and additional therapeutic agent are administered simultaneously.

In some embodiments, the inhibitor of PI3Kδ and additional therapeutic agent are administered sequentially.

Pharmaceutical Formulations

When employed as pharmaceuticals, the compounds used in the methods of the disclosure can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, the compound of the disclosure or a pharmaceutically acceptable salt thereof, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the disclosure may be milled using known milling procedures such as wet milling to obtain a particle size appropriate for tablet formation and for other formulation types. Finely divided (nanoparticulate) preparations of the compounds of the disclosure can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

The compositions can be formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g.

glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the disclosure. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of a compound of the disclosure in a pharmaceutical composition can vary depending upon a number of factors including dosage, chemical characteristics (e.g., hydrophobicity), and the route of administration. For example, the compounds of the disclosure can be provided in an aqueous physiological buffer solution containing about 0.1 to about 10% w/v of the compound for parenteral administration.

The compositions of the disclosure can further include one or more additional pharmaceutical agents such as a chemotherapeutic, steroid, anti-inflammatory compound, or immunosuppressant, examples of which are listed herein.

Labeled Compounds and Assay Methods

The methods of the present disclosure further includes the use of isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^2$H (also written as D for deuterium), $^3$H (also written as T for tritium) $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of an alkyl group of a compound described herein can be optionally substituted with deuterium atoms, such as —CD$_3$ being substituted for —CH$_3$).

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

In some embodiments, 1, 2, 3, 4, 5, 6, 7, or 8 hydrogen atoms, attached to carbon atoms of the compounds described herein, are optionally replaced by deuterium atoms.

Synthetic methods for including isotopes into organic compounds are known in the art (Deuterium Labeling in Organic Chemistry by Alan F Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. J. Med. Chem. 2011, 54, 201-210; R. Xu et. al. J. Label Compd. Radiopharm. 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro PI3K labeling and competition assays, compounds that incorporate $^3$H, $^{14}$C, $^{82}$Br, $^{125}$I, $^{131}$I, or, $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

Kits

The present disclosure also includes pharmaceutical kits useful, for example, in the treatment or prevention of PI3K-associated diseases or disorders described herein, which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit. In certain embodiments, said instructions comprise the methods of the present disclosure including specified dosages or dosing regimens of the present disclosure.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

EXAMPLES

Examples 1A-1D. Diastereoisomers of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one

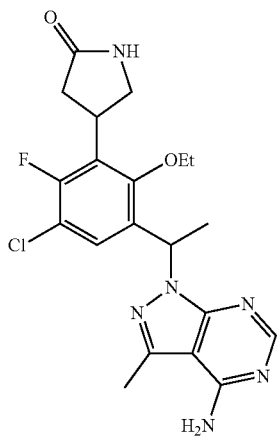 [SMILES: CCOc1c(C(C)n2nc(C)c3c(N)ncnc32)cc(Cl)c(F)c1C1CNC(=O)C1]

Step 1. 1-(5-Chloro-2-ethoxy-3-iodo-4-methylphenyl)ethanol

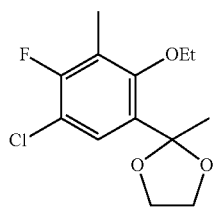 [SMILES: CCOc1c(C2(C)OCCO2)cc(Cl)c(F)c1C]

A solution of 1-(5-chloro-2-ethoxy-4-fluoro-3-iodophenyl)ethanone (20.0 g, 58.4 mmol; see Example 212, step 1 of U.S. Pat. No. 9,199,982) and 1,2-ethanediol (6.5 mL, 120 mmol) in toluene (190 mL) was treated with p-toluenesulfonic acid monohydrate (1.1 g, 5.8 mmol). The flask was fitted with a Dean-Stark trap that was filled with sieves, and refluxed for 3 h. The reaction mixture was cooled and added to ice cooled saturated sodium bicarbonate solution (250 mL) and extracted with ethyl acetate. The organic layer was washed with brine, dried over sodium sulfate, filtered, and concentrated to a crude orange oil. The crude material was purified by flash column chromatography using ethyl acetate in hexanes (0%-20%) to give the desired product (22 g, 99%). LCMS for $C_{12}H_{14}ClFIO_3$ $(M+H)^+$: m/z=387.0; Found: 386.9.

Step 2. Ethyl (2E)-3-[3-chloro-6-ethoxy-2-fluoro-5-(2-methyl-1,3-dioxolan-2-yl)phenyl]acrylate

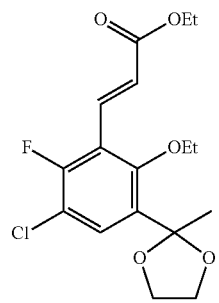 [SMILES: CCOC(=O)/C=C/c1c(F)c(Cl)cc(C2(C)OCCO2)c1OCC]

A mixture of 2-(5-chloro-2-ethoxy-4-fluoro-3-iodophenyl)-2-methyl-1,3-dioxolane (22 g, 58 mmol) (from Step 1), ethyl (2E)-3-(4,4,5,5-tetramethyl-1,3,2-dioxaborolan-2-yl)acrylate (16 mL, 70 mmol), and potassium carbonate (24 g, 170 mmol) in 1,4-dioxane (230 mL) and water (110 mL) was degassed with nitrogen for 10 min. The reaction mixture was treated with [1,1'-bis (diphenylphosphino\)ferrocene]dichloropalladium(II), complex with dichloromethane (1:1) (2.4 g, 2.9 mmol), degassed with nitrogen for another 10 min, and heated at 80° C. for 2 h. The reaction mixture was filtered through Celite and washed with ethyl acetate (300 mL). The filtrate was poured into water (400 mL). The aqueous layer was separated and extracted with additional ethyl acetate (300 mL). The combined organic extracts were washed with brine, dried over sodium sulfate, filtered, and concentrated to a crude brown solid. The crude material was purified by flash column chromatography using ethyl acetate in hexanes (0%-30%) to give the desired product (20 g, 96%). NMR (400 MHz, CDCl$_3$) δ 7.74 (d, J=16.5 Hz, 1H), 7.56 (d, J=8.6 Hz, 1H), 6.70 (dd, J=16.5, 0.9 Hz, 1H), 4.26 (q, J=7.1 Hz, 2H), 4.10-3.99 (m, 2H), 3.91 (q, J=7.0 Hz, 2H), 3.87-3.76 (m, 2H), 1.73 (s, 3H), 1.44 (t, J=7.0 Hz, 3H), 1.33 (t, J=7.1 Hz, 3H). LCMS for $C_{17}H_{21}ClFO_5$ $(M+H)^+$: m/z=359.1; Found: 359.1.

Step 3. Ethyl 3-[3-chloro-6-ethoxy-2-fluoro-5-(2-methyl-1,3-dioxolan-2-yl)phenyl]-4-nitrobutanoate

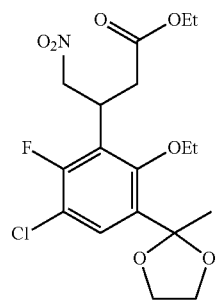 [SMILES: CCOC(=O)CC(C[N+](=O)[O-])c1c(F)c(Cl)cc(C2(C)OCCO2)c1OCC]

A solution ethyl (2E)-3-[3-chloro-6-ethoxy-2-fluoro-5-(2-methyl-1,3-dioxolan-2-yl\)phenyl]acrylate (10 g, 28 mmol) (from Step 2) in nitromethane (100 mL) was treated with 1,8-diazabicyclo[5.4.0]undec-7-ene (4.6 mL, 31 mmol) and stirred at 60° C. for 15 h. The reaction mixture was poured into water (400 mL) and extracted with ethyl acetate (2×300 mL). The combined organic extracts were washed with brine, dried over sodium sulfate, filtered, and concentrated to a crude orange oil. The crude material was purified by flash column chromatography using ethyl acetate in hexanes (0%-30%) to give the desired product as a mixture of enantiomers (10.4 g, 89%). $^1$H NMR (400 MHz, CDCl$_3$) δ 7.52 (d, J=9.1 Hz, 1H), 4.82 (ddd, J=12.5, 7.6, 1.4 Hz, 1H), 4.68 (dd, J=12.5, 7.2 Hz, 1H), 4.54-4.40 (m, 1H), 4.15-3.90 (m, 6H), 3.89-3.75 (m, 2H), 2.85 (ddd, J=16.0, 8.6, 1.4 Hz, 1H), 2.73 (dd, J=16.1, 6.2 Hz, 1H), 1.70 (s, 3H), 1.47 (t, J=7.0 Hz, 3H), 1.21 (t, J=7.1 Hz, 3H). LCMS for C$_{18}$H$_{24}$ClFNO$_7$ (M+H)$^+$: m/z=420.1; Found: 420.1.

Step 4. Enantiomers 4-[3-chloro-6-ethoxy-2-fluoro-5-(2-methyl-1,3-dioxolan-2-yl)phenyl]pyrrolidin-2-one

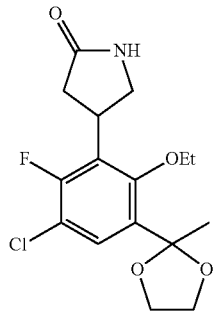 [SMILES: CCOc1c(C2(C)OCCO2)cc(Cl)c(F)c1C1CNC(=O)C1]

A suspension of ethyl 3-[3-chloro-6-ethoxy-2-fluoro-5-(2-methyl-1,3-dioxolan-2-yl)phenyl]-4-nitrobutanoate (1.0 g, 2.4 mmol) (from Step 3) in ethanol (16 mL) was warmed to dissolve the solid. The solution was cooled back to ambient temperature, degassed with nitrogen, and treated with a slurry of 2800 Raney Nickel in water (1.5 mL). The reaction mixture was degassed again with nitrogen and hydrogenated with a balloon of hydrogen for 3 h. The reaction mixture was filtered through Celite and concentrated to give the intermediate amino ester (0.93 g, 100%). The intermediate amino ester was dissolved in toluene (12 mL) and heated at 110° C. for 12 h. The reaction mixture was cooled to ambient temperature, at which point a solid precipitated from solution. This mixture was cooled to 0° C., stirred for 30 min, filtered, washed with cold toluene, and dried to give the desired product as a mixture of enantiomers (0.61 g, 75%). LCMS for C$_{16}$H$_{20}$ClFNO$_4$ (M+H)$^+$: m/z=344.1; Found: 344.1. The mixture of enantiomers was separated by chiral HPLC to give the individual enantiomers as peak 1 and peak 2 (RT=5.39 min and 7.01 min, respectively; Phenomenex Lux Cellulose C-1, 21.2×250 mm, 5 micron particle size, eluting with 20% ethanol in hexanes at 18 mL/min).

Step 5. Enantiomers of 4-(3-acetyl-5-chloro-2-ethoxy-6-fluorophenyl)pyrrolidin-2-one

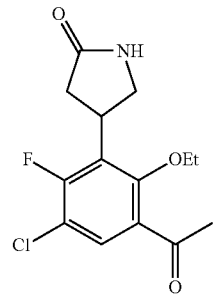 [SMILES: CCOc1c(C(C)=O)cc(Cl)c(F)c1C1CNC(=O)C1]

The separated enantiomers from step 4 were each processed individually to the final compounds. A solution of 4-[3-chloro-6-ethoxy-2-fluoro-5-(2-methyl-1,3-dioxolan-2-yl)phenyl]pyrrolidin-2-one (1.7 g, 5.0 mmol) (from Step 4) in methanol (17 mL) was treated with 6.0 M hydrogen chloride in water (11 mL, 69 mmol) dropwise and stirred 20° C. for 30 min. The reaction mixture was added dropwise to ice cooled saturated sodium bicarbonate solution (75 ml) and extracted with ethyl acetate (2×100 ml). The combined organic extracts were washed with brine, dried over sodium sulfate, filtered, and concentrated to give the desired products [from peak 1 (1.5 g, 99%); from peak 2 (1.5 g, 99%)] that were used without further purification. From peak 1: $^1$H NMR (400 MHz, DMSO-d$_6$) δ 7.84 (s, 1H), 7.70 (d, J=8.6 Hz, 1H), 4.16-3.99 (m, 1H), 3.83 (q, J=7.0 Hz, 2H), 3.65-3.54 (m, 1H), 3.30-3.23 (m, 1H), 2.55 (s, 3H), 2.33 (dd, J=16.8, 8.4 Hz, 1H), 1.30 (t, J=7.0 Hz, 3H). LCMS for C$_{14}$H$_{16}$ClFNO$_3$ (M+H)$^+$: m/z=300.1; Found: 300.0. From peak 2: $^1$H NMR (400 MHz, DMSO-d$_6$) δ 7.84 (s, 1H), 7.70 (d, J=8.6 Hz, 1H), 4.13-4.00 (m, 1H), 3.87-3.77 (m, 2H), 3.65-3.55 (m, 1H), 3.31-3.23 (m, 1H), 2.55 (s, 3H), 2.32 (ddd, J=16.9, 8.4, 1.6 Hz, 1H), 1.30 (t, J=7.0 Hz, 3H). LCMS for C$_{14}$H$_{16}$ClFNO$_3$ (M+H)$^+$: m/z=300.1; Found: 300.1.

Step 6. Diastereoisomers of 4-[3-chloro-6-ethoxy-2-fluoro-5-(1-hydroxyethyl)phenyl]pyrrolidin-2-one

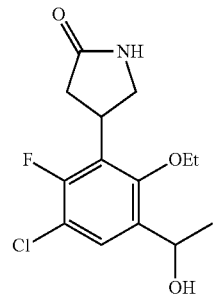 [SMILES: CCOc1c(C(C)O)cc(Cl)c(F)c1C1CNC(=O)C1]

The enantiomers from step 5 were each processed individually to the final products. A solution of 4-(3-acetyl-5-chloro-2-ethoxy-6-fluorophenyl)pyrrolidin-2-one (0.402 g, 1.34 mmol) (from Step 5) in anhydrous methanol (6.7 mL)

under an atmosphere of nitrogen at 0° C. was treated with sodium tetrahydroborate (0.10 g, 2.7 mmol) and stirred at 0° C. for 30 min. The reaction mixture was quenched with water at 0° C. and poured into water (50 mL)/ethyl acetate (100 mL) while stirring. The mixture was warmed to ambient temperature and the aqueous layer was separated and extracted with additional ethyl acetate (50 mL). The combined organic extracts were washed with brine, dried over sodium sulfate, filtered, and concentrated to give white foams. The crude material were purified by flash column chromatography using acetonitrile (containing 7% methanol) in dichloromethane (0%-100%) to give the desired products as mixtures of diastereoisomers [from peak 1 (0.40 g, 99%); from peak 2 (0.40 g, 99%)]. From peak 1: LCMS for $C_{14}H_{18}ClFNO_3$ (M+H)$^+$: m/z=302.1; Found: 302.0. From peak 2: LCMS for $C_{14}H_{18}ClFNO_3$ (M+H)$^+$: m/z=302.1; Found: 302.1.

Step 7. Diastereoisomers of 4-[3-chloro-5-(1-chloroethyl)-6-ethoxy-2-fluorophenyl]pyrrolidin-2-one

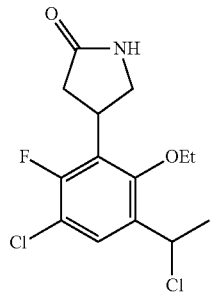 [SMILES: CCOc1c(C(C)Cl)cc(Cl)c(F)c1C1CNC(=O)C1]

The mixture of diastereoisomers from step 6 were each processed individually to the final products. A solution of 4-[3-chloro-6-ethoxy-2-fluoro-5-(1-hydroxyethyl)phenyl]pyrrolidin-2-one (0.41 g, 1.4 mmol) (from Step 6) in methylene chloride (12 mL) was treated with N,N-dimethylformamide (0.011 mL, 0.14 mmol) followed by thionyl chloride (0.21 mL, 2.9 mmol) dropwise and stirred at 20° C. for 30 min. The reaction mixture was added dropwise to ice cooled saturated sodium bicarbonate solution and extracted with dichloromethane. The organic layer was separated and washed with brine, dried over sodium sulfate, filtered, and concentrated to give the desired products [from peak 1 (0.38 g, 87%); from peak 2 (0.39 g, 89%)] along with 17-18% of the styrene that formed from chloride elimination. These mixtures were used without further purification. From peak 1: LCMS for $C_{14}H_{17}Cl_2FNO_2$ (M+H)$^+$: m/z=320.1; Found: 320.0. From peak 2: LCMS for $C_{14}H_{17}Cl_2FNO_2$ (M+H)$^+$: m/z=320.1; Found: 320.0.

Step 8. Diastereoisomers of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one

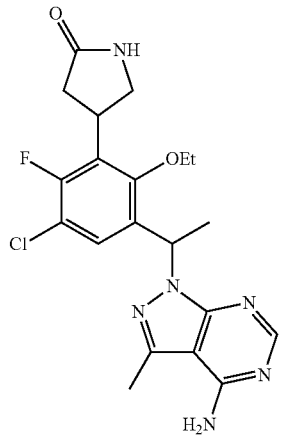 [SMILES: CCOc1c(C(C)n2nc(C)c3c(N)ncnc32)cc(Cl)c(F)c1C1CNC(=O)C1]

The mixture of diastereoisomers from step 7 were each processed individually to the final products. A mixture of 4-[3-chloro-5-(1-chloroethyl)-6-ethoxy-2-fluorophenyl]pyrrolidin-2-one (0.36 g, 1.1 mmol) (from Step 7), 3-methyl-1H-pyrazolo[3,4-d]pyrimidin-4-amine (0.19 g, 1.3 mmol), cesium carbonate (0.54 g, 1.7 mmol) and potassium iodide (18 mg, 0.11 mmol) in N,N-dimethylformamide (7.4 mL) was heated at 100° C. for 4.5 h. The reaction mixture was poured into water (30 ml) and extracted with ethyl acetate (3×50 mL) to give a mixture of diastereoisomer ((S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one; (R)-4-(3-((S)-1-(4-amino-3-methyl-1H-pyrazolo[3,4-d]pyrimidin-1-yl)ethyl)-5-chloro-2-ethoxy-6-fluorophenyl) pyrrolidin-2-one; (S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one; and (R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one). The mixture of diastereoisomers were purified by preparative LCMS (XBridge C18 column, eluting with a gradient of acetonitrile/water containing 0.1% ammonium hydroxide, at flow rate of 60 mL/min) to give the desired products [from peak 1 were isolated peak A (Example 1A) (0.13 g, 54%) and peak B (Example 1B) (0.11 g, 46%); from peak 2 were isolated peak A (Example 1C) (0.15 g, 63%) and peak B (Example 1D) (0.14 g, 55%)].

Example 1B: $^1$H NMR (300 MHz, DMSO-d$_6$) δ 8.12 (s, 1H), 7.82 (s, 1H), 7.52 (d, J=8.5 Hz, 1H), 7.30 (br s, 1H), 6.23 (q, J=7.0 Hz, 1H), 4.05-3.90 (m, 1H), 3.88-3.78 (m, 2H), 3.63-3.53 (m, 1H), 3.29-3.20 (m, 1H), 2.54 (s, 3H), 2.38-2.21 (m, 1H), 1.70 (d, J=7.1 Hz, 3H), 1.39 (t, J=6.9 Hz, 3H). LCMS for $C_{20}H_{23}ClFN_6O_2$ (M+H)$^+$: m/z=433.2; Found: 433.1. Example 1C: $^1$H NMR (500 MHz, DMSO-d$_6$) δ 8.12 (s, 1H), 7.77 (s, 1H), 7.53 (d, J=8.5 Hz, 1H), 7.26 (br s, 2H), 6.24 (q, J=7.0 Hz, 1H), 4.04-3.94 (m, 1H), 3.93-3.85 (m, 1H), 3.84-3.77 (m, 1H), 3.61-3.53 (m, 1H), 3.27-3.22 (m, 1H), 2.54 (s, 3H), 2.30 (dd, J=18.1, 8.6 Hz, 1H), 1.71 (d, J=7.1 Hz, 3H), 1.40 (t, J=6.9 Hz, 3H). LCMS for $C_{20}H_{23}ClFN_6O_2$ (M+H)$^+$: m/z=433.2; Found: 433.1.

Examples 2A-2D. Diastereomers of 5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one

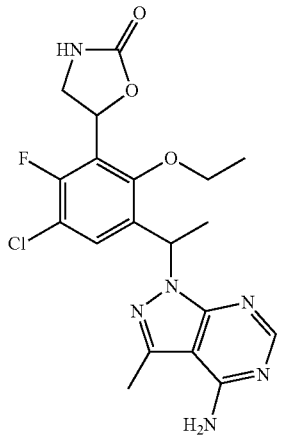 [SMILES: CCOc1c(C(C)n2nc(C)c3c(N)ncnc32)cc(Cl)c(F)c1C1CNC(=O)O1]

Step 1: tert-Butyl [2-(3-acetyl-5-chloro-2-ethoxy-6-fluorophenyl)-2-hydroxyethyl]carbamate

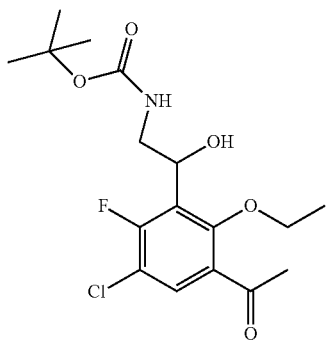 [SMILES: CCOc1c(C(C)=O)cc(Cl)c(F)c1C(O)CNC(=O)OC(C)(C)C]

0.2 M Osmium tetraoxide in water (10 mL) was added to a solution of tert-butyl [(4-chlorobenzoyl)oxy]carbamate (Lawrence Harris, *J. Org. Chem,* 2011, 76, 358-372). (19 g, 70 mmol) in acetonitrile (210 mL) and stirred for 10 minutes. 1-(5-chloro-2-ethoxy-4-fluoro-3-vinylphenyl)ethanone (11.2 g, 46 mmol) (see Example 353, Step 1 of U.S. Pat. No. 9,199,982) as a solution in acetonitrile (210 mL) was added to the carbamate solution followed by the addition of water (50 mL) and the reaction was stirred for 3 hours at room temperature. The reaction was quenched with saturated 10 M dipotassium disulfite in water (240 mL) and stirred for 5 minutes. Water was added and the reaction mixture was extracted with ethyl acetate. The extracts were washed with saturated sodium bicarbonate solution, brine and dried over sodium sulfate, filtered and evaporated. Purification on silica gel using ethyl acetate in hexanes (0-100%) gave the desired compound as a racemic mixture, 16.6 g, 95%. LCMS calculated for $C_{17}H_{23}ClFNO_5Na$ (M+Na)$^+$: m/z=398.1; found: 398.0.

Step 2: 5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one

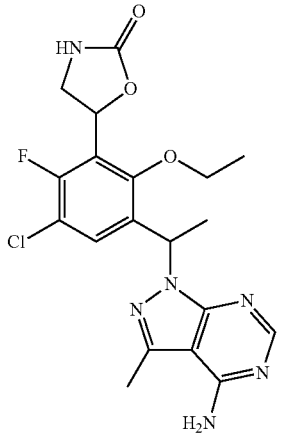 [SMILES: CCOc1c(C(C)n2nc(C)c3c(N)ncnc32)cc(Cl)c(F)c1C1CNC(=O)O1]

The desired single enantiomer (peak 3) was prepared using the same procedure as Example 353, steps 8-12 of U.S. Pat. No. 9,199,982, except that the intermediate from step 1 in this example was racemic and thus the final separation of the four diastereomers occurred in step 12. Chiral purification on Phenomenex Lux Cellulose C-4, 21×250 mm (Chiral Technologies), 5 micron particle size, at flow rate of 18 mL/min using 30% ethanol in hexanes gave the peak 1: Example 2A (single enantiomer) (retention time=12.7 minutes), peak 2: Example 2B (single enantiomer) (retention time=14.2 minutes), peak 3: Example 2C (single enantiomer) (retention time=20.3 minutes), and peak 4: Example 2D (single enantiomer) (retention time=28.9 minutes); the most active enantiomer was peak 3. LCMS calculated for $C_{19}H_{21}ClFN_6O_3$ (M+H)$^+$: m/z=435.1; found: 435.1. $^1$H NMR (500 MHz, DMSO-d$_6$): δ 8.15 (s, 1H), 7.81 (s, 1H), 7.71 (d, 1H), 7.26 (bs, 1H), 6.23 (m, 1H), 5.84 (t, 1H), 3.92 (m, 1H), 3.83 (m, 1H), 2.52 (s, 3H), 1.75 (d, 3H), 1.40 (m, 3H).

Example A1: PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5) P3 Detector Protein is purchased from Echelon Biosciences (Salt Lake City, UT). AlphaScreen™ GST Detection Kit including donor and acceptor beads was purchased from PerkinElmer Life Sciences (Waltham, MA). PI3Kδ (p110δ/p85α) is purchased from Millipore (Bedford, MA). ATP, MgCl$_2$, DTT, EDTA, HEPES and CHAPS are purchased from Sigma-Aldrich (St. Louis, MO).

AlphaScreen™ Assay for PI3Kδ

The kinase reaction are conducted in 384-well REMP plate from Thermo Fisher Scientific in a final volume of 40 µL. Inhibitors are first diluted serially in DMSO and added to the plate wells before the addition of other reaction components. The final concentration of DMSO in the assay is 2%. The PI3K assays are carried out at room temperature in 50 mM HEPES, pH 7.4, 5 mM MgCl$_2$, 50 mM NaCl, 5 mM DTT and CHAPS 0.04%. Reactions are initiated by the addition of ATP, the final reaction mixture consisted of 20

µM PIP2, 20 µM ATP, 1.2 nM PI3Kδ are incubated for 20 minutes. 10 µL of reaction mixture are then transferred to 5 µL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 µL AlphaScreen™ donor and acceptor beads suspended in quench buffer containing 25 nM PI(3,4,5)P3 detector protein. The final concentration of both donor and acceptor beads is 20 mg/ml. After plate sealing, the plate are incubated in a dark location at room temperature for 2 hours. The activity of the product is determined on Fusion-alpha microplate reader (Perkin-Elmer). $IC_{50}$ determination is performed by fitting the curve of percent control activity versus the log of the inhibitor concentration using the GraphPad Prism 3.0 software.

Example A2: PI3K Enzyme Assay

Materials

Lipid kinase substrate, phosphoinositol-4,5-bisphosphate (PIP2), are purchased from Echelon Biosciences (Salt Lake City, UT). PI3K isoforms α, β, δ and γ are purchased from Millipore (Bedford, MA). ATP, $MgCl_2$, DTT, EDTA, MOPS and CHAPS are purchased from Sigma-Aldrich (St. Louis, MO).

The kinase reaction are conducted in clear-bottom 96-well plate from Thermo Fisher Scientific in a final volume of 24 µL. Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM $MgCl_2$, 5 mM DTT and CHAPS 0.03%. The reaction mixture is prepared containing 50 µM PIP2, kinase and varying concentration of inhibitors. Reactions are initiated by the addition of ATP containing 2.2 µCi $[\gamma-^{33}P]ATP$ to a final concentration of 1000 µM. The final concentration of PI3K isoforms α, β, δ and γ in the assay were 1.3, 9.4, 2.9 and 10.8 nM, respectively. Reactions are incubated for 180 minutes and terminated by the addition of 100 µL of 1 M potassium phosphate pH 8.0, 30 mM EDTA quench buffer. A 100 µL aliquot of the reaction solution are then transferred to 96-well Millipore MultiScreen IP 0.45 µm PVDF filter plate (The filter plate is prewetted with 200 µL 100% ethanol, distilled water, and 1 M potassium phosphate pH 8.0, respectively). The filter plate is aspirated on a Millipore Manifold under vacuum and washed with 18×200 µL wash buffer containing 1 M potassium phosphate pH 8.0 and 1 mM ATP. After drying by aspiration and blotting, the plate is air dried in an incubator at 37° C. overnight. Packard TopCount adapter (Millipore) is then attached to the plate followed with addition of 120 µL Microscint 20 scintillation cocktail (Perkin Elmer) in each well. After the plate sealing, the radioactivity of the product is determined by scintillation counting on Topcount (Perkin-Elmer). $IC_{50}$ determination is performed by fitting the curve of percent control activity versus the log of the inhibitor concentration using the GraphPad Prism 3.0 software.

Example A3: PI3Kδ Scintillation Proximity Assay

Materials $[\gamma-^{33}P]ATP$ (10 mCi/mL) was purchased from Perkin-Elmer (Waltham, MA). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, UT). PI3Kδ (p110δ/p85α) was purchased from Millipore (Bedford, MA). ATP, $MgCl_2$, DTT, EDTA, MOPS and CHAPS were purchased from Sigma-Aldrich (St. Louis, MO). Wheat Germ Agglutinin (WGA) YSi SPA Scintillation Beads was purchased from GE healthcare life sciences (Piscataway, NJ).

The kinase reaction was conducted in polystyrene 384-well matrix white plate from Thermo Fisher Scientific in a final volume of 25 µL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 µM PIP2, 20 µM ATP, 0.2 µCi $[\gamma-^{33}P]ATP$, 4 nM PI3Kδ. Reactions were incubated for 210 min and terminated by the addition of 40 µL SPA beads suspended in quench buffer: 150 mM potassium phosphate pH 8.0, 20% glycerol. 25 mM EDTA, 400 µM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). $IC_{50}$ determination was performed by fitting the curve of percent control activity versus the log of the inhibitor concentration using the GraphPad Prism 3.0 software. $IC_{50}$ data for the Examples is presented in Table B as determined by Assay A.

TABLE B

| Example # | PI3Kδ SPA $IC_{50}$ (nM)* |
|---|---|
| 1A | +++ |
| 1B | + |
| 1C | + |
| 1D | +++ |
| 2A | +++ |
| 2B | +++ |
| 2C | + |
| 2D | +++++ |

*column symbols:
+ refers to ≤10 nM
++ refers to >10 nM to 50 nM
+++ refers to >50 nM to 200 nM
++++ refers to >200 nM to 500 nM
+++++ refers to >500 nM Example B1: B Cell Proliferation Assay To acquire B cells, human PBMC are isolated from the peripheral blood of normal, drug free donors by standard density gradient centrifugation on Ficoll-Hypague (GE Healthcare, Piscataway, NJ) and incubated with anti-CD19 microbeads (Miltenyi Biotech, Auburn, CA). The B cells are then purified by positive immunosorting using an autoMacs (Miltenyi Biotech) according to the manufacture's instruction.

The purified B cells ($2 \times 10^5$/well/200 µL) are cultured in 96-well ultra-low binding plates (Corning, Corning, NY) in RPMI1640, 10% FBS and goat F(ab')2 anti-human IgM (10 µg/ml) (Invitrogen, Carlsbad, CA) in the presence of different amount of test compounds for three days. [$^3$H]-thymidine (1 µCi/well) (PerkinElmer, Boston, MA) in PBS is then added to the B cell cultures for an additional 12 hours before the incorporated radioactivity is separated by filtration with water through GF/B filters (Packard Bioscience, Meriden, CT) and measured by liquid scintillation counting with a TopCount (Packard Bioscience).

Example B2: Pfeiffer Cell Proliferation Assay

Pfeiffer cell line (diffuse large B cell lymphoma) are purchased from ATCC (Manassas, VA) and maintained in the culture medium recommended (RPMI and 10% FBS). To measure the anti-proliferation activity of the compounds, the Pfeiffer cells are plated with the culture medium ($2 \times 10^3$ cells/well/per 200 μl) into 96-well ultra-low binding plates (Corning, Corning, NY), in the presence or absence of a concentration range of test compounds. After 3-4 days, [$^3$H]-thymidine (1 μCi/well) (PerkinElmer, Boston, MA) in PBS is then added to the cell culture for an additional 12 hours before the incorporated radioactivity is separated by filtration with water through GF/B filters (Packard Bioscience, Meridenj, CT) and measured by liquid scintillation counting with a TopCount (Packard Bioscience). $IC_{50}$ data for select compounds is presented in Table C.

TABLE C

| Example # | Pfeiffer $IC_{50}$ (nM)* |
|---|---|
| 1B | + |
| 1C | + |
| 2C | + |

* column symbols:
+ refers to ≤ 10 nM
++ refers to >10 nM to 50 nM

Example C: Akt Phosphorylation Assay

Ramos cells (B lymphocyte from Burkitts lymphoma) are obtained from ATCC (Manassas, VA) and maintained in RPMI1640 and 10% FBS. The cells ($3 \times 10^7$ cells/tube/3 mL in RPMI) are incubated with different amounts of test compounds for 2 hrs at 37° C. and then stimulated with goat F(ab')2 anti-human IgM (5 μg/mL) (Invitrogen) for 17 minutes in a 37° C. water bath. The stimulated cells are spun down at 4° C. with centrifugation and whole cell extracts are prepared using 300 μL lysis buffer (Cell Signaling Technology, Danvers, MA). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Example D: Pfeiffer Model of Lymphoma

Methods

Female SCID mice, (5 to 8 weeks of age, Charles River Laboratories, Wilmington, MA) were inoculated with 1×107 tumor cells (Pfeiffer, ATCC #CRL-2632, Manassas, VA) and matrigel (BD Biosciences #354234) in 0.2 mL sterile saline. The inoculation was performed subcutaneously on the flank. Tumor tissue fragments (approximately 3 mm×3 mm) were collected 3 to 6 weeks after the inoculation of cultured cells and implanted subcutaneously in lieu of cellular inoculation. Tissue fragments were implanted as solid pieces using blunt-tip forceps. The treatment of tumor bearing mice was started 15 to 25 days after tumor inoculation, depending upon the tumor size. Animals were sorted to obtain roughly equivalent mean tumor volumes in each group. Minimum mean tumor volume in all groups was 150 mm3 on the first day of treatment and groups consisted of 7 animals. Experimental therapeutic agent, Example 347, was administered to mice orally (PO). Treatment frequency was 2 times daily for a minimum of 14 days for efficacy. The size of subcutaneous tumors was measured 2 to 3 times weekly using a digital caliper. The tumor volume was calculated by measuring the tumor in 2 dimensions and utilizing the equation: Volume=[Length×(Width2)]/2; where the larger number was length, and the smaller number width. If multiple tumors were formed, the final volume was the sum of the individual tumors subject to the same equation: eg, 2 tumors; Volume={[L1×(W1)2]/2}+{[L2×(W2)2]/2}. Effects on tumor growth were reported as percent tumor growth inhibition (% TGI). Percent TGI was calculated with the equation: (1−(Tx vol./control vol.))*100, where control volume was the vehicle or untreated tumor volume on a given day, and Tx volume was any treatment group tumor volume on that same day. Statistical differences between treatment and vehicle controls were assessed using ANOVA: Single Factor test.

Results (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one (see Example 1) was evaluated as a single agent in the Pfeiffer human tumor xenograft model of diffuse large B-cell lymphoma, a subtype of NHL. Pfeiffer cancer cells were shown to be sensitive to the anti-proliferative effects of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one in vitro. Therefore, a tumor model was established based on subcutaneous inoculation of tumor cells into immune compromised SCID mice and tumor-bearing mice received twice daily oral doses of vehicle or (R)-4-(3-((5)-1-(4-amino-3-methyl-1H-pyrazolo[3,4-d]pyrimidin-1-yl)ethyl)-5-chloro-2-ethoxy-6-fluorophenyl)pyrrolidin-2-one at 0.3, 1, 3, or 10 mg/kg for 14 days. (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one treatment inhibited tumor growth by 22%, 24%, 36%, and 58% (percent tumor growth inhibition) with increasing dose (see e.g., U.S. Pat. No. 9,932,341).

Example E: Dose-Escalation & Dose Expansion Studies

In the dose-escalation and dose-expansion studies described herein, the PK, PD, safety, and efficacy of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt (i.e., Compound 1C) (were evaluated in patients with relapsed or refractory B-cell malignancies. The PK characteristics of Compound 1C combined with the absence of dose-limiting toxicities (DLTs) permitted exposure levels that exceeded the $IC_{90}$ throughout the once-daily (QD) dosing interval at all doses tested. In addition, the results of a food effect analysis indicated that Compound 1C may be dosed without regard to timing of meals. The near-maximal inhibition of pAKT in the ex vivo PD assay were consistent with exposure data. Results of the PI3Kδ monotherapy and combination therapies are discussed below in Examples F-H.

Study Design and Patients

The dose-escalation and dose-expansion study was conducted in multiple parts: dose escalation of Compound 1C monotherapy (Part 1) followed by Cohort expansion (Part 3); Compound 1C+itacitinib dose escalation (Part 2) followed by Cohort expansion (Part 3); and Compound 1C+R-ICE (rituximab plus ifosfamide, carboplatin, and etoposide) dose evaluation and expansion (Part 6) (NCT02018861). Eligible patients (age ≥18 years) had diagnosed lymphoid malignancies of B-cell origin, including indolent or aggressive B-cell NHL malignancies, transformed NHL histologies, and Hodgkin lymphoma (HL), that had relapsed or were refractory to prior standard therapy. Patients with Burkitt lymphoma and precursor B-lymphoblastic leukemia/lymphoma were excluded. Eligible patients had Eastern Cooperative Oncology Group performance status (ECOG PS)≤1 (dose escalation) or ≤2 (dose expansion); had adequate cardiac, liver, and kidney function; had life expectancy ≥12 weeks; had received ≥1 prior treatment regimen; and had not responded to or were not candidates for hematopoietic (H)SCT or other potentially curative therapy.

Patients were excluded if they had a history of untreated, symptomatic, or unstable brain metastases; spinal cord compression; lymphoma involving the central nervous system (permitted in the Compound 1C monotherapy expansion cohort A [B-cell malignancies] and Compound 1C+itacitinib combination expansion cohort); or received allogeneic hematopoietic stem cell transplant (HSCT) within 6 months or autologous HSCT within 3 months of enrollment. Prior treatment with PI3Kδ inhibitors was excluded for Compound 1C monotherapy cohorts unless approved by the medical monitor, and prior JAK inhibitors were excluded for Compound 1C+itacitinib combination therapy cohorts.

72 patients were enrolled and treated with Compound 1C monotherapy (median age, 66 [range, 30-89] years) (Table 1). The median (range) duration of treatment was 4.0 (0.2-22.7) months. At the data cutoff, all but 11 subjects had discontinued study treatment, primarily for disease progression (n=35 [49%]) and adverse events (AEs) (n=14 [19%]).

TABLE 1

Patient demographics and baseline characteristics (ITT)

| Characteristics | Compound 1C Monotherapy (N = 72) | Compound 1C + Itacitinib (N = 11) | Compound 1C + R-ICE (N = 5) |
|---|---|---|---|
| Age, median (range), y | 66 (30-89) | 67 (24-82) | 64 (52-72) |
| Age, >65 y, n (%) | 37 (51) | 7 (64) | 1 (20) |
| Men, n (%) | 41 (57) | 6 (55) | 3 (60) |
| Race, n (%) | | | |
| White/Caucasian | 57 (79) | 9 (82) | 4 (80) |
| Black/African American | 8 (11) | 1 (9) | 0 |
| Asian | 0 | 0 | 0 |
| Other* | 7 (10) | 1 (9) | 1 (20) |
| Disease type, n (%) | | | |
| CLL | 6 (8) | 1 (9) | 0 |
| DLBCL | 23 (32) | 6 (55) | 5 (100) |
| FL | 14 (19) | 1 (9) | 0 |
| HL | 10 (14)† | 2 (18)¶ | 0 |
| MCL | 9 (13) | 1 (9) | 0 |
| MZL | 9 (13)‡ | 0 (0) | 0 |
| WM | 1 (1) | 0 (0) | 0 |
| Duration since prior diagnosis, median (range), y | 4.95 (0.5-22.5) | 3.2 (0.4-13.2) | 0.8 (0.5-6.3) |
| ≥3 prior systemic therapy regimens, n (%) | 39 (54) | 5 (45) | 0 |
| Prior HSCT, n (%) | 21 (29) | 1 (9) | 0 |

*Includes American-Indian, Alaska Native, Pacific Islander, and other.
†Includes classic HL (n = 9) and nodular lymphocytic-predominant HL (n = 1).
‡Includes extranodal MZL of MALT type (n = 2), nodal MZL (n = 4), splenic MZL (n = 2), and unknown MZL subtype (n = 1).
¶Includes classic HL (n = 2).
CLL, chronic lymphocytic leukemia;
DLBCL, diffuse large B-cell lymphoma;
FL, follicular lymphoma;
HL, Hodgkin lymphoma;
HSCT, hematopoietic stem cell transplant;
MALT, mucosa-associated lymphatic tissue;
MCL, mantle cell lymphoma;
MZL, marginal zone lymphoma;
R-ICE, rituximab plus ifosfamide, carboplatin, and etoposide;
WM, Waldenström macroglobulinemia.

Dosing

For Compound 1C monotherapy, Compound 1C was self-administered orally, once daily (QD). Compound 1C was administered in a fasted state, except for patients participating in an optional food-effect cohort, until a protocol amendment allowed administration without regard to food. Treatment continued until unacceptable toxicity or disease progression. During dose escalation (see Table 2C), an initial single-patient cohort was treated with 5 mg QD and subsequent cohorts were enrolled using a 3+3 design, to identify any dose-limiting toxicities (DLTs; defined in Table 2A) within the 21-day observation period. If DLTs occurred in >1 of the first 3 patients or the total cohort of 6 patients, then the maximum tolerated dose (MTD) was deemed to be exceeded and the next lower tolerable dose level was defined as the MTD. All doses up to 45 mg QD were well tolerated over the DLT observation period of 21 days and therefore no MTD was identified. However, incidences of colitis were observed over the longer term (>3 months), which prompted a change in dosing regimen. The protocol was amended to include a modified dosing schedule wherein daily dosing was followed by weekly dosing, based on a PK simulation (see Discussion). Patients enrolled on or after this protocol amendment received Compound 1C 20 mg QD for the first 9 weeks followed by Compound 1C 20 mg once weekly (QW); patients who had already received Compound 1C 20 mg QD for ≥9 weeks were switched to the QW schedule. Per protocol amendment, ongoing and newly enrolled patients were required to take prophylactic treatment for *Pneumocystis jiroveci* pneumonia (PJP).

TABLE 2A

Definition of dose-limiting toxicity

Nonhematologic

≥Grade 3 nonhematologic toxicity, excluding nausea, vomiting, diarrhea
≥Grade 3 nausea, vomiting, or diarrhea uncontrolled by maximal antiemetic/antidiarrheal therapy lasting >48 hours
Any toxicity considered a DLT in the opinion of the investigator and medical monitor Hematologic Grade 4 neutropenia lasting ≥7 days*
Febrile neutropenia (ANC <1.0 × 10$^9$/L with a single temperature of >38.3° C. (101° F.) or a sustained temperature of ≥38° C. (100.4° F.) for more than 1 hour
Grade 3 thrombocytopenia associated with clinically significant bleeding (clinically significant as determined by the investigator or resulting in the need for a transfusion of red blood cells)
Grade 4 thrombocytopenia lasting >7 days
Grade 4 anemia General Any specific AE that results in a dose delay or reduction in >one-third of subjects

*Itacitinib can cause transient decreases in white blood cells due to margination; therefore, DLT rules required neutropenia to persist after holding itacitinib for 2 to 3 days. Where the clinical status of the subject allowed, investigators were encouraged to wait 24 hours before starting growth factors, to determine if white blood cell margination was contributing to the degree of neutropenia.
AE, adverse event;
ANC, absolute neutrophil count;
DLT, dose-limiting toxicity.

For the Compound 1C+itacitinib combination, dose escalation of Compound 1C proceeded using 3+3 design, starting with an Compound 1C dose approximately 25% less than the recommended dose determined for Compound 1C monotherapy. Criteria for itacitinib dose interruption are summarized in Table 2A. For each cohort, itacitinib was co-administered at a dose of 300 mg QD.

For the Compound 1C+R-ICE combination, dose escalation of Compound 1C proceeded using 3+3 design with a starting dose approximately 25% below the recommended dose determined for Compound 1C. R-ICE chemotherapy components were administered either according to institutional practice or per protocol.

Assessments

Patients were assessed on Days 1, 8, and 15 of Cycle 1 and Day 1 (±3) of each subsequent treatment cycle. A schedule of key study assessments is shown in Table 2B.

TABLE 2B

Study Assessments

| | Screening | Treatment | | | | | Follow-up EOT + |
|---|---|---|---|---|---|---|---|
| | | Cycle 1 | | | Other cycles | | |
| | Days −30 to −1 | Day 1 | Day 8 (±3 days) | Day 15 (±3 days) | Day 1 (±3 days) | EOT | 30 to 37 days |
| Prior/concomitant medications | X | X | X | X | X | X | X |
| Physical examination | X | X | X | X | X | X | X |
| Vital signs | X | X | X | | X | X | X |
| 12-lead ECG | X | X | | X | X | X | X |
| Laboratory tests | X | X | X | X | X | X | X |
| ECOG PS | X | X | X | X | X | X | X |
| CT/MRI | X | | | | X* | X | |
| FDG-PET | X | | | | X*† | X | |
| Bone marrow examination | X | | | | X‡ | | |
| Review AEs | X | X | X | X | X | X | X |
| Serum chemistry/hematology | X | X | X | X | X | X | X |
| Blood PK sample | | X | X§ | X | X§‖ | | |
| Blood PD sample | | X | | X | X¶ | | |
| Tumor tissue sample | X# | | | | X** | X** | |

*Every 9 weeks (3 cycles) or at a frequency consistent with the standard of care; performed only if measurable disease is present.
†May be performed per standard of care; applicable for lymphomas only. To confirm a CR. Not collected from patients receiving Compound 1C + R-ICE.
‖Cycle 2 only; collected from patients with B-cell malignancies in the Compound 1C monotherapy expansion cohort (cohort A).
¶Through Cycle 6 for Compound 1C monotherapy and Compound 1C + itacitinib combination, and in Cycles 3, 6, 9, and 12 for Compound 1C + R-ICE combination.
Archival tissue acceptable; for patients with CLL, peripheral blood acceptable.
**Optional on-treatment or EOT biopsy (or peripheral blood for patients with CLL).
AE, adverse event; CLL, chronic lymphocytic leukemia;
CR, complete response;
CT, computed tomography;
ECG, electrocardiogram;
ECOG PS, Eastern Cooperative Oncology Group performance status;
EOT, end of treatment;
FDG-PET, fluorodeoxyglucose (FDG)-positron emission tomography;
MRI, magnetic resonance imaging;
PD, pharmacodynamic;
PK, pharmacokinetic;
R-ICE, rituximab plus ifosfamide, carboplatin, and etoposide.

The primary endpoint was safety and tolerability of Compound 1C monotherapy, Compound 1C+itacitinib, or Compound 1C+R-ICE as assessed by summary of treatment-emergent adverse events (TEAEs), clinical laboratory assessments, physical examination results, and 12-lead electrocardiograms. The severity of TEAEs was assessed using Common Terminology Criteria for Adverse Events version 4.03.

The secondary endpoints were efficacy and PK. Efficacy was measured by best overall response rate (ORR), defined as the proportion of patients achieving a partial response (PR) or complete response (CR). Response was evaluated (per investigator's assessment) every 9 weeks based on the Lugano classification of lymphoma response criteria for HL and NHL (Cheson B. D. et al, *Journal of Clinical Oncology*, 2014; 32(27):3059-3067), the International Working Group on Chronic Lymphocytic Leukemia criteria for chronic lymphocytic leukemia (CLL) (Hallek M. et al, *Blood*, 2008; 111(12):5446-5456; Cheson B. D. et al, *J Clin Oncol*, 2012; 30(23):2820-2822)), and the VIth International Workshop on Waldenström Macroglobulinemia response assessment for Waldenström Macroglobulinemia (WM) (Owen R. G. et al, *Br J Haematol*, 2013; 160(2):171-176). If the patient's response to treatment was assessed by PET and CT/MRI, then the PET result was used for response endpoints; CT/MRI result was used for an assessment if PET result was not available for the assessment; CT/MRI was used for response endpoints if it was the only form of assessment available for the patient.

Exploratory endpoints included: duration of response (DOR, duration of time from first response to death or disease progression, whichever occurred first); progression free survival (PFS, duration of time from first study dose to death or disease progression, whichever occurred first); population PK; pharmacodynamic (PD) relationship between PI3Kδ inhibition (as determined by an ex vivo phosphorylated AKT [pAKT] assay).

Statistical Methods

Safety, tolerability, and efficacy analyses were performed on the safety/intent-to-treat population, which included all enrolled patients who received ≥1 dose of Compound 1C, itacitinib, or any of the R-ICE components. PK and PD analyses included all patients in the safety/intent to treat population with available PK/PD data. All statistical analyses were exploratory in nature and were summarized using descriptive statistics. ORRs were estimated with 95% confidence intervals (CIs) calculated based on the exact method for binomial distributions. Kaplan-Meier estimates of median DOR and PFS were presented with their respective 95% CIs.

Additional Patient Exclusion Criteria

Additional patient exclusion criteria included radiation treatment within 4 weeks, investigational study drug within 28 days (or 5 half-lives, whichever is longer), approved anticancer drugs (except steroids at ≤10 mg prednisone daily) within 21 (42 for nitrosoureas) days (or 5 half-lives, whichever is longer), unresolved toxicity grade ≥2, current or recent history of clinically meaningful infection, total bilirubin ≥1.2×upper limit of normal (ULN), alkaline phosphatase ≥2.5×ULN, aspartate aminotransferase (AST) or alanine aminotransferase (ALT) ≥2.0×ULN, or creatinine clearance <50 mL/min based on Cockroft-Gault formula.

Per Protocol R-ICE Dosing Schedule

Per protocol, R-ICE was administered in 3 21-day cycles, according to the following schedule: rituximab 375 mg/m² on Days 1 and 2 of Cycle 1, and Day 1 of Cycles 2 and 3; ifosfamide 5000 mg/m² by continuous intravenous (IV) infusion over 24 h on Day 3 of each cycle; carboplatin (area under the curve=5 mg/mL; maximum dose 800 mg) by IV infusion on Day 3; etoposide 100 mg/m² by IV on days 3 to 5.

Example F. PI3Kδ Inhibitor Monotherapy

This analysis includes data from patients enrolled into Compound 1C monotherapy dose-escalation (5-45 mg QD) and expansion (20 mg QD and 30 mg QD) cohorts.

Dose Escalation and Cohort Expansion

The number of patients per dose level during Compound 1C monotherapy dose escalation and expansion is shown in Table 2C. No DLTs were identified, the MTD was not reached, and the 20 mg QD and 30 mg QD doses were expanded.

TABLE 2C

Monotherapy Dose Escalation and Cohort Expansion

| Dose | 5 mg | 10 mg | 15 mg | Expansion doses | | |
|---|---|---|---|---|---|---|
| | | | | 20 mg | 30 mg | 45 mg |
| n | 1 | 3 | 3 | 34 | 27 | 4 |
| Escalation rules | In case of a | If 1 DLT was observed in the first 3 patients, 3 additional patients were to be | | | | |

TABLE 2C-continued

Monotherapy Dose Escalation and Cohort Expansion

| Dose | 5 mg | 10 mg | 15 mg | Expansion doses | | |
|---|---|---|---|---|---|---|
| | | | | 20 mg | 30 mg | 45 mg |
| grade ≥2 AE, the cohort was to be expanded to 3 patients | enrolled in the cohort; if DLTs occurred in >1 of the first 3 patients or the total cohort of 6 patients, then the MTD was deemed to be exceeded | | | | | |

AE = adverse event;
DLT = dose limiting toxicity;
MTD = maximum tolerated dose.

Pharmacokinetics and Pharmacodynamics of Compound 1C

Figure 1B:
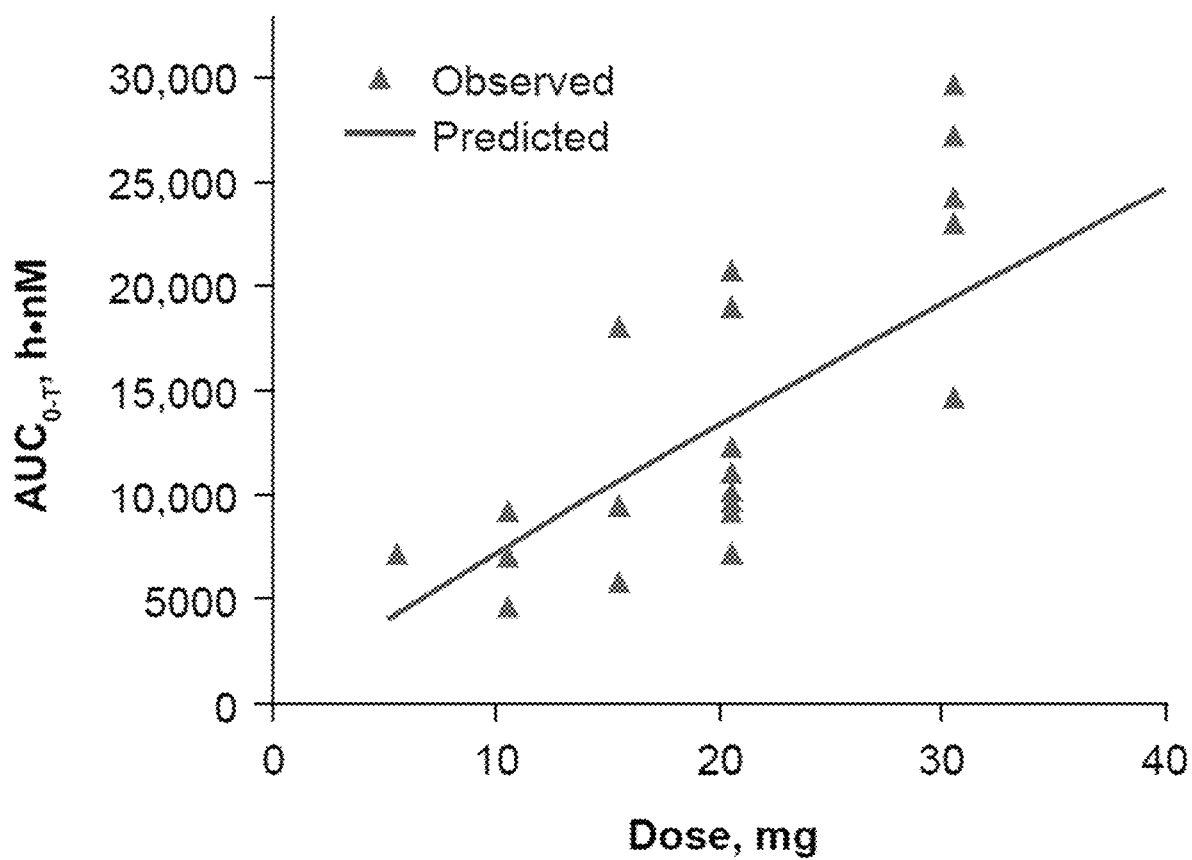

All doses tested remained above the $IC_{90}$ for target inhibition throughout the dosing interval, as shown in FIG. 1A; $C_{max}$ and $G_{trough}$ resulting from a 20 mg QD dose of Compound 1C were 16-fold and 2-fold above the $IC_{90}$ for pAKT inhibition, respectively. A PK simulation conducted to support selection of a 20 mg QW dosing schedule estimated that serum Compound 1C levels resulting from this schedule would exceed the $IC_{90}$ for target inhibition for ~36 hours and would have minimal to no inhibition for approximately half of the dosing interval. Following multiple-dose administration of Compound 1C alone, Compound 1C attained peak plasma concentrations rapidly, with a median $t_{max}$ of 0.5 to 1 hour. Subsequently, Compound 1C plasma concentrations declined in a monophasic fashion with a mean terminal-phase disposition $t_{1/2}$ of 8.6 to 11.5 hours. Dose proportionality appeared to be observed between 5 and 45 mg QD at steady state, as shown in FIG. 1B.

Food effect was analyzed in 12 patients. Although co-administration of Compound 1C with high fat meal decreased $C_{max}$ by 42% compared with the fasted state, it had a modest effect on area under the curve (AUC; 10% decrease). The fed versus fasted geometric mean ratio for AUC was 0.90 (90% CI: 0.68-1.18).

Figure 4:
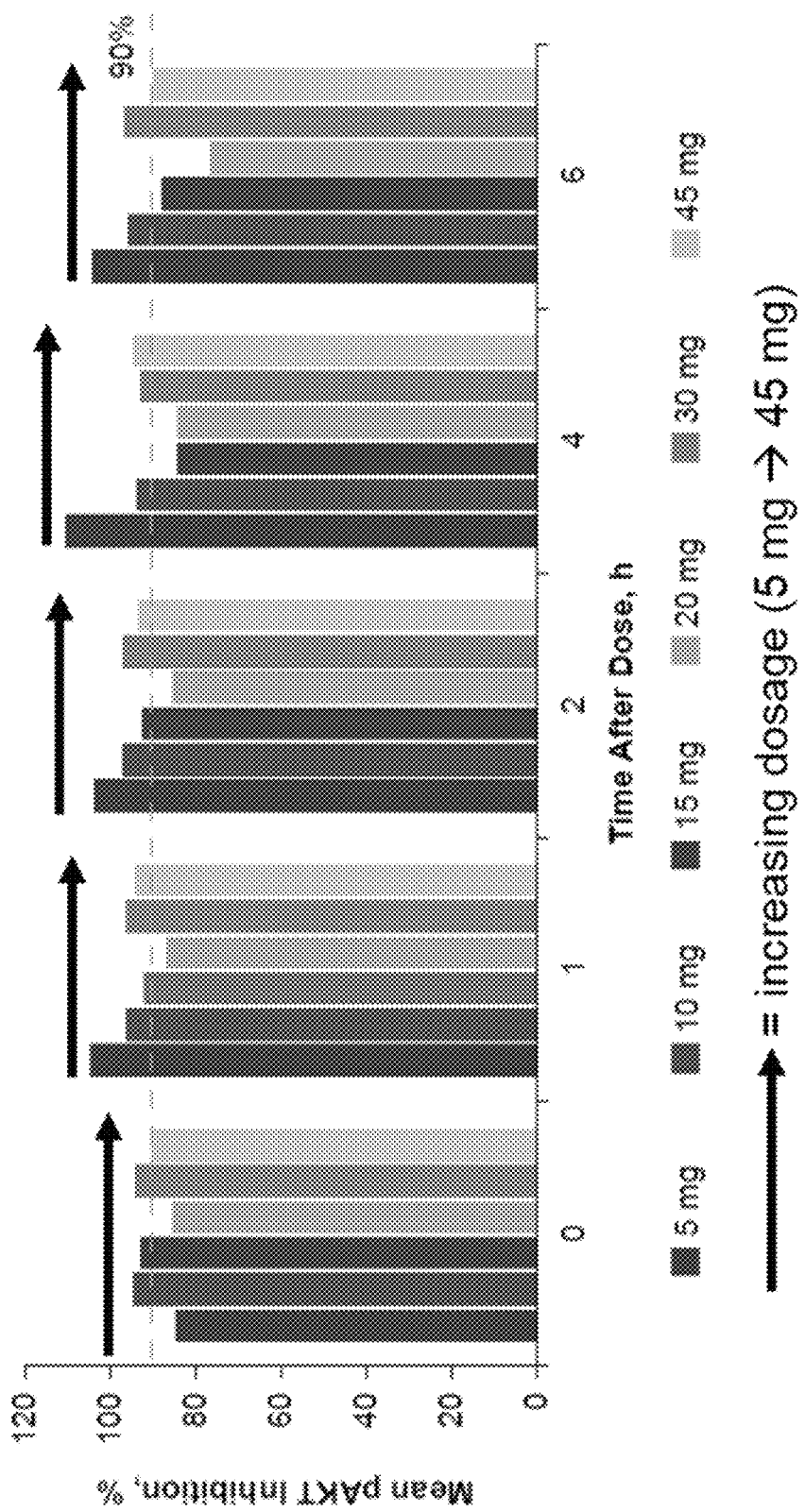
FIG. 4 shows Mean percent inhibition of phosphorylated AKT at steady state. Compound 1C was dosed once daily and levels of phosphorylated AKT (pAKT; Ser473) were measured by flow cytometry in SU-DHL cells added to patient whole blood after Compound 1C treatment on day 15 of cycle 1.

Near-maximal PI3Kβ inhibition was observed at all Compound 1C doses for up to 6 hours post-dose, as measured by effects on pAKT levels in whole blood, as shown in FIG. 4.

Safety and Tolerability

TEAEs occurring in >10% of patients across all dose cohorts combined and in the 20 mg QD cohort are shown in Table 3.

TABLE 3

Nonhematologic TEAEs occurring in ≥15% of patients receiving Compound 1C monotherapy (Safety Population)

| Preferred Term (MedDRA) | 20 mg* (N = 34), n (%) | | | All doses (N = 72), n (%) | | |
|---|---|---|---|---|---|---|
| | Any Grade | Grade 3 | Grade 4 | Any Grade | Grade 3 | Grade 4 |
| Any TEAE | 32 (94) | 14 (41) | 6 (18) | 68 (94) | 29 (40) | 12 (17) |
| Diarrhea/Colitis† | 12 (35) | 3 (9) | 1 (3) | 26 (36) | 6 (8) | 1 (1) |
| Nausea | 9 (26) | 0 | 0 | 26 (36) | 0 | 0 |
| Fatigue | 10 (29) | 0 | 0 | 22 (31) | 0 | 0 |
| Rash‡ | 10 (29) | 3 (9) | 0 | 22 (31) | 4 (6) | 0 |
| Cough | 5 (15) | 0 | 0 | 17 (24) | 0 | 0 |
| Vomiting | 4 (12) | 0 | 0 | 17 (24) | 0 | 0 |
| Dizziness | 5 (15) | 0 | 0 | 13 (18) | 0 | 0 |
| Pyrexia | 7 (21) | 0 | 0 | 13 (18) | 1 (1) | 0 |
| Hypokalemia | 6 (18) | 1 (3) | 0 | 12 (17) | 1 (1) | 0 |
| Abdominal pain | 6 (18) | 1 (3) | 0 | 11 (15) | 1 (1) | 0 |

TABLE 3-continued

Nonhematologic TEAEs occurring in ≥15% of patients receiving Compound 1C monotherapy (Safety Population)

| Preferred Term (MedDRA) | 20 mg* (N = 34), n (%) | | | All doses (N = 72), n (%) | | |
|---|---|---|---|---|---|---|
| | Any Grade | Grade 3 | Grade 4 | Any Grade | Grade 3 | Grade 4 |
| Constipation | 3 (9) | 0 | 0 | 11 (15) | 0 | 0 |
| Decreased appetite | 6 (18) | 0 | 0 | 11 (15) | 0 | 0 |
| Night sweats | 6 (18) | 0 | 0 | 11 (15) | 0 | 0 |
| Pruritus | 7 (21) | 0 | 0 | 10 (14) | 0 | 0 |
| Back pain | 6 (18) | 0 | 0 | 9 (13) | 0 | 0 |
| Chills | 5 (15) | 0 | 0 | 9 (13) | 0 | 0 |

*Based on starting dose. Includes patients who received QD and QW dosing.
†Includes preferred terms of diarrhea, colitis, enterocolitis, gastrointestinal inflammation, colitis microscopic, and cytomegalovirus colitis.
‡Includes preferred terms of dermatitis exfoliative, rash, rash erythematous, rash macular, rash maculopapular, rash pruritic, exfoliative rash, rash generalized, rash popular, and rash pustular.
MedDRA, Medical Dictionary for Regulatory Activities;
TEAE, treatment-emergent adverse event.

The most common (≥30%) any grade nonhematologic TEAEs in all patients were diarrhea/colitis (36%), nausea (36%), fatigue (31%), and rash (31%). One patient (1%) each experienced grade 3 pneumonitis and grade 3 cytomegalovirus colitis, and 7 patients (10%) experienced pneumonia (grade 3, n=3 [4%]). Treatment-emergent laboratory abnormalities occurring in ≥30% of patients are shown in Table 4. New/worsening of any grade and grade 3/4 neutropenia occurred in 32 patients (44%) and 14 patients (19%), respectively (Table 4). SAEs experienced by >2 patients were diarrhea/colitis (n=9 [13%]), pyrexia (n=4 [6%]), hypotension (n=3 [4%]), and sepsis (n=3 [4%]). Any grade SAEs of infections and infestations (System Organ Class) occurred in 11 patients (15%), including pneumonia in 2 patients (3%).

TABLE 4

New or worsening hematologic laboratory abnormalities occurring in ≥30% of patients receiving Compound 1C monotherapy (Safety Population)*

| Total (N = 72) | Any Grade, n (%) | Grade 3, n (%) | Grade 4, n (%) |
|---|---|---|---|
| Leukopenia | 36 (50) | 6 (8) | 0 |
| Neutropenia | 32 (44) | 10 (14) | 4 (6) |
| Lymphopenia | 25 (35) | 13 (18) | 2 (3) |
| Thrombocytopenia | 25 (35) | 2 (3) | 5 (7) |
| Anemia | 22 (31) | 6 (8) | NA |

*Based on reported laboratory values.
NA, not applicable

Figure 5A:
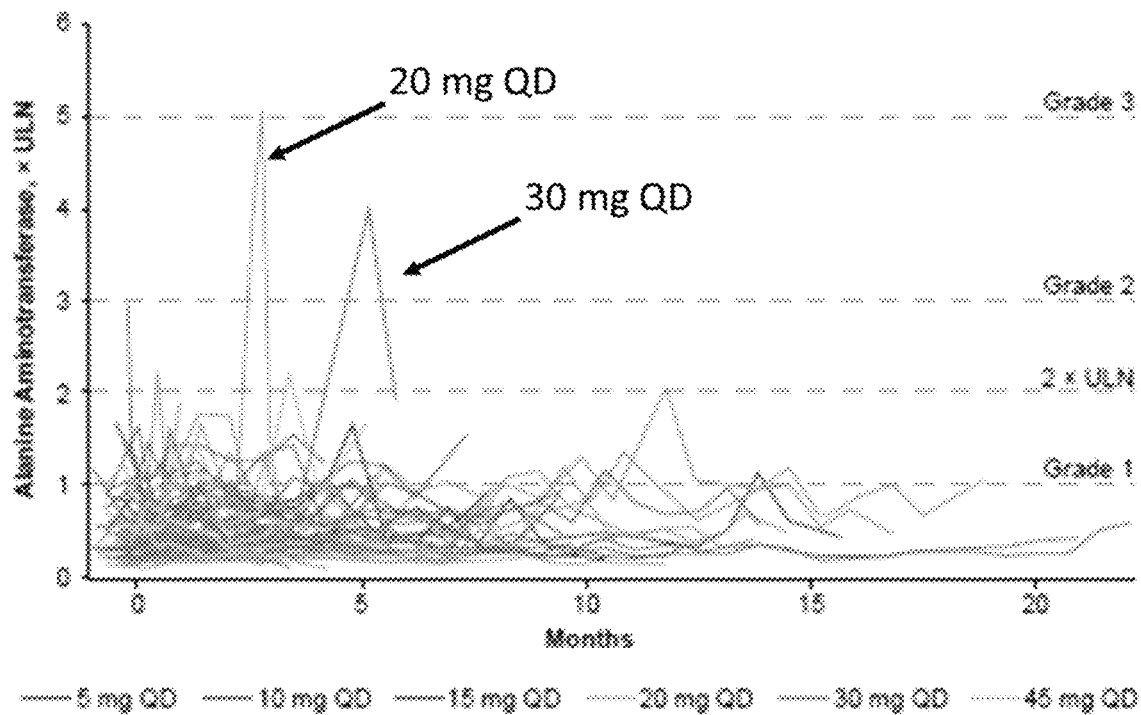
FIGS. 5A-5B shows ALT (FIG. 5A) and AST (FIG. 5B) over time in patients receiving Compound 1C monotherapy. ALT, alanine aminotransferase; AST, aspartate aminotransferase; QD, once daily; ULN, upper limit of normal.
Figure 5B:
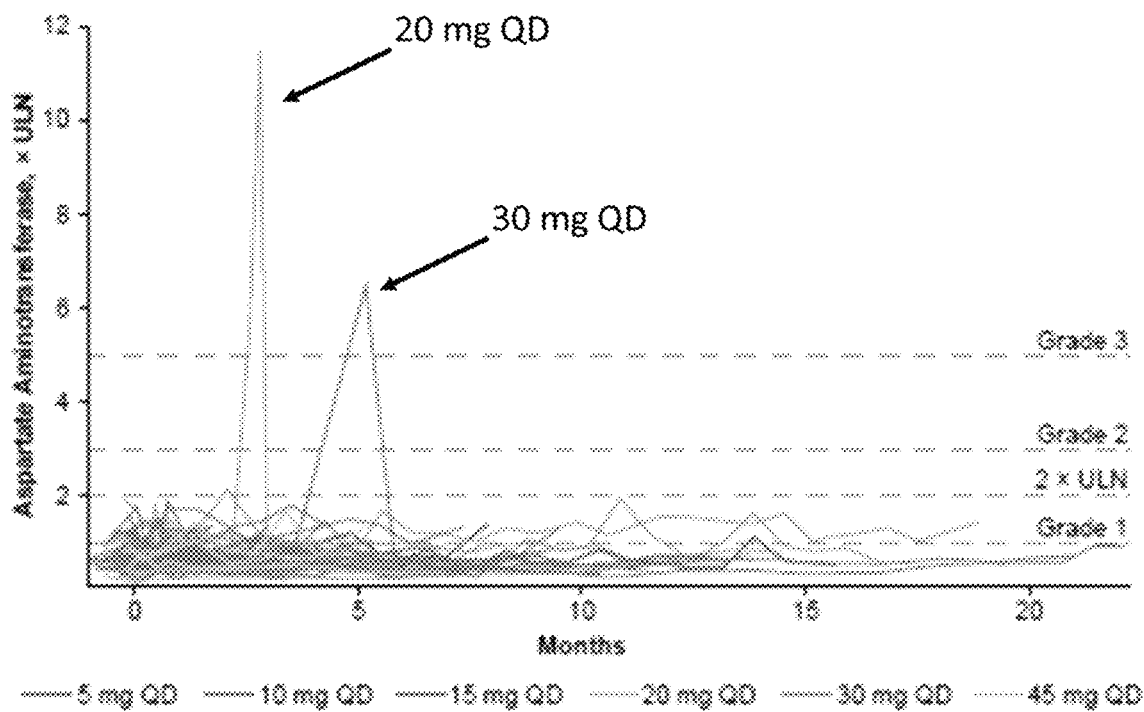

Among TEAEs of interest, the median (range) time to onset of grade 3/4 diarrhea/colitis was 5.7 (1.6-14.9) months and median (range) time to onset of grade 3/4 rash was 2.9 (1.5-9.3) months. AST and ALT elevations occurred in 21 (29%) and 20 (28%) patients, respectively; all events were grade 1, except 4 events in 2 patients (1 patient with 1 event each of grade 3 AST and grade 2 ALT elevation, both occurring >30 days after the last dose of Compound 1C; 1 patient with 1 event each of grade 3 AST and ALT elevation considered secondary to sepsis). Bilirubin elevation occurred in 8 (11%) patients; all events were ≤grade 2 except 1 grade 3 event that occurred >30 days after date of last dose. Changes in AST and ALT levels over time are shown in FIGS. 5A-5B. There were no TEAEs of PJP or bowel perforation. Five patients (7%) experienced hypertension (all grade 1/2); 7 (10%) experienced hyperglycemia (all grade 1/2 except 1 grade 3).

Any grade TEAEs led to Compound 1C dose interruption in 30 patients (42%), dose reduction in 4 patients (6%), and treatment discontinuation in 14 patients (19%). The most common nonhematologic TEAEs leading to Compound 1C dose interruption were diarrhea/colitis (11/72 [15%]) and pyrexia (4/72 [6%]). TEAEs leading to death occurred in 2 patients (respiratory failure, and respiratory failure and sepsis); none was deemed related to Compound 1C.

Long-Term Tolerability and Dosing

Prior to implementation of the QW dosing schedule, 9/31 patients (29%) with DLBCL, FL, MCL, and MZL receiving Compound 1C monotherapy had discontinued due to TEAEs, most commonly (n≥2) diarrhea/colitis (n=3 [10%]), or rash (n=2 [6%]); however, no patient had discontinued due to treatment-related AEs during the first 9 weeks of treatment. As of the data cutoff date, 26 (36%) of the 72 enrolled patients had received QW dosing of Compound 1C (after receiving QD dosing for at least 9 weeks) for a median (range) of 2.5 (1.2-9.6) months and a total of 105 patient-months; 46 patients (64%) received QD dosing only; no patients were still in the first 9 weeks of QD dosing. Four of the 26 patients initiated the QW schedule at a <20 mg dose due to previous dose reductions (1 at 5 mg and 3 at 10 mg). Among the 26 patients who received QW dosing, 8 (31%) had dose interruptions (TEAEs leading to dose interruption in >1 patient were diarrhea and neutropenia [n=2 each]), 1 (4%) had a dose reduction (due to rash pustular), and none discontinued treatment due to a TEAE. Four patients receiving QW dosing (15%) experienced a total of 6 SAEs (abdominal pain, diarrhea, pyrexia, bronchitis, sepsis, and dehydration, n=1 each) during the QW dosing period. No grade 4 nonhematologic TEAEs were reported during QW dosing. Two patients had grade 3 diarrhea and rash (n=1 [4%] each); both events occurred shortly after the switch from QD dosing. No new/worsening grade 4 neutropenia was reported, and one patient reported a new/worsening grade 4 thrombocytopenia during QW dosing.

Efficacy

Figure 2:
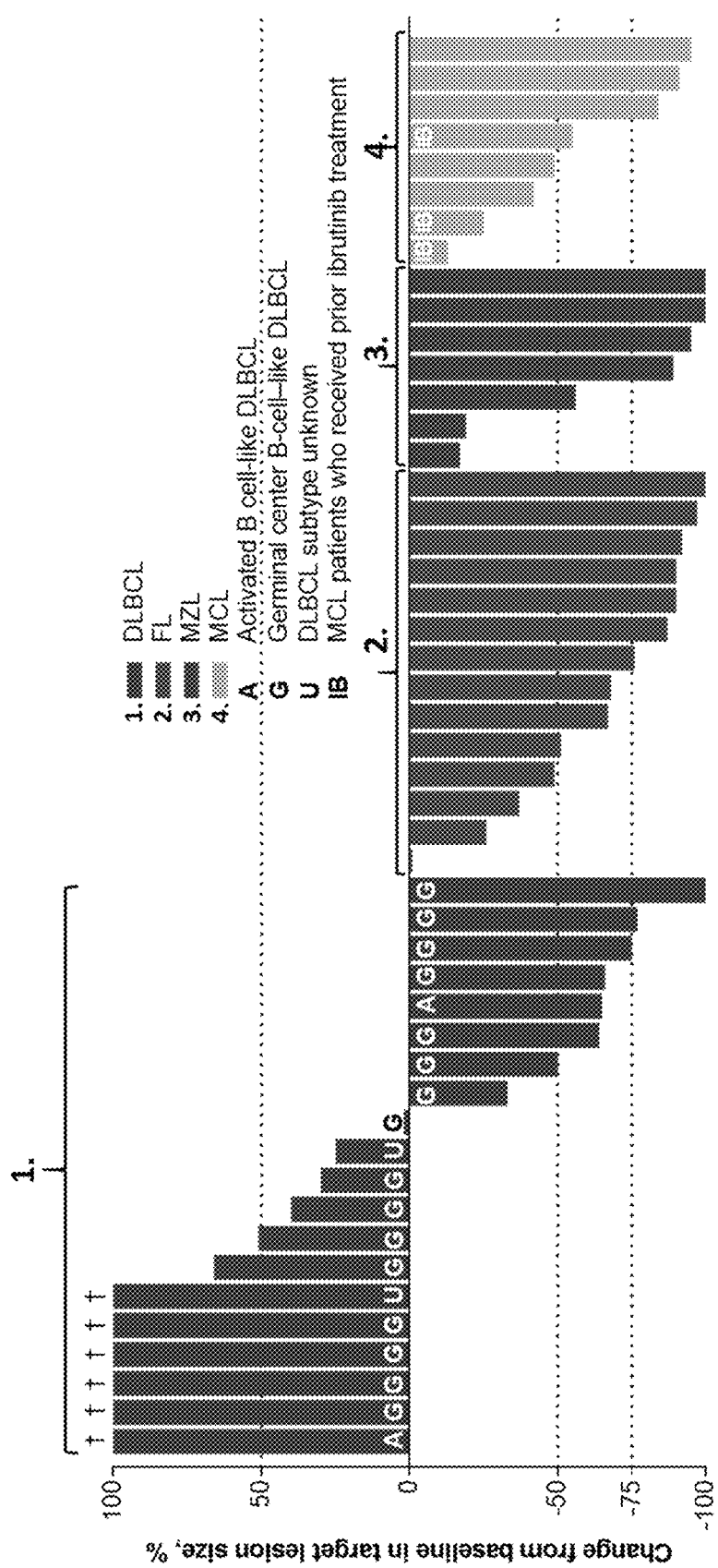
FIG. 2 shows monotherapy best percent change from baseline in target lesion size. *Data for 3 patients with DLBCL, 2 with MZL and 1 with MCL are not shown due to non-measurable disease at baseline or no valid post baseline target lesion measurements. † Best percentage change from baseline in target lesion size >100%. IB, 3 patients with MCL had received ibrutinib before the study, of whom a best overall response of CR or PR was achieved by 2 patients. DLBCL, diffuse large B-cell lymphoma; FL, follicular lymphoma; MCL, mantle cell lymphoma; MZL, marginal zone lymphoma.
Figure 3:
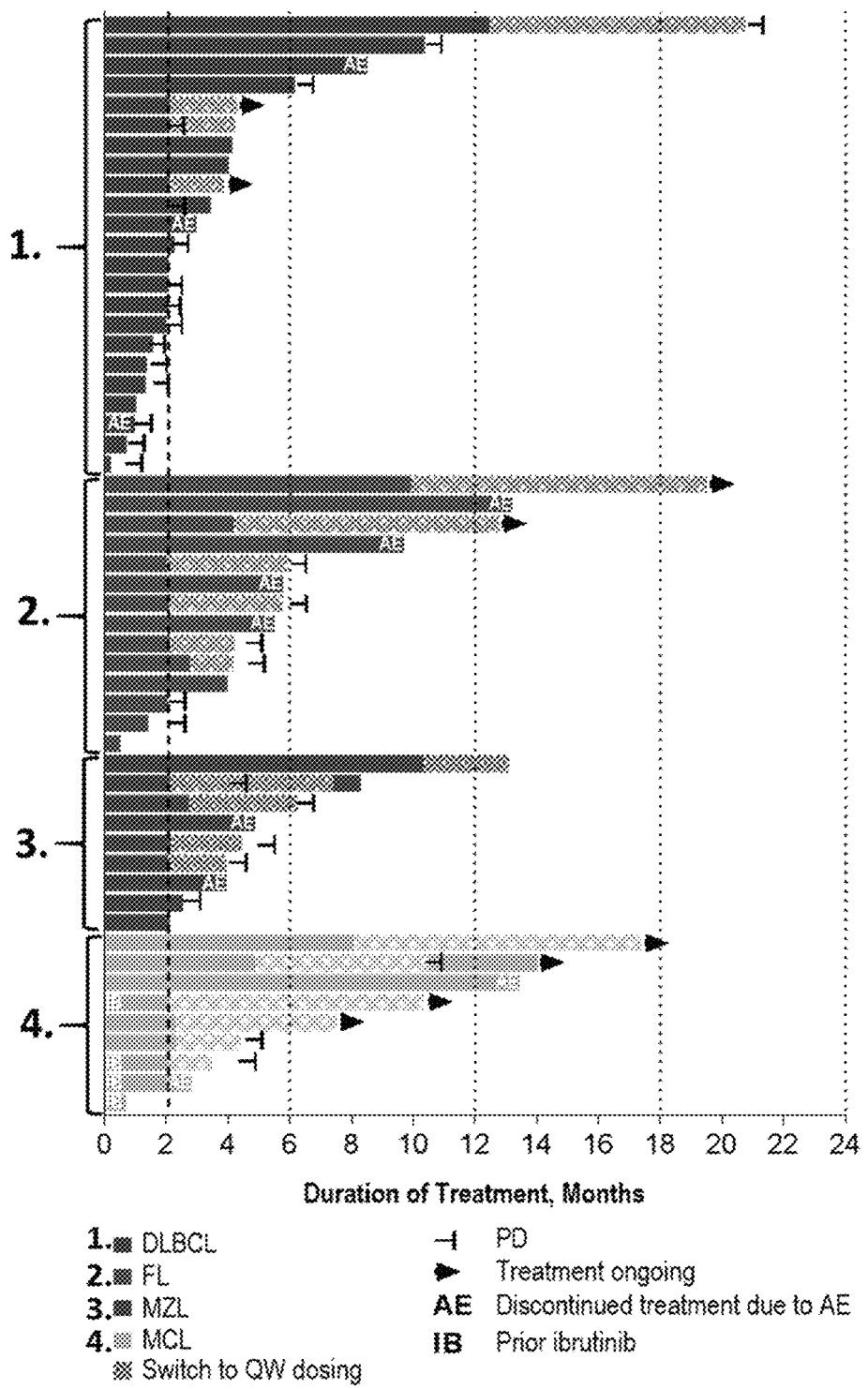
FIG. 3 shows duration of Compound 1C monotherapy treatment. AE, adverse event; DLBCL, diffuse large B-cell lymphoma; FL, follicular lymphoma; MCL, mantle cell lymphoma; MZL, marginal zone lymphoma; PD, progressive disease; QW, once weekly.
Figure 6:
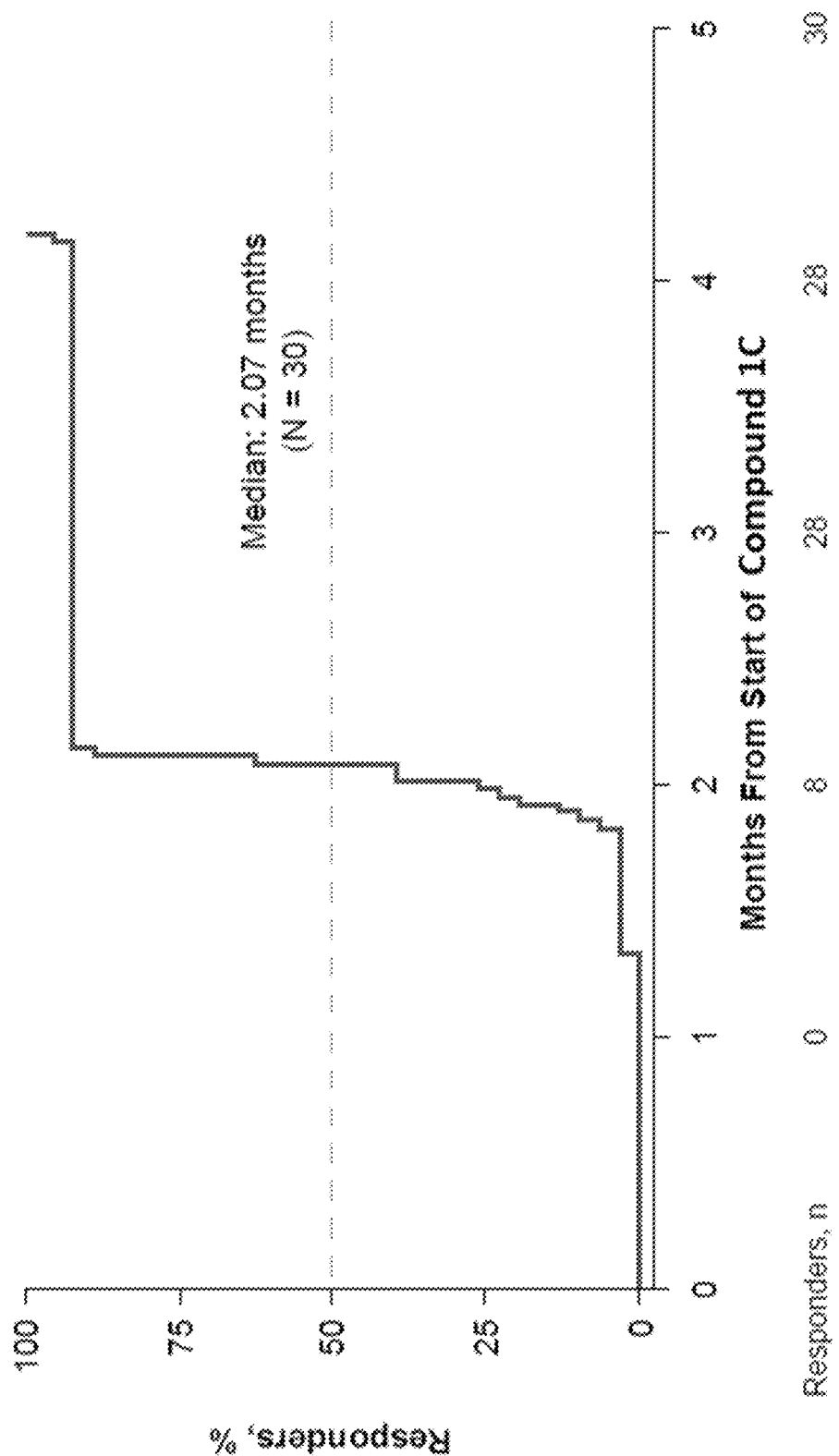
FIG. 6 shows Compound 1C monotherapy time to response among NHL subtypes of interest (DLBCL, FL, MCL, MZL). DLBCL, diffuse large B-cell lymphoma; FL, follicular lymphoma; MCL, mantle cell lymphoma; MZL, marginal zone lymphoma.
Figure 7:
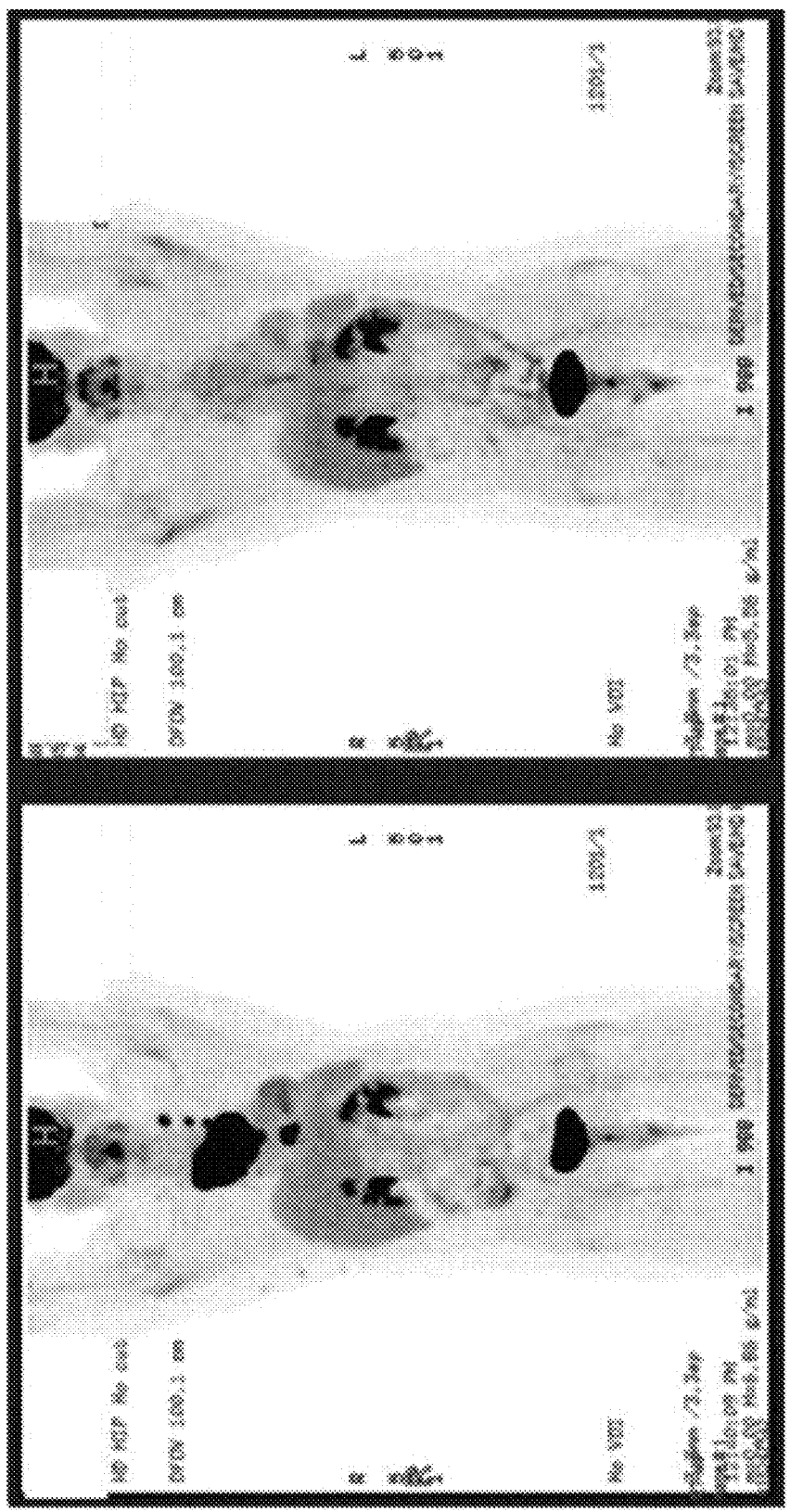
FIG. 7 shows representative positron emission tomography (PET) images of a patient who achieved complete response with Compound 1C monotherapy. Patient was <65 years of age, with mantle cell lymphoma with no bone marrow involvement (target lesion, 98 mm×58 mm) and had received 1 prior treatment (R-HyperCVAD). Treated with Compound 1C, 30 mg once daily; achieved complete response at week 9.

ORR among evaluable patients varied by disease type, as shown in Table 5. Among patients having evaluable lesion size at baseline and post-baseline, deep responses (>75% decrease from baseline in target lesion size) occurred in 4/7 patients (57%) with marginal zone lymphoma (MZL), 7/14 (50%) with follicular lymphoma (FL), 3/8 (38%) with mantle cell lymphoma (MCL), and 2/20 (10%) with diffuse large B-cell lymphoma (DLBCL) (FIG. 2). Among patients with these tumor types, the vast majority (93%) of responses occurred by the first assessment (~9 weeks), as shown in FIG. 6. Durable responses (>6 months) were observed among patients receiving QW dosing and several patients remained on the QW schedule for at least 8 months, as shown in FIG. 3, including 2 who were administered 10 mg QW. The median duration of response was 13.5 months (95% CI: 8.3-18.8) for DLBCL, 4.4 months (95% CI: 2.1-NE) for MZL, and was not reached for FL or MCL. FIG. 7 shows representative positron emission tomography (PET) images of a patient who achieved complete response with Compound 1C monotherapy. The patient was <65 years of age, with mantle cell lymphoma with no bone marrow involvement (target lesion, 98 mm×58 mm) and had received 1 prior treatment (R-HyperCVAD). Upon treatment with Compound 1C, 30 mg once daily, the patient achieved complete response at week 9.

Of the 11 patients treated with Compound 1C+itacitinib, 8 received Compound 1C 20 mg QD and 3 received Compound 1C 30 mg QD; all patients received itacitinib 300 mg QD. No DLTs were observed. Nine patients (82%) experienced TEAEs, 5 (45%) had grade 3/4 TEAEs, and 2 (18%) had SAEs. The most common any grade TEAEs (n≥2) were nausea, fatigue (n=5 each), cough, hypertension, vomiting (n=3 each), decreased appetite, hyperglycemia, lacrimation increased, oral herpes, and tachycardia (n=2 each). Five patients experienced grade 3/4 TEAEs: grade 3 spinal cord compression, grade 3 intractable pain, and grade 3 elevated alkaline phosphatase (n=1); grade 3 worsening hyperlipidemia (n=1); grade 3 hypertension (n=1); grade 3 diarrhea and grade 3 dehydration (n=1); and grade 3 hypertension and grade 4 hypercalcemia (n=1). One patient had a new/worsening grade 4 hematologic laboratory abnormality (thrombocytopenia). One SAE each of grade 3 dehydration

TABLE 5

Best overall response among patients receiving Compound 1C monotherapy*

| Patients | N | ORR, n (% [95% CI])† | CR/CMR, n (%) | PR/PMR, n (%) | SD, n (%) | PD/PMD, n (%) | Not evaluable/ not assessed, n (%) |
|---|---|---|---|---|---|---|---|
| DLBCL‡ | 23 | 7 (30 [13-53]) | 4 (17) | 3 (13) | 4 (17) | 11 (48) | 1 (4) |
| GCB | 19 | 6 (32 [13-57]) | 4 (21) | 2 (11) | 3 (16) | 9 (47) | 1 (5) |
| ABC | 2 | 1 (50 [1-99]) | 0 (0) | 1 (50) | 0 (0) | 1 (50) | 0 |
| FL | 14 | 10 (71 [42-92]) | 3 (21) | 7 (50) | 1 (7) | 2 (14) | 1 (7) |
| MZL¶ | 9 | 7 (78 [40-97]) | 3 (33) | 4 (44) | 1 (11) | 1 (11) | 0 |
| MCL‖ | 9 | 6 (67 [30-93]) | 4 (44) | 2 (22) | 2 (22) | 0 (0) | 1 (11) |
| HL** | 10 | 2 (20 [3-56]) | 0 (0) | 2 (20) | 3 (30) | 4 (40) | 1 (10) |
| CLL‖ | 6 | 2 (33 [4-78]) | 0 (0) | 2 (33) | 2 (33) | 1 (17) | 1 (17) |
| WM | 1 | 1 (100 [3-100]) | 0 (0) | 1 (100) | 0 (0) | 0 (0) | 0 |

*Assessed by Lugano Classification, CLL IWGC Criteria, and the VIth International Workshop on WM by Disease Subtype by CT or PET.
†95% CIs were calculated based on the exact method for binomial distributions.
‡Two patients had unknown DLBCL subtype.
¶Includes extranodal MZL of MALT type (n = 2), nodal MZL (n = 4), splenic MZL (n = 2), and unknown MZL subtype (n = 1).
‖4 patients with MCL and 3 patients with CLL had received ibrutinib before the study, of whom a best overall response of CR or PR was achieved by 2 patients with MCL and 1 patient with CLL.
**Includes classic HL (n = 9) and nodular lymphocytic-predominant HL (n = 1).
ABC, activated B cell-like;
CI, confidence interval;
CLL, chronic lymphocytic leukemia;
CMR, complete metabolic response;
CR, complete response;
CT, computed tomography;
DLBCL, diffuse large B-cell lymphoma;
FL, follicular lymphoma;
HL, Hodgkin lymphoma;
GCB, germinal center B-cell-like;
CLL IWGC, International Working Group for CLL;
MALT, mucosa-associated lymphatic tissue;
MCL, mantle cell lymphoma;
MZL, marginal zone lymphoma;
ORR, overall response rate;
PD, progressive disease;
PET, positron emission tomography;
PMD, progressive metabolic disease;
PMR, partial metabolic response;
PR, partial response;
SD, stable disease;
WM, Waldenström macroglobulinemia.

Example G. PI3Kδ Inhibitor Combination Therapy

Compound 1C Combined with Itacitinib

Eleven patients were enrolled and treated with Compound 1C+itacitinib. The median (range) duration of both Compound 1C and itacitinib treatment was 2.1 (1.0-10.3) months. At data cutoff, treatment was ongoing in 2 patients (18%); 8 patients (73%) discontinued treatment due to disease progression, and 1 (9%) due to TEAE.

and grade 4 hypercalcemia were reported. Two patients (18%) had TEAEs leading to dose interruption of both Compound 1C and itacitinib and 1 patient (9%) had a TEAE leading to discontinuation of both Compound 1C and itacitinib; no patient had a TEAE leading to dose reduction. No TEAEs led to death.

Among evaluable patients, best overall response of CR/complete metabolic response was achieved by patients with CLL (1/1) and FL (1/1); best overall response of partial metabolic response was achieved by patients with MCL (1/1) and classic HL (1/2). All 6 patients with DLBCL and 1 of 2 patients with classic HL had best overall response of PD/progressive metabolic disease.

Compound 1C Combined with R-ICE

Five patients with DLBCL were treated with Compound 1C+R-ICE. The median (range) duration of Compound 1C treatment was 2.3 (1.5-3.7) months; 4 patients received 3 cycles of R-ICE each, and 1 patient received 2 cycles of R-ICE. As of the data cutoff date, all patients have discontinued treatment due to physician decision (n=2), progressive disease, adverse events, and other (n=1 each). Of the 5 patients, 4 received Compound 1C 15 mg QD and 1 received 20 mg QD. No DLTs were observed. The most common any-grade nonhematologic TEAEs (≥2 patients) were dizziness (n=3), alopecia, constipation, fluid overload, headache, hypokalemia, and night sweats (n=2 each). Three patients reported new/worsening grade 4 thrombocytopenia and 2 patients reported new/worsening grade 4 neutropenia. Two patients (40%) experienced SAEs, 1 patient experienced grade 3 acute encephalopathy (related to ifosfamide), and 1 experienced grade 2 atrial flutter and atrial fibrillation and grade 3 dyspnea, neutropenia, and febrile neutropenia (all related to both Compound 1C and R-ICE). Three patients (60%) had TEAEs leading to dose interruption of both Compound 1C and R-ICE, 1 patient (20%) had a TEAE leading to dose interruption of only Compound 1C, and 1 patient (20%) had TEAEs leading to discontinuation of both Compound 1C and R-ICE; no patient had a TEAE leading to dose reduction. No TEAEs led to death.

Of the 5 patients treated with Compound 1C+R-ICE, 3 patients achieved a complete metabolic response (1 of the 3 patients indicated a desire to proceeded to SCT) and 2 patients had stable disease as best response.

Example H. Results of the PI3Kδ Monotherapy and Combination Therapies

Compound 1C demonstrated a differentiated safety profile relative to first-generation PI3Kδ inhibitors (e.g., idelalisib and duvelisib) (Coutré S. E. et al, *Leukemia & Lymphoma.* 2015; 56(10):2779-2786; Flinn I. W. et al, *Blood,* 2018; 131(8):877-887), most notably by the near absence of grade ≥2 transaminitis. Unlike copanlisib, a pan-PI3K inhibitor that is approved in the United States as monotherapy for the treatment of relapsed FL (ALIQOPA™. (copanlisib) for injection, for intravenous use. U.S. Whippany, NJ: Bayer HealthCare Pharmaceuticals Inc.; 2017), there was also no clinically meaningful hypertension or hyperglycemia, presumably due to the high selectivity of Compound 1C for the δ isoform of PI3K. Although no PJP was observed, a protocol amendment made PJP prophylaxis mandatory partway through the study in response to a PJP infection reported in a different phase 1 study that combined Compound 1C with pembrolizumab.

Diarrhea/colitis and rash, toxicities common to PI3K inhibitors, were 2 of the most frequent toxicities observed in this study; nevertheless, the majority of diarrhea events were of grade 1 or 2 and were manageable. The majority of grade 3/4 diarrhea/colitis and rash occurred after the first disease assessment; overall any grade diarrhea/colitis or rash led to treatment discontinuation in 9/72 (13%) of patients, including 3 patients with diarrhea/colitis who were positive upon rechallenge at the same dose. Grade 4 neutropenia (6%) was observed only during QD dosing (earliest occurring after 21 days of treatment). The safety profile associated with the 20 mg QD dose was generally consistent with that observed for all doses combined and with that observed for each individual dose level (data not shown), although relatively few patients were dosed at levels below 20 mg QD and above 30 mg QD.

Long-term dosing of Compound 1C identified late-onset TEAEs that led to treatment discontinuation. To improve the long-term tolerability of Compound 1C while maintaining a high response rate, a modified dosing regimen was implemented (20 mg QD for 9 weeks followed by 20 mg QW). The period of daily dosing was maintained to preserve the potential for rapid onset of response (at the time of implementation, all 11 patients with NHL who were administered 20 mg QD had achieved an objective response, 10 of which occurred at the first disease assessment). The intermittent portion of the dosing regimen, which was implemented to decrease the incidence of late-onset TEAEs, was based on comparative PK/PD simulation with copanlisib (Patnaik A., et al, *Annals of Oncology,* 2016; 27(10):1928-1940). Without being bound by theory, the 20 mg QW regimen is anticipated to provide similar pAKT inhibition as expected from QW dosing of copanlisib. Encouragingly, none of the 26 patients who received QW dosing discontinued study treatment due to TEAEs, based on data accrued during a 105 patient-month period. This observation, combined with the absence of colitis, grade 4 nonhematologic TEAEs and neutropenia, and a low rate of grade 3 diarrhea and rash (n=1 each) suggest that the QW schedule is better tolerated than the continuous QD schedule using the doses evaluated herein.

Compound 1C monotherapy effected a high rate of rapid, deep, and durable objective responses in relapsed or refractory B-cell NHL at doses ranging from 10 mg QD to 45 mg QD. ORR across all subtypes ranged from 30% to 78% (DLBCL, 30%; MCL, 67%; FL, 71%, MZL, 78%) and deep responses occurred in >30% of patients. Anecdotally, objective responses were observed in 2 of the 4 patients with MCL that had been previously treated with ibrutinib; 1 of these responses was ongoing at approximately 6 months at data cutoff. Among patients with DLBCL, substantially more patients with GCB subtype (n=19) were enrolled relative to those with ABC subtype (n=2). These small, disproportionate numbers are insufficient to determine if Compound 1C is more active in one subtype than the other. Durable responses were observed in all 4 of these NHL subtypes including ~17 months in FL, ~10 months in MZL, ≥14 months in MCL, and ~19 months in DLBCL, all of which included QW dosing and 2 of whom (FL and MZL) had ongoing responses at data cutoff. Taken together, these data suggest that QW dosing of Compound 1C can enable durable responses in patients with B-cell NHL.

The PK and safety data from the combination studies show that Compound 1C can be safely combined with a 300 mg QD dose of itacitinib. Similarly, the combination of Compound 1C with R-ICE also appears to be tolerated. Additional studies are required to evaluate the safety of Compound 1C combined with R-ICE and the potential for increased efficacy for each of the combinations.

Compound 1C demonstrated anti-tumor activity with rapid and deep responses as well as high response rates and a differentiated toxicity profile in patients with relapsed or refractory B-cell malignancies. The modified dosing regimen described herein appeared to improve the long-term tolerability of Compound 1C and enabled durable responses in several patients. The efficacy, safety, PK, and PD data presented here support further investigation of Compound 1C monotherapy in ongoing phase 2 studies in select NHL subtypes (DLBCL [NCT02998476], FL [NCT03126019], MZL [NCT03144674], and MCL [NCT03235544]). Phase 1 studies exploring several combination strategies in patients with NHL (NCT03039114; NCT03424122) are also underway.

Example I. Comparative Maintenance Dosing

In this study, subjects are administered 20 mg of Compound 1C once daily for 8 weeks in combination with a JAK1 inhibitor. After week 8, subjects are assigned to 1 of 2 maintenance dose groups based on block randomization. In one group, subjects are administered 5 mg of Compound 1C once daily. In the second group, subjects are administered 20 mg of Compound 1C once weekly.

The safety and tolerability of Compound 1C is assessed by summary of treatment-emergent adverse events (TEAEs), clinical laboratory assessments, physical examination results, and 12-lead electrocardiograms. The severity of TEAEs is assessed using Common Terminology Criteria for Adverse Events version 4.03. Secondary endpoints are efficacy and PK, as described in Example E.

Without being bound by theory, the 5 mg once daily maintenance dose of Compound 1C is believed to provide similar safety and tolerability as the 20 mg once weekly maintenance dose of Compound 1C.

Example J. PI3Kδ Combination Therapy with JAK1/2 Inhibitor in Treatment of Myelofibrosis Compound 1C was evaluated in combination with ruxolitinib in patients with primary or secondary myelofibrosis (MF) (e.g., PMF, PPV-MF, or PET-MF) who have exhibited suboptimal response with ruxolitinib monotherapy. The study was designed in three parts, as follows:

Part 1, Safety Run-in: 3+3 design; ruxolitinib+Compound 1C administered in doses of 10 mg or 20 mg QD for 8 weeks, followed by 10 mg or 20 mg QW.

Part 2, Randomized Phase (1:1): Group 1: ruxolitinib+ Compound 1C administered in doses of 10 mg QD for 8 weeks, followed by 10 mg QW. Group 2: ruxolitinib+ Compound 1C administered in doses of 20 mg QD for 8 weeks followed by 20 mg QW.

Part 3: Additional dosing regimens, including continuous daily dosing.

The "suboptimal response" with ruxolitinib monotherapy was defined as follows:
- A patient treated with ruxolitinib for ≥6 months with stable dose for ≥8 weeks immediately prior to enrollment (acceptable doses of prior ruxolitinib: 5 mg-25 mg BID); and
- Palpable spleen >10 cm below left subcostal margin on physical examination at screening; or
- Palpable spleen 5 cm-10 cm below left subcostal margin on physical examination and active symptoms of myelofibrosis at the screening visit, defined as 1 symptom score ≥5; or 2 symptom scores ≥3 each, using the following screening symptom form: 10 point scale for each of 7 symptoms. Symptoms include: night sweats, pruritus, abdominal discomfort, pain under left ribs, early satiety, bone/muscle pain, and inactivity.

Dosing schemes and preliminary results of the Compound 1C+ruxolitinib study are shown in Appendix A, the disclosure of which is incorporated herein by reference in its entirety. As shown Appendix A, add on therapy with Compound 1C appears to provide additional clinical benefit in patients with MF who have suboptimal responses to ruxolitinib monotherapy. A reduction in spleen volume in 56% of patients was observed at week 12, with symptoms improving as early as 4 weeks; median symptom improvement at 24 weeks was 36%. The combination of Compound 1C and ruxolitinib was well tolerated in patients, with no dose limiting toxicities (DLTs) in Part 1 and an expected grade 3/4 adverse effect (AE) profile. Of 17 patients on therapy >6 months, only 2 (7%) discontinuations were due to AEs. AEs common to PI3Kδ inhibitors, such as hepatic, rash, and colitis, were infrequent.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating a disease in a patient, wherein said disease is associated with abnormal expression or activity of PI3Kδ kinase, the method comprising:
   i) administering to the patient an inhibitor of PI3Kδ, which is 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one, or a pharmaceutically acceptable salt thereof, in a first dosage that is about 3 mg/day to about 50 mg/day for a first period of time which is about 2 weeks to about 12 weeks; and
   ii) administering to the patient a second dosage of the inhibitor of PI3Kδ which is less than the first dosage administered at the end of the first period of time and which is:
      (a) about 2.5 mg/day or less; or
      (b) about 50 mg/week or less;
   and wherein the second dosage is administered for a second period of time which occurs after the first period of time.

2. The method of claim 1, wherein the first dosage is about 20 mg/day.

3. The method of claim 1, wherein the first period of time is about 8 weeks to about 12 weeks.

4. The method of claim 1, wherein the first period of time is about 8 weeks.

5. The method of claim 1, wherein the first dosage is reduced during the first period of time.

6. The method of claim 1, wherein the second dosage is about 2.5 mg/day or less.

7. The method of claim 1, wherein the second dosage is about 2.5 mg/day.

8. The method of claim 1, wherein the second dosage is about 50 mg/week or less.

9. The method of claim 1, wherein the second dosage is about 20 mg/week.

10. The method of claim 1, wherein the second dosage is reduced during the second period of time.

11. The method of claim 5, wherein the patient has been identified as exhibiting one or more symptoms associated with one or more treatment-emergent adverse events (TEAEs).

12. The method of claim 11, wherein the patient has been identified as exhibiting the one or more symptoms associated with one or more treatment-emergent adverse events (TEAEs) during the first period of time.

13. The method of claim 11, wherein the first time period ends when the patient has been identified as exhibiting the one or more symptoms associated with one or more treatment-emergent adverse events (TEAEs).

14. The method of claim 11, wherein the one or more treatment-emergent adverse events comprise one or more of diarrhea/colitis, nausea, fatigue, rash, neutropenia, pyrexia, hypotension, sepsis, respiratory failure, pneumonitis, pneumonia, hypertension, hyperglycemia, abdominal pain, bronchitis, dehydration, thrombocytopenia, cough, vomiting, decreased appetite, increased lacrimation, oral herpes, tachycardia, spinal cord compression, intractable pain, elevated alkaline phosphatase, elevated transaminase, hyperlipidemia, hypercalcemia, dizziness, alopecia, constipation, fluid overload, headache, hypokalemia, night sweats, encephalopathy, atrial flutter, atrial fibrillation, and dyspnea.

15. The method of claim 11, wherein the one or more treatment-emergent adverse events comprise one or more of diarrhea/colitis, nausea, fatigue, rash, cough, vomiting, dizziness, pyrexia, hypokalemia, abdominal pain, constipation, decreased appetite, night sweats, pruritus, back pain, chills, leukopenia, neutropenia, lymphopenia, thrombocytopenia, and anemia.

16. The method of claim 11, wherein the one or more treatment-emergent adverse events comprise one or more of diarrhea/colitis and rash.

17. The method of claim 16, wherein the diarrhea/colitis comprises one or more of diarrhea, colitis, enterocolitis, gastrointestinal inflammation, colitis microscopic, and cytomegalovirus colitis.

18. The method of claim 16, wherein the rash comprises one or more of dermatitis exfoliative, rash, rash erythematous, rash macular, rash maculopapular, rash pruritic, exfoliative rash, rash generalized, rash popular, and rash pustular.

19. The method of claim 14, wherein the neutropenia comprises febrile neutropenia.

20. The method of claim 14, wherein the elevated transaminase comprises elevated alanine transaminase (ALT), aspartate transaminase (AST), or a combination thereof.

21. The method of claim 1, wherein the inhibitor of PI3Kδ is (S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one, or a pharmaceutically acceptable salt thereof.

22. The method of claim 1, wherein the inhibitor of PI3Kδ is (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one, or a pharmaceutically acceptable salt thereof.

23. The method of claim 1, wherein the inhibitor of PI3Kδ is (S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one, or a pharmaceutically acceptable salt thereof.

24. The method of claim 1, wherein the inhibitor of PI3Kδ is (R)-4-(3-(R)-1-(4-amino-3-methyl-1H-pyrazolo[3,4-d]pyrimidin-1-yl)ethyl)-5-chloro-2-ethoxy-6-fluorophenyl)pyrrolidin-2-one, or a pharmaceutically acceptable salt thereof.

25. The method of claim 1, wherein the inhibitor of PI3Kδ is a pharmaceutically acceptable salt of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one.

26. The method of claim 1, wherein the inhibitor of PI3Kδ is (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt.

27. The method of claim 26, wherein the salt is a 1:1 stoichiometric ratio of (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one to hydrochloric acid.

28. The method of claim 26, wherein the salt is crystalline.

29. The method of claim 1, wherein the disease is selected from chronic lymphocytic leukemia, diffuse large B-cell lymphoma, follicular lymphoma, Hodgkin lymphoma, mantle cell lymphoma, marginal zone lymphoma, and Waldenström macroglobulinemia.

30. The method of claim 29, wherein the marginal zone lymphoma is selected from extranodal marginal zone lymphoma, nodal marginal zone lymphoma, splenic marginal zone lymphoma, and unknown marginal zone lymphoma subtype.

31. The method of claim 29, wherein the Hodgkin lymphoma is selected from classic Hodgkin lymphoma and nodular lymphocytic-predominant Hodgkin lymphoma.

32. The method of claim 29, wherein the diffuse large B-cell lymphoma is selected from activated B-cell like diffuse large B cell lymphoma and germinal center B cell diffuse large B cell lymphoma.

33. A method of treating a disease in a patient, wherein said disease is selected from chronic lymphocytic leukemia, diffuse large B-cell lymphoma, follicular lymphoma, Hodgkin lymphoma, mantle cell lymphoma, marginal zone lymphoma, and Waldenström macroglobulinemia, the method comprising:
  i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day to about 50 mg/day for a first period of time which is about 8 weeks to about 9 weeks; and
  ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 2.5 mg/day or less for a second period of time which occurs after the first period of time.

34. A method of treating a disease in a patient, wherein said disease is selected from chronic lymphocytic leukemia, diffuse large B-cell lymphoma, follicular lymphoma, Hodgkin lymphoma, mantle cell lymphoma, marginal zone lymphoma, and Waldenström macroglobulinemia, the method comprising:
  i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day to about 50 mg/day for a first period of time which is about 8 weeks to about 9 weeks; and
  ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 20 mg/week to about 50 mg/week for a second period of time which occurs after the first period of time.

35. A method of treating a disease in a patient, wherein said disease is selected from chronic lymphocytic leukemia, diffuse large B-cell lymphoma, follicular lymphoma, Hodgkin lymphoma, mantle cell lymphoma, marginal zone lymphoma, and Waldenström macroglobulinemia, the method comprising:
  i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day for a first period of time which is about 8 weeks; and ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 2.5 mg/day for a second period of time which occurs after the first period of time.

36. A method of treating a disease in a patient, wherein said disease is selected from chronic lymphocytic leukemia, diffuse large B-cell lymphoma, follicular lymphoma, Hodgkin lymphoma, mantle cell lymphoma, marginal zone lymphoma, and Waldenström macroglobulinemia, the method comprising:
   i) administering to the patient (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt in a first dosage that is about 20 mg/day for a first period of time which is about 8 weeks; and
   ii) administering to the patient a second dosage of the (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt, which is about 20 mg/week for a second period of time which occurs after the first period of time.

37. A method of treating a disease in a patient, wherein said disease is associated with abnormal expression or activity of PI3Kδ kinase, the method comprising:
   i) administering to the patient an inhibitor of PI3Kδ, which is 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one, or a pharmaceutically acceptable salt thereof, in a first dosage that is about 3 mg/day to about 50 mg/day for a first period of time which is about 2 weeks to about 12 weeks; and
   ii) administering to the patient a second dosage of the inhibitor of PI3Kδ which is less than the first dosage administered at the end of the first period of time and which is between about 2.5 mg/day and about 7.5 mg/day; and
   wherein the second dosage is administered for a second period of time which occurs after the first period of time.

38. The method of claim 37, wherein the second dosage is about 3.0 mg/day to about 7.0 mg/day.

39. The method of claim 37, wherein the second dosage is about 4.0 mg/day to about 6.0 mg/day.

40. The method of claim 37, wherein the second dosage is about 5.0 mg/day.

41. The method of claim 37, wherein said inhibitor of PI3Kδ is (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one hydrochloric acid salt.

42. The method of claim 37, wherein said disease is selected from chronic lymphocytic leukemia, diffuse large B-cell lymphoma, follicular lymphoma, Hodgkin lymphoma, mantle cell lymphoma, marginal zone lymphoma, and Waldenström macroglobulinemia.

43. The method of claim 42, wherein the marginal zone lymphoma is selected from extranodal marginal zone lymphoma, nodal marginal zone lymphoma, splenic marginal zone lymphoma, and unknown marginal zone lymphoma subtype.

44. The method of claim 42, wherein the Hodgkin lymphoma is selected from classic Hodgkin lymphoma and nodular lymphocytic-predominant Hodgkin lymphoma.

45. The method of claim 42, wherein the diffuse large B-cell lymphoma is selected from activated B-cell like diffuse large B cell lymphoma and germinal center B cell diffuse large B cell lymphoma.

* * * * *

UNITED STATES PATENT AND TRADEMARK OFFICE
CERTIFICATE OF CORRECTION

Page 1 of 1

PATENT NO. : 12,226,418 B2
APPLICATION NO. : 16/428056
DATED : February 18, 2025
INVENTOR(S) : Krishnaswamy Yeleswaram, Albert Assad and Xuejun Chen It is certified that error appears in the above-identified patent and that said Letters Patent is hereby corrected as shown below:

In the Claims

Column 74, Lines 21-23: In Claim 1, delete "4-{3-[1-(4-amino-3-methyl-1H-pyrazolo[3,4-d]pyrimidin-1-yl)ethyl]-5-chloro-2- ethoxy-6-fluorophenyl}pyrrolidin-2-one" and insert -- 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one --.

Column 75, Lines 50-52: In Claim 24, delete "(R)-4-(3-(R)-1(4-amino-3-methyl-1H-pyrazolo[3,4-d]pyrimidin-1-yl)ethyl)-5-chloro-2-ethoxy-6-fluorophenyl)pyrrolidin-2-one" and insert -- (R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one --.

Signed and Sealed this
Eighth Day of April, 2025

Coke Morgan Stewart
*Acting Director of the United States Patent and Trademark Office*